US008551721B2

(12) United States Patent
Anderson et al.

(10) Patent No.: US 8,551,721 B2
(45) Date of Patent: Oct. 8, 2013

(54) BIOLUMINESCENT DETECTION OF CYANOHYDROXY BENZOTHIAZOLE COMPOUNDS

(75) Inventors: Jessica Anderson, Monticello, WI (US); Poncho Meisenheimer, San Luis Obispo, CA (US); John Shultz, Verona, WI (US); James J. Cali, Verona, WI (US); Dongping Ma, Madison, WI (US)

(73) Assignee: Promega Corporation, Madison, WI (US)

( * ) Notice: Subject to any disclaimer, the term of this patent is extended or adjusted under 35 U.S.C. 154(b) by 798 days.

(21) Appl. No.: 12/556,505

(22) Filed: Sep. 9, 2009

(65) Prior Publication Data

US 2010/0075351 A1      Mar. 25, 2010

Related U.S. Application Data

(60) Provisional application No. 61/095,514, filed on Sep. 9, 2008.

(51) Int. Cl.
*C12Q 1/66* (2006.01)
*A61K 38/04* (2006.01)

(52) U.S. Cl.
USPC .................. 435/8; 435/7.2; 435/25; 435/7.4; 435/7.72; 530/330

(58) Field of Classification Search
USPC ......... 435/7.72, 8, 7.74, 25, 7.2, 7.4; 530/330
See application file for complete search history.

(56) References Cited

U.S. PATENT DOCUMENTS

| 5,424,440 | A | 6/1995 | Klem et al. |
|---|---|---|---|
| 6,376,208 | B1 | 4/2002 | Kajiyama |
| 7,122,303 | B2 | 10/2006 | Delenstarr et al. |
| 2003/0211560 | A1* | 11/2003 | O'Brien et al. ................ 435/8 |
| 2004/0171099 | A1* | 9/2004 | Cali et al. .................... 435/25 |
| 2004/0254120 | A1* | 12/2004 | Fogelman et al. ............ 514/18 |
| 2009/0148386 | A1* | 6/2009 | Mao et al. ................... 424/9.6 |
| 2011/0223625 | A1 | 9/2011 | Kelts |

FOREIGN PATENT DOCUMENTS

| EP | 1935986 | 6/2008 |
|---|---|---|
| WO | 2006/130551 | 12/2006 |
| WO | 2010/030343 | 3/2010 |
| WO | 2011/112966 | 9/2011 |

OTHER PUBLICATIONS

European Patent Office Examination Report for Application No. 09789278.0 dated Apr. 19, 2012 (6 pages).
Niwa, K. et al., "Applications of luciferin biosynthesis: bioluminescence assays for 1-cysteine and luciferase," Anal. Biochem. (2010) 396(2):316-318.
International Search Report and Written Opinion for Application No. PCT/US2011/028147 dated May 25, 2011 (11 pages).
Monsees, T. et al., "Synthesis and characterization of a bioluminogenic substrate for alpha-chymotrypsin," Anal. Biochem. (1994) 221(2):329-334.
Shinde, R. et al., "Luciferin derivatives for enhances in vitro and in vivo bioluminescence assays," Biochem. (2006) 45:11103-11112.
International Search Report and Written Opinion for Application No. PCT/US2009/005052 dated Jan. 29, 2010 (12 pages).
Becker, C. F. W., et al., "C-Terminal Fluorescence Labeling of Proteins for Interaction Studies on the Single-Molecule Level", *ChemBioChem*, 7(6), (2006), 891-895.
Carreras, C. W., et al., "A C-terminal conformational equilibrium in thymidylate synthase observed by electron paramagnetic resonance spectroscopy", *Biochemistry*, 33(8), (1994), 2071-2077.
Chen, Q., et al., "Construction, properties and specific fluorescent labeling of a bovine prothrombin mutant engineered with a free C-terminal cysteine", *Protein Engineeering*, 9(6), (1996), 545-553.
Dirksen, A., et al., "Strategy for the synthesis of multivalent peptide-based nonsymmetric dendrimers by native chemical ligation", *Chem. Commun.*, (2006), 1667-1669.
Hong, S.-H., et al., "Domain-specific fluorescence resonance energy transfer (FRET) sensors of metallothionein/thionein", *Protein Engineering Design and Section*, 18(6), (2005), 255-263.
Kapanidis, A. N., et al., "Fluorescent probes and bioconjugation chemistries for single-molecule fluorescence analysis of biomolecules", *Journal of Chemical Physics*, 117(24), (2002), 10953-10964.
Kushnir, S., et al., "Rapid Production of Functionalized Recombinant Proteins: Marrying Ligation Independent Cloning and In Vitro Protein Ligation", *Bioconjugate Chem.*, 17, (2006), 610-617.
O'Brien, M. A, et al., "Homogeneous Bioluminescent Protease Assays : Caspase-3 as a Model", *Journal of Biomolecular Screening*,10(2), (2005), 137-148.
Schuette, C. G., et al., "Determinants of liposome fusion mediated by synaptic SNARE proteins", *Proc. Natl Acad. Sci. USA*, 101(9), (2004), 2858-2863.
United States Patent Office Action for U.S. Appl. No. 13/046,374 dated Aug. 9, 2012 (16 pages).
McCapra, F., "Chemical Mechanisms in Bioluminescence," Accounts of Chemical Research (1976) 9(6): 201-208.
United States Patent Office Action for U.S. Appl. No. 13/046,374 dated Jan. 14, 2013 (6 pages).

* cited by examiner

*Primary Examiner* — Susan Hanley
(74) *Attorney, Agent, or Firm* — Michael Best & Friedrich LLP

(57) ABSTRACT

The invention provides methods that employ derivatives of 2-cyano-6-hydroxy- or 2-cyano-6-amino-benzothiazole, for example, in a bioluminogenic reaction. Also provided are novel compounds that can be used in the methods. The invention further provides methods for detecting or determining the presence of molecules and/or enzymes, the modulator activity of such molecules, and/or the activity of such enzymes. The methods are adaptable to high-throughput format.

33 Claims, 22 Drawing Sheets

LUCIFERIN

US 8,551,721 B2

BIOLUMINESCENT DETECTION OF CYANOHYDROXY BENZOTHIAZOLE COMPOUNDS

RELATED APPLICATION

This application claims priority under 35 U.S.C. §119(e) to U.S. Provisional Patent Application No. 61/095,514, filed Sep. 9, 2008, which is incorporated herein by reference.

BACKGROUND

Luminescence is produced in certain organisms as a result of a luciferase-mediated oxidation reaction. Luciferase genes from a wide variety of vastly different species, particularly the luciferase genes of Photinus pyralis and Photuris pennsylvanica (fireflies of North America), Pyrophorus plagiophthalamus (the Jamaican click beetle), Renilla reniformis (the sea pansy), and several bacteria (e.g., Xenorhabdus luminescens and Vibrio spp), are extremely popular luminescence reporter genes. Firefly luciferase is also a popular reporter for determining ATP concentrations, and, in that role, is widely used to detect biomass. Luminescence is also produced by other enzymes when those enzymes are mixed with certain synthetic substrates, for instance, alkaline phosphatase and adamantyl dioxetane phosphate, or horseradish peroxidase and luminol.

Luciferase genes are widely used as genetic reporters due to the non-radioactive nature, sensitivity, and extreme linear range of luminescence assays. For instance, as few as $10^{-20}$ moles of firefly luciferase can be detected. Consequently, luciferase assays of gene activity are used in virtually every experimental biological system, including both prokaryotic and eukaryotic cell cultures, transgenic plants and animals, and cell-free expression systems. Similarly, luciferase assays used to determine ATP concentration are highly sensitive, enabling detection to below $10^{-16}$ moles.

Luciferases can generate light via the oxidation of enzyme-specific substrates, e.g., luciferins. For firefly luciferase and all other beetle luciferases, light generation occurs in the presence of luciferin, magnesium ions, oxygen, and ATP. For anthozoan luciferases, including Renilla luciferase, only oxygen is required along with the substrate coelentrazine. Generally, in luminescence assays to determine genetic activity, reaction substrates and other luminescence activating reagents are introduced into a biological system suspected of expressing a reporter enzyme. Resultant luminescence, if any, is then measured using a luminometer or any suitable radiant energy-measuring device. The assay is very rapid and sensitive, and provides gene expression data quickly and easily, without the need for radioactive reagents.

Because most enzymatic reactions do not generate outputs that are as ideal as luciferase, the availability of a luciferase-mediated assay for enzymatic reactions useful in cellular analysis, and high-throughput screening applications would be desirable. Luciferase-mediated reactions have been employed to detect numerous other molecules, e.g., ATP or lactate dehydrogenase. For some of those reactions, a derivative of the naturally occurring substrate is employed. Native firefly luciferin, a polyheterocyclic organic acid, D-(−)-2-(6'-hydroxy-2'-benzothiazolyl)-$\Delta^2$-thiazolin-4-carboxylic acid, is shown in FIG. 1. For instance, methods for using luciferin derivatives with a recognition site for an enzyme, such as a protease, as a prosubstrate were described by Miska et al. (Journal of Clinical Chemistry and Clinical Biochemistry, 25:23 (1987)). The heterogeneous assays were conducted by incubating the luciferin derivative with the appropriate enzyme, e.g., a protease, for a specified period of time, then transferring an aliquot of the mixture to a solution containing luciferase. Masuda-Nishimura et al. (Letters in Applied Microbio., 30:130 (2000)) reported the use of a single tube (homogeneous) assay that employed a galactosidase substrate-modified luciferin. In these luciferin derivatives, the portion of the derivative functioning as the reactive group for the nonluciferase enzyme activity was coupled to the D-luciferin or aminoluciferin backbone such that upon the action of the nonluciferase enzyme, a D-luciferin or aminoluciferin molecule was produced as the direct product of the reaction to serve as the substrate for luciferase.

A primary obstacle to broadly applying luciferase-mediated reactions for other enzymatic assays has been the belief that to modify the luciferin molecule to function as a substrate for a nonluciferase enzyme, the activity of the nonluciferase enzyme must directly yield a D-luciferin or aminoluciferin molecule to retain its function as a substrate for luciferase. Moreover, many enzymes of interest do not recognize luciferin derivatives modified to include the appropriate substrate for a variety of reasons, including the size of the derivative and a lack of interaction or activity with respect to modification at the carboxyl group of luciferin. Further, certain cell based assays may be limited due to low permeability of luciferin derivatives and instability of luciferin derivatives that are esterified at the carboxylic acid.

Accordingly, there is a need for bioluminogenic assays that employ substrates other than luciferin derivatives.

SUMMARY OF THE INVENTION

The invention provides methods for performing an assay for enzymes of interest using derivatives of 2-cyano-6-hydroxybenzothiazole or 2-cyano-6-aminobenzothiazole (derivatives of "2-cyano-6-substituted benzothiazole" hereinafter). The invention also provides methods for performing an assay to determine the activity of enzyme modulators. The invention further provides novel compounds and compositions that can be used in enzyme assays.

In one embodiment, the present invention provides derivatives of 2-cyano-6-substituted benzothiazole and methods for using such derivatives in enzyme activity assays or non-enzymatic biological assays, where the derivative serves as a substrate for a desired enzyme or reaction, and yields a product which in the presence of D-cysteine provides a bioluminogenic substrate for luciferase. Thus, by providing 2-cyano-6-substituted benzothiazole derivatives having a particular enzyme recognition site for a desired nonluciferase enzyme (a substrate) coupled to the 2-cyano-6-substituted benzothiazole backbone, e.g., coupled to the 6'-hydroxy site or a 6'-amino site, numerous nonluciferase enzymes may be detected in a bioluminescent assay, and/or their activity may be measured in a bioluminescent assay. The invention also provides methods for comparing an assays of the invention to a control to detect a nonluciferase enzyme, and/or its activity.

Accordingly, the invention provides a method to detect or determine the presence or activity of a nonluciferase enzyme in a sample comprising a) providing a first mixture comprising a sample, a first reaction mixture for a nonluciferase enzyme-mediated reaction, and a derivative of 2-cyano-6-substituted benzothiazole which includes a substrate for the nonluciferase enzyme, wherein the derivative in the presence of D-cysteine yields a product that is a bioluminogenic substrate for a beetle luciferase;

b) contacting at least a portion of the first mixture with a second reaction mixture for a beetle luciferase-mediated reaction, so as to yield a second mixture; and c) detecting or determining luminescence in the second mixture, thereby detecting or determining the presence or amount of the nonluciferase enzyme in the sample. In one embodiment, D-cysteine can be present in the first mixture. In another embodiment, D-cysteine can be present in the second mixture.

The invention also provides a method to detect or determine the presence or activity of a nonluciferase enzyme in a sample comprising a) providing a first mixture comprising a sample, a first reaction mixture for a nonluciferase enzyme-mediated reaction, and a derivative of 2-cyano-6-substituted benzothiazole which includes a substrate for the nonluciferase enzyme, wherein the first mixture does not include a cofactor specific for the nonluciferase enzyme's activity, and wherein the derivative in the presence of D-cysteine and the nonluciferase enzyme would yield a product that is a bioluminogenic substrate for a beetle luciferase in the absence of the cofactor;

b) contacting at least a portion of the first mixture with a second reaction mixture for a beetle luciferase-mediated reaction which includes D-cysteine, so as to yield a second mixture; and c) comparing luminescence in the second mixture to luminescence in a control mixture in which a third mixture having the sample, a first reaction mixture for a nonluciferase enzyme-mediated reaction, the derivative of 2-cyano-6-substituted benzothiazole, and a necessary cofactor for the nonluciferase enzyme, is contacted with a reaction mixture for the beetle luciferase-mediated reaction which includes D-cysteine, thereby detecting or determining the presence or amount of the nonluciferase enzyme in the sample.

The nonluciferase enzyme can be any enzyme that, for example, requires a cofactor for its activity. The enzymes include, but are not limited to the various enzymes described herein, such as UGT, GST, CYP450, FMO, HDAC, and/or a protease. The first reaction mixture for the nonluciferase enzyme-mediated reaction can include a test modulator for a nonluciferase enzyme-mediated reaction. The modulator can be, for example, an inhibitor of the nonluciferase enzyme, a competitive substrate for the nonluciferase enzyme, and/or an activator for the nonluciferase enzyme.

The sample can include tissue extracts or recombinant microsomes. The microsomes can express specific isozymes. The microsomes can be, for example, recombinant microsomes or mammalian microsomes.

In another embodiment, the invention provides a method to detect or determine the presence or amount of UGT in a sample comprising a) providing a first mixture comprising a sample, a first reaction mixture for a UGT-mediated reaction, and a derivative of 2-cyano-6-substituted benzothiazole which is a substrate for the UGT, wherein the first mixture does not include UDPGA, and wherein the derivative in the presence of D-cysteine and the UGT would yield a product that is a bioluminogenic substrate for a beetle luciferase. In various embodiments, the UGT does not react with the derivative because the reaction mixture lacks the UGT cofactor UDPGA.

The method further includes b) contacting at least a portion of the first mixture with a second reaction mixture for a beetle luciferase-mediated reaction which includes D-cysteine, so as to yield a second mixture; and c) comparing luminescence in the second mixture to luminescence in a control mixture in which a third mixture having the sample, a first reaction mixture for a UGT-mediated reaction, the derivative of 2-cyano-6-substituted benzothiazole, and UDPGA, that is contacted with a reaction mixture for the beetle luciferase-mediated reaction which includes D-cysteine, thereby detecting or determining the presence or amount of UGT in the sample. The UGT can convert the 2-cyano-6-substituted benzothiazole into a derivative that is not a substrate for a luciferin enzyme, thus allowing for a difference in light output between the control and the test reaction.

The first reaction mixture for the UGT-mediated reaction can include a test modulator of a UGT-mediated reaction, such as a drug or xenobiotic to be evaluated. The modulator can be, for example, an inhibitor of UGT, or a competitive substrate for UGT. The sample can include tissue extracts or recombinant microsomes. The extracts or microsomes can express one or more specific isozymes.

The invention further provides a method to detect or determine activity of a nonluciferase enzyme modulator in a sample comprising a) providing a first mixture comprising a sample that includes microsomes expressing the nonluciferase enzyme, a first reaction mixture for a nonluciferase enzyme-mediated reaction, a compound to be evaluated for the modulator activity with respect to the nonluciferase enzyme, and a derivative of 2-cyano-6-substituted benzothiazole which is a substrate for the nonluciferase enzyme, wherein the first mixture does not include a cofactor specific for the nonluciferase enzyme's activity, and wherein the derivative in the presence of D-cysteine and the nonluciferase enzyme would yield a product that is a bioluminogenic substrate for a beetle luciferase;

b) contacting at least a portion of the first mixture with a second reaction mixture for a beetle luciferase-mediated reaction which includes D-cysteine, so as to yield a second mixture; and c) comparing luminescence in the second mixture to luminescence in a control mixture in which a third mixture having the sample that includes microsomes expressing the nonluciferase enzyme, a first reaction mixture for a nonluciferase enzyme-mediated reaction, a compound to be evaluated for modulator activity with respect to the nonluciferase enzyme, the derivative of 2-cyano-6-substituted benzothiazole, and a necessary cofactor for the nonluciferase enzyme, is contacted with a reaction mixture for the beetle luciferase-mediated reaction which includes D-cysteine, thereby detecting or determining the nonluciferase enzyme modulation activity of the compound to be evaluated in the sample.

The nonluciferase enzyme can be, for example, UGT, GST, CYP450, FMO, HDAC, and/or a protease. The compound to be evaluated for modulator activity is an inhibitor of the nonluciferase enzyme, a competitive substrate for the nonluciferase enzyme, or an activator of the nonluciferase enzyme. The microsomes can be recombinant microsomes, and the microsomes can express specific isozymes.

The invention further provides a method to detect or determine activity of a UGT modulator in a sample. The method can include a) providing a first mixture comprising a sample that includes microsomes expressing UGT, a first reaction mixture for a UGT-mediated reaction, a compound to be evaluated for UGT modulator activity, and a derivative of 2-cyano-6-substituted benzothiazole which is a substrate for the UGT, wherein the first mixture does not include UDPGA, and wherein the derivative in the presence of D-cysteine and the UGT would yield a product that is a bioluminogenic substrate for a beetle luciferase;

b) contacting at least a portion of the first mixture with a second reaction mixture for a beetle luciferase-mediated reaction which includes D-cysteine, so as to yield a second mixture; and c) comparing luminescence in the second mixture to luminescence in a control mixture in which a third mixture having the sample that includes microsomes expressing UGT, a first reaction mixture for a UGT-mediated reaction, a compound to be evaluated for UGT modulator activity, the derivative of 2-cyano-6-substituted benzothiazole, and UDPGA, that is contacted with a reaction mixture for the beetle luciferase-mediated reaction which includes D-cysteine, thereby detecting or determining the UGT modulation activity of the compound to be evaluated in the sample.

The microsomes expressing UGT can express a specific UGT isozyme. The microsomes can be, for example, recombinant microsomes, or mammalian microsomes. The derivative of 2-cyano-6-substituted benzothiazole can be a compound of formula I:

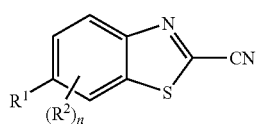

wherein
$R^1$ is OH or $NHR^x$;
$R^2$ is $(C_1-C_3)$alkyl, trifluoromethyl, amino, nitro, or halo;
n is 0, 1, 2, or 3; and
$R^x$ is $(C_1-C_3)$alkylaryl wherein the aryl is optionally substituted with one to five halo, hydroxy, or amino groups. In other embodiments, derivative of 2-cyano-6-substituted benzothiazole can also be a compound of any one of formulas I-XV described herein. In one embodiment, the compound of formula I can be:

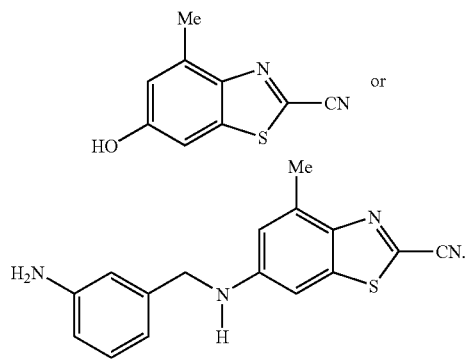

In other embodiments, derivative of 2-cyano-6-substituted benzothiazole can be a compound of any one of formulas I-XV described herein.

In another embodiment, the invention provides a method to detect or determine the presence or amount of an enzyme of interest, for example, UGT, in a sample comprising: a) providing a mixture comprising a sample, a first reaction mixture for a nonluciferase enzyme-mediated reaction, and a derivative of 2-cyano-6-substituted benzothiazole which is a substrate for the nonluciferase enzyme, wherein contact between the nonluciferase enzyme (for example, UGT or another enzyme) and the derivative and D-cysteine can yield a product that is a bioluminogenic substrate for a beetle luciferase;
b) contacting at least a portion of the first mixture with a second reaction mixture for a beetle luciferase-mediated reaction which includes D-cysteine, so as to yield a second mixture;
c) detecting or determining luminescence in the second mixture;
d) providing a mixture comprising the sample, a first reaction mixture for a nonluciferase enzyme-mediated reaction, the derivative of 2-cyano-6-substituted benzothiazole, which is a substrate for UGT, and UDPGA, so as to yield a third mixture, wherein a reaction between UGT and the derivative in the presence of UDPGA yields a product that in the presence of D-cysteine is a not bioluminogenic substrate for a beetle luciferase;
e) contacting at least a portion of the third mixture and the second reaction mixture for a beetle luciferase-mediated reaction which includes D-cysteine, so as to yield a fourth mixture;
f) detecting or determining luminescence in the fourth mixture; and g) comparing the amount of luminescence in the second and fourth mixtures, thereby detecting or determining the presence or amount of UGT in the sample.

The invention additionally provides a method to detect or determine activity of a UGT modulator in a sample comprising: a) providing a first mixture comprising a sample that includes microsomes expressing UGT, a first reaction mixture for a nonluciferase enzyme-mediated reaction, a compound to be evaluated for UGT modulator activity, and a derivative of 2-cyano-6-substituted benzothiazole which is a substrate for the nonluciferase enzyme, wherein a reaction between the nonluciferase enzyme and the derivative (for example, in the absence of UDPGA) can yield a product that in the presence of D-cysteine is a bioluminogenic substrate for a beetle luciferase;
b) contacting at least a portion of the first mixture with a second reaction mixture for a beetle luciferase-mediated reaction which includes D-cysteine, so as to yield a second mixture;
c) detecting or determining luminescence in the second mixture;
d) providing a mixture comprising the sample that includes microsomes expressing UGT, a first reaction mixture for a nonluciferase enzyme-mediated reaction, a compound to be evaluated for UGT modulator activity, the derivative of 2-cyano-6-substituted benzothiazole which is a substrate for UGT, and UDPGA, so as to yield a third mixture, wherein a reaction between UGT, UDPGA and the derivative would yield a product that in the presence of D-cysteine is a not bioluminogenic substrate for a beetle luciferase;
e) contacting at least a portion of the third mixture with the second reaction mixture for a beetle luciferase-mediated reaction which includes D-cysteine, so as to yield a fourth mixture;
f) detecting or determining luminescence in the fourth mixture; and
g) comparing the amount of luminescence in the second and fourth mixtures, thereby detecting or determining the UGT modulation activity of the compound to be evaluated in the sample.

Advantages of the methods of the invention include that the need for protein precipitation and/or chromatic purification steps are eliminated. The methods can readily be performed in multi-well plates and therefore can be carried out in high throughput formats. Accordingly, the methods can be used to screen large compound libraries for enzyme modulator activity.

DETAILED DESCRIPTION OF THE INVENTION

I. Definitions

Figure 1:
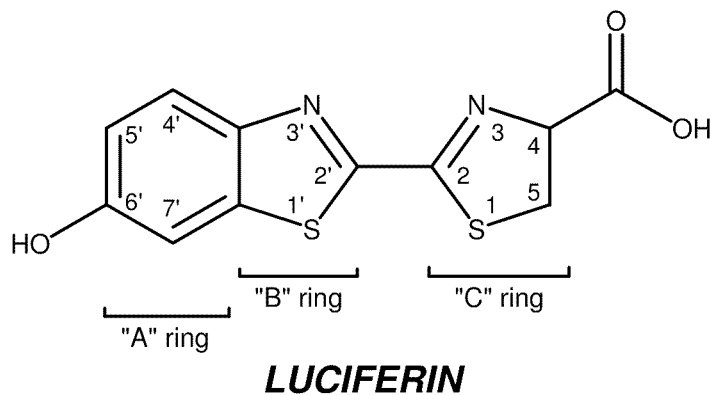
FIG. 1 illustrates the numbering of ring atoms in native firefly luciferin: the six membered "benzo" ring ("A ring"), five membered thiazole ring ("B ring"), and the five membered thiazolyl ring ("C ring").

As used herein, the following terms and expressions have the indicated meanings. It will be appreciated that the compounds of the present invention contain asymmetrically substituted carbon atoms, and may be isolated in optically active or racemic forms. It is well known in the art how to prepare optically active forms, such as by resolution of racemic forms or by synthesis from optically active starting materials. All chiral, diastereomeric, racemic forms and all geometric isomeric forms of a structure are part of this invention.

Specific values listed below for radicals, substituents, and ranges, are for illustration only; they do not exclude other defined values or other values within defined ranges for the radicals and substituents.

As used herein, the term "substituted" is intended to indicate that one or more (e.g., 1, 2, 3, 4, or 5; in some embodiments 1, 2, or 3; and in other embodiments 1 or 2) hydrogens on the group indicated in the expression using "substituted" is replaced with a selection from the indicated group(s), or with a suitable group known to those of skill in the art, provided that the indicated atom's normal valency is not exceeded, and that the substitution results in a stable compound. Suitable indicated groups include, e.g., alkyl, alkenyl, alkynyl, alkoxy, halo, haloalkyl, hydroxy, hydroxyalkyl, aryl, heteroaryl, heterocycle, cycloalkyl, alkanoyl, alkoxycarbonyl, amino, alkylamino, dialkylamino, trifluoromethylthio, difluoromethyl, acylamino, nitro, trifluoromethyl, trifluoromethoxy, carboxy, carboxyalkyl, keto, thioxo, alkylthio, alkylsulfinyl, alkylsulfonyl, arylsulfinyl, arylsulfonyl, heteroarylsulfinyl, heteroarylsulfonyl, heterocyclesulfinyl, heterocycle-sulfonyl, phosphate, sulfate, hydroxylamine, hydroxyl (alkyl)amine, and cyano. Additionally, the suitable indicated groups can include, e.g., —X, —R, —O⁻, —OR, —SR, —S⁻, —NR₂, —NR₃, =NR, —CX₃, —CN, —OCN, —SCN, —N=C=O, —NCS, —NO, —NO₂, =N₂, —N₃, NC(=O)R, —C(=O)R, —C(=O)NRR—S(=O)₂O⁻, —S(=O)₂OH, —S(=O)₂R, —OS(=O)₂OR, —S(=O)₂NR, —S(=O)R, —OP(=O)O₂RR, —P(=O)O₂RR—, P(=O)(O⁻)₂, —P(=O)(OH)₂, —C(=O)R, —C(=O)X, —C(S)R, —C(O)OR, —C(O)O⁻, —C(S)OR, —C(O)SR, —C(S)SR, —C(O)NRR, —C(S)NRR, —C(NR)NRR, where each X is independently a halogen ("halo"): F, Cl, Br, or I; and each R is independently H, alkyl, aryl, heteroaryl, heterocycle, a protecting group or prodrug moiety. As would be readily understood by one skilled in the art, when a substituent is keto (=O) or thioxo (=S), or the like, then two hydrogen atoms on the substituted atom are replaced.

Only stable compounds are contemplated by and claimed in the present invention, however, certain unstable compounds, for example, those that cannot easily be isolated, can be employed in the methods described herein. "Stable compound" and "stable structure" are meant to indicate a compound that is sufficiently robust to survive isolation to a useful degree of purity from a reaction mixture.

One diastereomer may display superior properties or activity compared with another. When required, separation of the racemic material can be achieved by HPLC using a chiral column or by a resolution using a resolving agent such as camphonic chloride as described by Thomas J. Tucker, et al., J. Med. Chem. 1994, 37, 2437-2444. A chiral compound may also be directly synthesized using a chiral catalyst or a chiral ligand, e.g. Mark A. Huffman, et al., J. Org. Chem. 1995, 60, 1590-1594.

As used herein, the term "alkyl" refers to a branched, unbranched, or cyclic hydrocarbon having, for example, from 1 to 30 carbon atoms, and often 1 to 12, or 1 to about 6 carbon atoms. Examples include, but are not limited to, methyl, ethyl, 1-propyl, 2-propyl, 1-butyl, 2-methyl-1-propyl, 2-butyl, 2-methyl-2-propyl (t-butyl), 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, hexyl, octyl, decyl, dodecyl, and the like. The alkyl can be unsubstituted or substituted. The alkyl can also be optionally partially or fully unsaturated. As such, the recitation of an alkyl group includes both alkenyl and alkynyl groups. The alkyl can be a monovalent hydrocarbon radical, as described and exemplified above, or it can be a divalent hydrocarbon radical (i.e., alkylene).

The term "alkenyl" refers to a monoradical branched or unbranched partially unsaturated hydrocarbon chain (i.e. a carbon-carbon, $sp^2$ double bond). In one embodiment, an alkenyl group can have from 2 to 10 carbon atoms, or 2 to 6 carbon atoms. In another embodiment, the alkenyl group has from 2 to 4 carbon atoms. Examples include, but are not limited to, ethylene or vinyl, allyl, cyclopentenyl, 5-hexenyl, and the like. The alkenyl can be unsubstituted or substituted.

The term "alkynyl" refers to a monoradical branched or unbranched hydrocarbon chain, having a point of complete unsaturation (i.e. a carbon-carbon, sp triple bond). In one embodiment, the alkynyl group can have from 2 to 10 carbon atoms, or 2 to 6 carbon atoms. In another embodiment, the alkynyl group can have from 2 to 4 carbon atoms. This term is exemplified by groups such as ethynyl, 1-propynyl, 2-propynyl, 1-butynyl, 2-butynyl, 3-butynyl, 1-hexynyl, 2-hexynyl, 3-hexynyl, 1-octynyl, and the like. The alkynyl can be unsubstituted or substituted.

The term "cycloalkyl" refers to cyclic alkyl groups of from 3 to 10 carbon atoms having a single cyclic ring or multiple condensed rings. Such cycloalkyl groups include, by way of example, single ring structures such as cyclopropyl, cyclobutyl, cyclopentyl, cyclooctyl, and the like, or multiple ring structures such as adamantanyl, and the like. The cycloalkyl can be unsubstituted or substituted. The cycloalkyl group can be monovalent or divalent, and can be optionally substituted as described above for alkyl groups. The cycloalkyl group can optionally include one or more cites of unsaturation, for example, the cycloalkyl group can include one or more carbon-carbon double bonds, such as, for example, cyclohexene, 1,3-cyclohexadiene, 1,4-cyclohexadiene, and the like.

The term "alkoxy" refers to the group alkyl-O—, where alkyl is as defined herein. In one embodiment, alkoxy groups include, e.g., methoxy, ethoxy, n-propoxy, iso-propoxy, n-butoxy, tert-butoxy, sec-butoxy, n-pentoxy, n-hexoxy, 1,2-dimethylbutoxy, and the like. The alkoxy can be unsubstituted or substituted.

As used herein, "aryl" refers to an aromatic hydrocarbon group derived from the removal of one hydrogen atom from a single carbon atom of a parent aromatic ring system. The radical can be at a saturated or unsaturated carbon atom of the parent ring system. The aryl group can have from 6 to 30 carbon atoms. The aryl group can have a single ring (e.g., phenyl) or multiple condensed (fused) rings, wherein at least one ring is aromatic (e.g., naphthyl, dihydrophenanthrenyl, fluorenyl, or anthryl). Typical aryl groups include, but are not limited to, radicals derived from benzene, naphthalene, anthracene, biphenyl, and the like. The aryl can be unsubstituted or optionally substituted, as described above for alkyl groups.

The term "halo" refers to fluoro, chloro, bromo, and iodo. Similarly, the term "halogen" refers to fluorine, chlorine, bromine, and iodine.

The term "haloalkyl" refers to alkyl as defined herein substituted by 1 or more halo groups as defined herein, which may be the same or different. In one embodiment, the haloalkyl can be substituted with 1, 2, 3, 4, or 5 halo groups. In another embodiment, the haloalkyl can by substituted with 1, 2, or 3 halo groups. The term haloalkyl also include perfluoro-alkyl groups. Representative haloalkyl groups include, by way of example, trifluoromethyl, 3-fluorododecyl, 12,12,12-trifluorododecyl, 2-bromooctyl, 3-bromo-6-chloroheptyl, 1H,1H-perfluorooctyl, and the like. The haloalkyl can be optionally substituted as described above for alkyl groups.

The term "heteroaryl" is defined herein as a monocyclic, bicyclic, or tricyclic ring system containing one, two, or three aromatic rings and containing at least one nitrogen, oxygen, or sulfur atom in an aromatic ring, and that can be unsubstituted or substituted, for example, with one or more, and in particular one to three, substituents, as described above in the definition of "substituted". Typical heteroaryl groups contain 2-20 carbon atoms in addition to the one or more heteroatoms. Examples of heteroaryl groups include, but are not limited to, 2H-pyrrolyl, 3H-indolyl, 4H-quinolizinyl, acridinyl, benzo[b]thienyl, benzothiazoly, β-carbolinyl, carbazolyl, chromenyl, cinnolinyl, dibenzo[b,d]furanyl, furazanyl, furyl, imidazolyl, imidizolyl, indazolyl, indolisinyl, indolyl, isobenzofuranyl, isoindolyl, isoquinolyl, isothiazolyl, isoxazolyl, naphthyridinyl, oxazolyl, perimidinyl, phenanthridinyl, phenanthrolinyl, phenarsazinyl, phenazinyl, phenothiazinyl, phenoxathiinyl, phenoxazinyl, phthalazinyl, pteridinyl, purinyl, pyranyl, pyrazinyl, pyrazolyl, pyridazinyl, pyridyl, pyrimidinyl, pyrimidinyl, pyrrolyl, quinazolinyl, quinolyl, quinoxalinyl, thiadiazolyl, thianthrenyl, thiazolyl, thienyl, triazolyl, tetrazolyl, and xanthenyl. In one embodiment the term "heteroaryl" denotes a monocyclic aromatic ring containing five or six ring atoms containing carbon and 1, 2, 3, or 4 heteroatoms independently selected from non-peroxide oxygen, sulfur, and N(Z) wherein Z is absent or is H, O, alkyl, aryl, or $(C_1-C_6)$alkylaryl. In another embodiment heteroaryl denotes an ortho-fused bicyclic heterocycle of about eight to ten ring atoms derived therefrom, particularly a benz-derivative or one derived by fusing a propylene, trimethylene, or tetramethylene diradical thereto.

The term "heterocycle" refers to a saturated or partially unsaturated ring system, containing at least one heteroatom selected from the group oxygen, nitrogen, and sulfur, and optionally substituted with one or more groups as defined herein under the term "substituted". A heterocycle can be a monocyclic, bicyclic, or tricyclic group containing one or more heteroatoms. A heterocycle group also can contain an oxo group (=O) or a thioxo (=S) group attached to the ring. Non-limiting examples of heterocycle groups include 1,3-dihydrobenzofuran, 1,3-dioxolane, 1,4-dioxane, 1,4-dithiane, 2H-pyran, 2-pyrazoline, 4H-pyran, chromanyl, imidazolidinyl, imidazolinyl, indolinyl, isochromanyl, isoindolinyl, morpholine, piperazinyl, piperidine, piperidyl, pyrazolidine, pyrazolidinyl, pyrazolinyl, pyrrolidine, pyrroline, quinuclidine, and thiomorpholine.

The term "heterocycle" can include, by way of example and not limitation, a monoradical of the heterocycles described in Paquette, Leo A.; *Principles of Modern Heterocyclic Chemistry* (W. A. Benjamin, New York, 1968), particularly Chapters 1, 3, 4, 6, 7, and 9; *The Chemistry of Heterocyclic Compounds, A Series of Monographs*" (John Wiley & Sons, New York, 1950 to present), in particular Volumes 13, 14, 16, 19, and 28; and *J. Am. Chem. Soc.* 1960, 82, 5566. In one embodiment, "heterocycle" includes a "carbocycle" as defined herein, wherein one or more (e.g. 1, 2, 3, or 4) carbon atoms have been replaced with a heteroatom (e.g. O, N, or S).

Examples of heterocycles, by way of example and not limitation, include, dihydroypyridyl, tetrahydropyridyl (piperidyl), thiazolyl, tetrahydrothiophenyl, sulfur oxidized tetrahydrothiophenyl, pyrimidinyl, furanyl, thienyl, pyrrolyl, pyrazolyl, piperidinyl, 4-piperidonyl, pyrrolidinyl, 2-pyrrolidonyl, pyrrolinyl, tetrahydrofuranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thienyl, thianthrenyl, pyranyl, isobenzofuranyl, chromenyl, xanthenyl, phenoxathinyl, 2H-pyrrolyl, isothiazolyl, isoxazolyl, pyrazinyl, pyridazinyl, indolizinyl, isoindolyl, 3H-indolyl, 1H-indazoly, purinyl, 4H-quinolizinyl, phthalazinyl, naphthyridinyl, quinoxalinyl, quinazolinyl, cinnolinyl, pteridinyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, isatinoyl, and bis-tetrahydrofuranyl.

By way of example and not limitation, carbon bonded heterocycles are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, 5-thiazolyl, and the like.

By way of example and not limitation, nitrogen bonded heterocycles can be bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline. In one embodiment, nitrogen bonded heterocycles include 1-aziridyl, 1-azetedyl, 1-pyrrolyl, 1-imidazolyl, 1-pyrazolyl, and 1-piperidinyl.

The term "carbocycle" refers to a saturated, unsaturated or aromatic ring having 3 to 8 carbon atoms as a monocycle, 7 to 12 carbon atoms as a bicycle, and up to about 30 carbon atoms as a polycycle. Monocyclic carbocycles typically have 3 to 6 ring atoms, still more typically 5 or 6 ring atoms. Bicyclic carbocycles have 7 to 12 ring atoms, e.g., arranged as a bicyclo [4,5], [5,5], [5,6] or [6,6] system, or 9 or 10 ring atoms arranged as a bicyclo [5,6] or [6,6] system. Examples of carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, phenyl, spiryl and naphthyl. The carbocycle can be optionally substituted as described above for alkyl groups.

The term "alkanoyl" or "alkylcarbonyl" refers to —C(=O)R, wherein R is an alkyl group as previously defined.

The term "acyloxy" or "alkylcarboxy" refers to —O—C(=O)R, wherein R is an alkyl group as previously defined. Examples of acyloxy groups include, but are not limited to, acetoxy, propanoyloxy, butanoyloxy, and pentanoyloxy. Any alkyl group as defined above can be used to form an acyloxy group.

The term "alkoxycarbonyl" refers to —C(=O)OR (or "COOR"), wherein R is an alkyl group as previously defined.

The term "amino" refers to —NH$_2$. The amino group can be optionally substituted as defined herein for the term "substituted". The term "alkylamino" refers to —NR$_2$, wherein at least one R is alkyl and the second R is alkyl or hydrogen. The term "acylamino" refers to N(R)C(=O)R, wherein each R is independently hydrogen, alkyl, or aryl.

The term "amino acid," includes a residue of a natural amino acid (e.g. Ala, Arg, Asn, Asp, Cys, Glu, Gln, Gly, His, Hyl, Hyp, Ile, Leu, Lys, Met, Phe, Pro, Ser, Thr, Trp, Tyr, and Val) in D or L form, as well as unnatural amino acids (e.g. phosphoserine, phosphothreonine, phosphotyrosine, hydroxyproline, gamma-carboxyglutamate; hippuric acid, octahydroindole-2-carboxylic acid, statine, 1,2,3,4,-tetrahydroisoquinoline-3-carboxylic acid, penicillamine, ornithine, citruline, α-methyl-alanine, para-benzoylphenylalanine, phenylglycine, propargylglycine, sarcosine, and tert-butylglycine). The term also comprises natural and unnatural amino acids bearing a conventional amino protecting group (e.g. acetyl or benzyloxycarbonyl), as well as natural and unnatural amino acids protected at the carboxy terminus (e.g. as a ($C_1$-$C_6$)alkyl, phenyl or benzyl ester or amide; or as an α-methylbenzyl amide). Other suitable amino and carboxy protecting groups are known to those skilled in the art (See for example, Greene, T. W.; Wutz, P. G. M., *Protecting Groups In Organic Synthesis*, 2$^{nd}$ edition, John Wiley & Sons, Inc., New York (1991) and references cited therein).

The term "peptide" describes a sequence of 2 to 35 amino acids (e.g. as defined hereinabove) or peptidyl residues. The sequence may be linear or cyclic. For example, a cyclic peptide can be prepared or may result from the formation of disulfide bridges between two cysteine residues in a sequence. Preferably a peptide comprises 3 to 20, or 5 to 15 amino acids. Peptide derivatives can be prepared as disclosed in U.S. Pat. Nos. 4,612,302; 4,853,371; and 4,684,620, or as described in the Examples herein below. Peptide sequences specifically recited herein are written with the amino terminus on the left and the carboxy terminus on the right.

The term "saccharide" refers to a sugar or other carbohydrate, especially a simple sugar. The saccharide can be a $C_6$-polyhydroxy compound, typically $C_6$-pentahydroxy, and often a cyclic glycal. The term includes the known simple sugars and their derivatives, as well as polysaccharides with two or more monosaccaride residues. The saccharide can include protecting groups on the hydroxyl groups, as described above in the definition of amino acids. The hydroxyl groups of the saccharide can be replaced with one or more halo or amino groups. Additionally, one or more of the carbon atoms can be oxidized, e.g., to keto or carboxyl groups.

The term "interrupted" indicates that another group is inserted between two adjacent carbon atoms (and the hydrogen atoms to which they are attached (e.g., methyl ($CH_3$), methylene ($CH_2$) or methine (CH))) of a particular carbon chain being referred to in the expression using the term "interrupted", provided that each of the indicated atoms' normal valency is not exceeded, and that the interruption results in a stable compound. Suitable groups that can interrupt a carbon chain include, e.g., with one or more non-peroxide oxy (—O—), thio (—S—), imino (—N(H)—), methylene dioxy (—OCH$_2$O—), carbonyl (—C(=O)—), carboxy (—C(=O)O—), carbonyldioxy (—OC(=O)O—), carboxylato (—OC(=O)—), imine (C=NH), sulfinyl (SO) and sulfonyl (SO$_2$). Alkyl groups can be interrupted by one or more (e.g., 1, 2, 3, 4, 5, or about 6) of the aforementioned suitable groups. The site of interruption can also be between a carbon atom of an alkyl group and a carbon atom to which the alkyl group is attached.

As to any of the above groups, which contain one or more substituents, it is understood, of course, that such groups do not contain any substitution or substitution patterns that are sterically impractical and/or synthetically non-feasible. In addition, the compounds of this invention include all stereochemical isomers arising from the substitution of these compounds.

Selected substituents within the compounds described herein are present to a recursive degree. In this context, "recursive substituent" means that a substituent may recite another instance of itself. Because of the recursive nature of such substituents, theoretically, a large number may be present in any given claim. One of ordinary skill in the art of medicinal chemistry and organic chemistry understands that the total number of such substituents is reasonably limited by the desired properties of the compound intended. Such properties include, by of example and not limitation, physical properties such as molecular weight, solubility or log P, application properties such as activity against the intended target, and practical properties such as ease of synthesis.

Recursive substituents are an intended aspect of the invention. One of ordinary skill in the art of medicinal and organic chemistry understands the versatility of such substituents. To the degree that recursive substituents are present in an claim of the invention, the total number will be determined as set forth above.

The term "linker" as used herein is a carbon chain that covalently attaches two chemical groups together and optionally can self-cleave or if covalently bonded to a substrate for an enzyme, may be cleaved by that enzyme or another molecule, which chain is optionally interrupted by one or more nitrogen atoms, oxygen atoms, carbonyl groups, (substituted) aromatic rings, or peptide bonds.

The term "luciferase," unless specified otherwise, refers to a naturally occurring or mutant luciferase. The luciferase, if naturally occurring, may be obtained easily by the skilled artisan from an organism. If the luciferase is one that occurs naturally or is a mutant, which retains activity in the luciferase-luciferin reaction, of a naturally occurring luciferase, it can be obtained readily from a culture of bacteria, yeast, mammalian cells, insect cells, plant cells, or the like, transformed to express a cDNA encoding the luciferase, or from an in vitro cell-free system for making the luciferase from a nucleic acid encoding the same. Luciferases are available from Promega Corporation (Madison, Wis.).

As used herein, a "bioluminogenic assay" or "bioluminogenic reaction" includes a reaction in which a product of a reaction between a nonluciferase enzyme and a derivative of 2-cyano-6-substituted benzothiazole in the presence of D-cysteine is a substrate for luciferase or a product of a nonenzymatic reaction having a derivative of 2-cyano-6-substituted benzothiazole in the presence of D-cysteine is a substrate for luciferase, which produces a measurable amount of light.

As used herein, "bioluminescence" is light produced as a result of a reaction between an enzyme and a substrate that generates light. Examples of such enzymes (bioluminescent enzymes) include firefly luciferase, click beetle luciferase, *Renilla* luciferase, cypridina luciferase, Aequorin photoprotein, obelin photoprotein and the like.

As used herein, a "bioluminogenic assay reagent" may include a substrate, as well as a cofactor(s) or other molecule(s) such as a protein, e.g., an enzyme, for a bioluminogenic reaction.

A "reaction mixture" may contain all reagents for a particular reaction, or may lack at least one of the reagents for the reaction. For example, a luciferase reaction mixture may contain reagents for the reaction except for a substrate for the luciferase, e.g., a reaction mixture useful to determine whether a test sample has a luciferase substrate. A reaction mixture for a nonluciferase enzyme may include all reagents for that reaction except for a molecule to be detected, e.g., the mixture contains all reagents except for a cofactor for the nonluciferase enzyme, and so the mixture is useful to detect the presence of the cofactor in a test sample.

For example, a reaction mixture for a luciferase-mediated reaction may contain reagents such a luciferin detection reagent (LDR) and optionally various inhibitors and/or surfactants. An LDR can provide a stable light signal proportional to the amount of luciferin or luciferin derivative present in the assay mixture. The reaction mixture can include reagents that, for example, control the pH of the reaction mixture, such as various buffers, and/or reagents that are inhibitors of a specific enzyme activity. A reaction mixture containing an LDR can include reagents, for example, as described in U.S. Publication No. 2004/0171099 (Cali et al.), which is incorporated herein by reference in its entirety. One skilled in the art will readily understand that various methods and aspects of the methods described in U.S. Publication No. 2004/0171099 may be used with the methods described herein, while other methods or aspects of the methods and reagents of U.S. Publication No. 2004/0171099 may be excluded from the methods described herein.

As used herein a "derivative of 2-cyano-6-substituted benzothiazole" is a molecule that is a substrate for a nonluciferase enzyme and yields a product that in the presence of D-cysteine is a bioluminogenic substrate of a luciferase, or is useful to detect molecules generated in nonenzymatic reactions. The derivatives of the invention may have one or more modifications to one or more of the rings of 2-cyano-6-substituted benzothiazole and/or substituents attached to one or more of the rings of 2-cyano-6-substituted benzothiazole. Examples include 2-cyano-6-substituted benzothiazoles with a 6-OH, to provide a substrate for a luciferase or a non-luciferase enzyme, or wherein a 6-O, or 6-N atom has a substituent that is a substrate for a luciferase or a non-luciferase enzyme. Further examples of 2-cyano-6-substituted benzothiazoles include compounds of the formulas described herein. In other embodiments, 2-cyano-benzothiazoles derivatives that are substituted at the 4-, 5-, or 7-position are provided and can be used in the methods of the invention.

II. Methods of the Invention

The invention provides methods for performing an assay for enzymes of interest using derivatives of 2-cyano-6-hydroxybenzothiazole or 2-cyano-6-aminobenzothiazole (derivatives of "2-cyano-6-substituted benzothiazole" hereinafter). The invention also provides novel compounds and compositions that can be used in an enzyme assay.

In one embodiment, the present invention provides derivatives of 2-cyano-6-substituted benzothiazole and methods for using such derivatives in enzyme activity assays or non-enzymatic biological assays, where the derivative serves as a substrate for a desired enzyme or reaction, and yields a product which in the presence of D-cysteine provides a bioluminogenic substrate for luciferase. Thus, by providing 2-cyano-6-substituted benzothiazole derivatives having a particular enzyme recognition site for a desired nonluciferase enzyme (a substrate) coupled to the 2-cyano-6-substituted benzothiazole backbone, e.g., coupled to the 6'-hydroxy site or a 6'-amino site, numerous nonluciferase enzymes may be detected in a bioluminescent assay, and/or their activity may be measured in a bioluminescent assay.

It is important to note that while some of the methods of the invention (for example, step b above) require an amount of D-cysteine, the D-cysteine need not be enantiomerically pure. In some embodiment, a racemic mixture of cysteine may be employed. In other embodiments, other mixtures of D- and L-cysteine may be employed, however it is advantageous to use substantially the same ratio of D- and L-cysteine in both the test and control reactions. For example, a racemic mixture of cysteine can provide about 50% the amount of light in a control reaction than would be obtained using exclusively D-cysteine. Even 50% of a maximum signal is readily detected and measured, and is well within the useful range of the assays.

Figure 2:
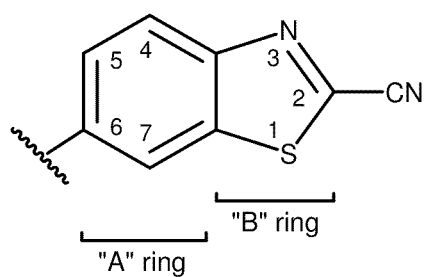
FIG. 2 illustrates the numbering of ring atoms of 2-cyano-6-substituted benzothiazole: the six membered "benzo" ring ("A ring"), and the five membered thiazole ring ("B ring") fuzed to the benzo ring.

Modifications of 2-cyano-6-substituted benzothiazole within the scope of the derivatives of the invention include one or more substitutions of a ring atom, one or more substitutions of a substituent (atom or group) attached to a ring atom, and/or addition of one or more atoms to the ring, e.g., expansion or addition of rings, or a combination thereof. Numbering for some of the ring atoms in 2-cyano-6-substituted benzothiazoles is shown in FIG. 2. 2-Cyano-6-hydroxybenzothiazole has two fused rings, a 6 membered ring having an OH group at position 6 (the "A ring" hereinafter), and a 5 membered ring (the "B ring" hereinafter), fused to the 6 membered ring, having a cyano group at the 2-position.

For instance, a 2-cyano-6-hydroxybenzothiazole derivative with an A ring modification may have a substitution of a carbon atom in the A ring with another atom, an addition of a ring, a substitution of a substituent attached to a ring atom with a different atom or group, or any combination thereof. A 2-cyano-6-hydroxy-benzothiazole derivative with a B ring modification may have an addition to or substitution of an atom in the five membered ring, e.g., insertion of one or more atoms, thereby expanding the ring, for instance, to a six membered ring, substitution of N or S in the ring with a different atom, e.g., a C or O, substitution of a substituent atom or group attached to a ring atom, or any combination thereof. In one embodiment, a derivative of the invention is one that is modified at more than one position, for instance, the derivative has two (or more) A ring modifications, two (or more) B ring modifications, or any combination thereof. In one embodiment, a modification can include the addition of a substituent on one of the rings of 2-cyano-6-hydroxybenzothiazole, wherein the substituent is a substrate for a nonluciferase enzyme, or a linker and a substrate for the nonluciferase enzyme.

In one embodiment, derivatives of 2-cyano-6-substituted benzothiazole are useful to detect nonluciferase enzymes, including P450 enzymes or monoamine oxidases (MAOs), or other enzymes such as N-acetyl transferases (NATs), flavin monoamine oxidases (FMOs), glutathione S transferases (GSTs), phosphatases, e.g., alkaline phosphatases (AP), sulfatases, or UDP-glucuronosyl transferase (UGT). For instance, exemplary derivatives with A ring modifications may be substrates for a reductase, such as a cytochrome P450 reductase, MAO, FMO, GST, dealkylase, deacetylase, deformylase, phosphatase, e.g., AP, sulfatase, beta-lactamase, alcohol dehydrogenase, protease, e.g., proteosome, cathepsin, calpain, beta secretase, thrombin, or granzyme, luciferase, or useful to detect reactive oxygen species (ROS), peroxidase, e.g., horseradish peroxidase (HRP), and/or redox conditions. Exemplary molecules or conditions to be detected with derivatives having at least a B ring modification include but are not limited to dealkylase, GST or luciferase, redox conditions, or UGT enzymes, or modulation (e.g., inhibition, or activation) of their activity. Exemplary molecules to be detected with those derivatives include a cytochrome P450 enzyme, esterase, e.g., acetylcholinesterase, OH radicals, demethylase, deacetylase, deformylase, or mycoplasma carboxypeptidase.

In one embodiment, derivatives of the invention have the following structure: L-X-M, wherein L may be a substrate for an enzyme or another molecule that interacts with the enzyme; X may be O, NR wherein R is an optionally substituted alkyl group or a nitrogen protecting group, NH, or a linker, e.g., a self-cleavable linker which spontaneously cleaves to yield M after L has been removed from L-X-M; and M may be 2-cyano-benzothiazole, optionally substituted with one or more substituents, e.g., as described herein.

The use of 2-cyano-6-substituted benzothiazole derivatives described herein can result in an assay that produces a measurable change in optical properties upon interaction with a nonluciferase molecule. As described herein, a 2-cyano-6-hydroxybenzothiazole derivative may include a substrate that includes a reactive chemical group for a nonluciferase enzyme linked to 2-cyano-6-hydroxybenzothiazole via a chemical linker. Transformation of the reactive chemical group of the derivative by the nonluciferase enzyme may yield a product that contains (retains) a portion of the substrate, a portion of the chemical linker, the chemical linker, or a portion of the substrate and the chemical linker, and that product in the presence of D-cysteine provides a bioluminogenic substrate for luciferase. Thus, bioluminescent methods that employ a 2-cyano-6-hydroxybenzothiazole derivative of the invention may be used to detect one or more molecules, e.g., an enzyme, a cofactor for an enzymatic reaction such as ATP, an enzyme substrate, an enzyme inhibitor, an enzyme activator, or OH radicals, or one or more conditions, e.g., redox conditions.

In one embodiment, a bioluminescent assay method to detect one or more nonluciferase enzymes is provided. The method includes contacting a sample suspected of having one or more nonluciferase enzymes, a substrate or a co-factor for the reaction, with a corresponding reaction mixture that includes a derivative of 2-cyano-substituted benzothizole having a substrate for the nonluciferase enzyme. In one embodiment, the derivative is one having a modification in the A ring that includes a substrate for the nonluciferase enzyme, e.g., for a cytochrome P450 enzyme. In another embodiment, the derivative is one having a modification to one of the rings that includes a substrate for the enzyme of interest, as well as a further modification to that ring or one or more of the other rings.

If a derivative of the invention in the presence of D-cysteine does not function directly as a substrate for luciferase, but the product of a reaction between the derivative and the nonluciferase enzyme in the presence of D-cysteine functions as a substrate for luciferase, sequential or concurrent reactions for the nonluciferase enzyme and the luciferase may be conducted. For instance, an assay for a nonluciferase enzyme that includes a 2-cyano-6-hydroxybenzothiazole derivative having a substrate for the nonluciferase enzyme, the product of which reaction in the presence of D-cysteine provides a bioluminogenic substrate for luciferase, may be conducted in a single reaction vessel and a beetle luciferase reaction mixture added to that vessel. D-cysteine may be present in the nonluciferase reaction mixture, the luciferase reaction mixture, added separately, or any combination thereof.

In another embodiment, a reaction mixture for a nonluciferase enzyme that includes a 2-cyano-6-hydroxybenzothiazole derivative having a substrate for the nonluciferase enzyme, the product of which reaction in the presence of D-cysteine provides a bioluminogenic substrate for luciferin, may be conducted in a single reaction vessel and a portion of that reaction added to a different vessel having a beetle luciferase reaction mixture. D-Cysteine may be present in the first reaction vessel, the second vessel, or both. Alternatively, the nonluciferase and luciferase reactions may be conducted simultaneously in the same vessel.

The invention thus provides in an embodiment a method to detect or determine the presence or amount of a molecule for a nonluciferase enzyme-mediated reaction in a sample. The method includes contacting a sample, a first reaction mixture for a nonluciferase enzyme-mediated reaction, and a derivative of 2-cyano-6-substituted benzothiazole which includes a substrate for the nonluciferase enzyme, so as to yield a first mixture. The first mixture includes a product produced by a reaction between the nonluciferase enzyme and the derivative. The product in the presence of D-cysteine is a bioluminogenic substrate for a luciferase. In one embodiment, the derivative is a compound of Formula I. In another embodiment, the derivative is a compound of Formula II. In yet another embodiment, the derivative is a compound of another formula described herein. At least a portion of the first mixture is contacted with a second reaction mixture for a luciferase-mediated reaction, so as to yield a second mixture.

The first mixture, the second mixture, or both, may include D-cysteine. Then luminescence in the second reaction is detected or determined (e.g., quantified), thereby detecting or determining the presence or amount of a molecule for the nonluciferase enzyme-mediated reaction in the sample, e.g., compared to a control.

In an alternate embodiment, a method to detect or determine the presence or amount of a molecule for a first nonluciferase enzyme-mediated reaction in a sample is provided. The method includes contacting a sample, a reaction mixture for a nonluciferase-mediated enzyme reaction and a luciferase-mediated reaction, and a derivative of 2-cyano-6-substituted benzothiazole having a substrate for the nonluciferase enzyme, yielding a mixture. D-Cysteine may be present in the sample, the reaction mixture for the nonluciferase enzyme, the reaction mixture for the luciferase, or any combination thereof. A reaction between the nonluciferase enzyme and the derivative yields a product that in the presence of D-cysteine is a luminogenic substrate for the luciferase. Luminescence in the mixture is detected or determined, thereby detecting or determining the presence or amount of a molecule for the nonluciferase-mediated reaction in the sample.

In one embodiment, the invention includes providing a mixture having a sample, a first reaction mixture for a nonluciferase enzyme-mediated reaction, and a derivative of 2-cyano-6-substituted benzothiazole which includes a substrate for the nonluciferase enzyme. A reaction between the nonluciferase enzyme and the derivative yields a product that in the presence of D-cysteine is a bioluminogenic substrate for a beetle luciferase. At least a portion of the first mixture is contacted with a second reaction mixture for a beetle luciferase-mediated reaction which includes D-cysteine, so as to yield a second mixture. Luminescence in the second mixture is detected or determined, thereby detecting or determining the presence or amount of a molecule for the nonluciferase enzyme-mediated reaction in the sample.

In another embodiment, the method includes providing a mixture having a sample, a reaction mixture for a nonluciferase enzyme-mediated reaction and a beetle luciferase-mediated reaction which includes D-cysteine, and a derivative of 2-cyano-6-substituted benzothiazole which includes a substrate for the nonluciferase enzyme. A reaction between the nonluciferase enzyme and the derivative yields a product that in the presence of D-cysteine is a bioluminogenic substrate for the beetle luciferase. Luminescence in the mixture is detected or determined, thereby detecting or determining the presence or amount of a molecule for the nonluciferase enzyme-mediated reaction in the sample.

In yet another embodiment, the method includes providing a mixture having a sample which includes D-cysteine, a reaction mixture for a nonluciferase enzyme-mediated reaction and a beetle luciferase-mediated reaction and a derivative of 2-cyano-6-substituted benzothiazole which includes a substrate for the nonluciferase enzyme. A reaction between the nonluciferase enzyme and the derivative yields a product that in the presence of D-cysteine is a bioluminogenic substrate for the beetle luciferase. Luminescence in the mixture is detected or determined, thereby detecting or determining the presence or amount of a molecule for the nonluciferase enzyme-mediated reaction in the sample.

The invention also provides an embodiment directed to a method to detect the presence or amount of a non-enzymatic molecule in a sample. The method includes contacting a sample, a first reaction mixture for a nonenzyme-mediated reaction and a derivative of 2-cyano-6-substituted benzothiazole which in the presence of the molecule yields a product.

The product in the presence of D-cysteine is a bioluminogenic substrate for a luciferase. At least a portion of the first reaction and a second reaction mixture for a luciferase-mediated reaction are contacted, to yield a second reaction. Then luminescence in the second reaction is detected or determined, thereby detecting or determining the presence or amount of the molecule.

Also provided is a method to identify a modulator of a nonluciferase enzyme-mediated reaction. The method includes contacting one or more agents, a first reaction mixture for a nonluciferase enzyme-mediated reaction, and a derivative of 2-cyano-6-substituted benzothiazole having a substrate for the nonluciferase enzyme, so as to yield a first mixture, or providing such a mixture. The first mixture, in the absence of the one or more agents, includes a product produced by a reaction between the nonluciferase enzyme and the derivative that in the presence of D-cysteine is a bioluminogenic substrate for a beetle luciferase. At least a portion of the first mixture and a second reaction mixture for a beetle luciferase-mediated reaction are mixed, so as to yield a second mixture. D-Cysteine may be present in the one or more agents, first reaction mixture, second reaction mixture, or any combination thereof. Luminescence in the second mixture is compared with a control mixture, thereby identifying whether one or more of the agents modulates the nonluciferase enzyme-mediated reaction.

The invention therefore provides a bioluminogenic method which employs a derivative of 2-cyano-6-substituted benzothiazole to detect one or more molecules, e.g., an enzyme, a cofactor for an enzymatic reaction such as ATP, an enzyme substrate, an enzyme inhibitor, an enzyme activator, or OH radicals, or one or more conditions, e.g., redox conditions. The invention thus provides for bioluminogenic assays to detect the amount, activity or presence of a molecule in a sample.

The methods may be used, for example, to determine the presence or amount of at least one molecule, e.g., a nonluciferase enzyme, a regulator of a nonluciferase enzyme, a nonluciferase enzyme substrate, and/or cofactors of the reaction, or a condition in a sample including but not limited to an animal, e.g., vertebrate, physiological fluid, e.g., blood, plasma, urine, mucous secretions and the like, a cell, cell lysate, cell supernatant, or purified fraction of a cell (e.g., a subcellular fraction). In one embodiment, the methods according to the present invention provide a rapid method for detecting one or more molecules in a single sample such as an aliquot of cells or a lysate thereof. In one embodiment, the method includes quantifying the presence, amount or specific activity of a molecule such as an enzyme, substrate or cofactor in a bioluminogenic assay. The intensity of the bioluminogenic signal is a function of the presence or amount of the respective molecule. In addition, the reaction may contain one or more test agents, e.g., enzyme inhibitors or activators, and/or different concentrations of inhibitors or activators. In one embodiment, the method employs at least two different reactions, where the first reaction is a nonluciferase enzyme-mediated reaction and the second reaction is a beetle luciferase-mediated reaction. In another embodiment, the first reaction is a nonenzymatic reaction and the second reaction is a beetle luciferase-mediated reaction. In yet another embodiment, the method employs a single reaction, e.g., a beetle luciferase-mediated reaction or a fluorogenic reaction.

Thus, a bioluminogenic assay may directly or indirectly detect, e.g., measure, the amount, presence or specific activity of, for example, a cofactor for an enzyme-mediated reaction, an enzyme, an enzyme substrate, an inhibitor of the enzyme, an activator of the enzyme, or a condition. For instance, in one embodiment, a derivative of 2-cyano-6-hydroxybenzothiazole which is a substrate for a nonluciferase enzyme, for instance, a derivative which is a substrate of a monoamine oxidase, yields a product which in the presence of D-cysteine is a substrate for a beetle luciferase, and so may be employed in a bioluminogenic assay to detect the oxidase. In some embodiments, the derivative includes a substrate for a nonluciferase enzyme or is useful to detect another molecule, and in the presence of D-cysteine is a substrate for luciferase which yields a substantial amount of light.

In one embodiment, the invention provides a bioluminescent assay method to detect one or more nonluciferase enzymes. The method includes contacting a sample suspected of having one or more nonluciferase enzymes, or a substrate or a co-factor for the nonluciferase-mediated reaction, with a corresponding reaction mixture that includes a derivative of 2-cyano-6-hydroxybenzothiazole that is a substrate for the nonluciferase enzyme. In one embodiment, the derivative is one having a modification in the A ring that includes a recognition site for the nonluciferase enzyme, e.g., for a phosphatase. In another embodiment, the derivative is one having a modification in the B ring which includes a substrate for a nonluciferase enzyme. In another embodiment, the derivative is one having a modification in one of the rings that includes a recognition site for the enzyme of interest, as well as a further modification in that ring or one or more of the other rings.

The invention thus provides a method to detect or determine the presence or amount of a molecule for a nonluciferase enzyme-mediated reaction in a sample. The method includes contacting a sample, a first reaction mixture for a nonluciferase enzyme-mediated reaction, and a derivative of 2-cyano-6-substituted benzothiazole in the presence of D-cysteine which includes a substrate for the nonluciferase enzyme, so as to yield a first mixture or providing such a first mixture comprising a bioluminogenic product that in the presence of D-cysteine is a substrate for a luciferase, or providing such a first mixture. In one embodiment, the derivative is a compound of formula I. In another embodiment, the derivative is a compound of formula II, formula XV, or any other formula described herein. At least a portion of the first mixture is contacted with a second reaction mixture for a beetle luciferase-mediated reaction, so as to yield a second mixture. Then luminescence in the second mixture is detected or determined, thereby detecting or determining the presence or amount of a molecule for the nonluciferase enzyme-mediated reaction in the sample.

Further provided is a method to detect or determine the presence or amount of a molecule for a nonluciferase enzyme-mediated reaction in a sample. The method includes contacting a sample, a reaction mixture for a nonluciferase-mediated enzyme reaction and for a luciferase-mediated reaction, and a derivative of 2-cyano-6-substituted benzothiazole which has a substrate for the nonluciferase enzyme, yielding a mixture. A reaction between the nonluciferase enzyme and the derivative yields a luminogenic product that in the presence of D-cysteine is a substrate for the luciferase. In one embodiment, the derivative is a compound of formula I. In another embodiment, the derivative is a compound of formula II, formula XV, or any other formula described herein. Luminescence in the mixture is detected or determined, thereby detecting or determining the presence or amount of a molecule for the nonluciferase-mediated reaction in the sample.

The invention also provides a method to detect the presence or amount of a molecule in a sample. The method includes contacting a sample, a first reaction mixture for a nonenzyme-mediated reaction and a derivative of 2-cyano-6-substituted benzothiazole which in the presence of the molecule yields a luminogenic product that in the presence of D-cysteine is a substrate for a luciferase, and then contacting at least a portion of the first reaction and a second reaction mixture for a luciferase-mediated reaction, to yield a second reaction. Luminescence in the second reaction is detected or determined, thereby detecting or determining the presence or amount of the molecule. For instance, a mixture is provided having a sample, a first reaction mixture for a nonenzyme-mediated reaction and a derivative of 2-cyano-6-substituted benzothiazole which in the presence of the molecule yields a luminogenic product that in the presence of D-cysteine is a substrate for a beetle luciferase. At least a portion of the first mixture and a second reaction mixture for a beetle luciferase-mediated reaction are mixed, to yield a second mixture, and then luminescence in the second mixture is detected or determined, thereby detecting or determining the presence or amount of the molecule.

For the biolumingenic assays described herein which employ derivatives with a lower background, those assays can use lower (or higher) amounts of the derivative, and those derivatives may have improved reactivity, e.g., with a nonluciferase enzyme. In addition, for any of the bioluminogenic assays described herein, other reagents may be added to reaction mixtures, including but not limited to those that inhibit or prevent inactivation of luciferase, or otherwise extend or enhance luminescent signal.

Also provided is a method to identify or measure the potency of a modulator of a nonluciferase enzyme-mediated reaction. The method includes contacting one or more agents, a first reaction mixture for a nonluciferase enzyme-mediated reaction, and a derivative of 2-cyano-6-substituted benzothiazole having a substrate for the nonluciferase enzyme, so as to yield a first mixture, or providing such a mixture, wherein the derivative includes an A or B ring modification relative to 2-cyano-6-hydroxybenzothiazole. The first mixture in the absence of the one or more agents includes a luminogenic product that in the presence of D-cysteine is a substrate for a beetle luciferase. At least a portion of the first mixture and a second reaction mixture for a beetle luciferase-mediated reaction are mixed, so as to yield a second mixture. Luminescence in the second mixture is compared with a control mixture, thereby identifying whether one or more of the agents modulates the nonluciferase enzyme-mediated reaction and/or to what extent and with what potency.

In one embodiment of the invention, test compounds can be screened and evaluated for their activities as substrates or cofactors of, or regulators, either inhibitors or activators, of an enzymatic or nonenzymatic reaction by using the 2-amino-6-substituted benzothiazole derivatives of the present invention. A candidate compound may be determined to be regulator or a substrate of a reaction by contacting a reaction mixture with a derivative and the test compound, under conditions that would, in the absence of the test compound, yield bioluminescence, or a bioluminogenic product.

In one aspect of the invention, a method is provided to distinguish between a substrate and an inhibitor of a reaction. For example, the compound is incubated with at least one enzyme under conditions which allow for metabolism of the compound prior to providing a 2-cyano-6-substituted benzothiazole derivative under conditions that, in the absence of an inhibitor or substrate of the enzyme, would be suitable for interaction between the derivative and the enzyme. In one embodiment, the product of that reaction in the presence of D-cysteine is a substrate of luciferase and in the presence of luciferase yields a light emitting second reaction. The resulting light emitting reaction is compared to the one obtained from contacting the enzyme with the compound and the derivative, under conditions that would, in the absence of an inhibitor of the enzyme, be suitable for interaction between the derivative and the enzyme. Metabolism of the compound by the enzyme reduces its concentration in the assay medium and may lead to an apparent loss of inhibitory activity compared to conditions without metabolism of the compound which would indicate it was a substrate for the enzyme. An inhibitory compound that was not metabolized would show equal potency, irrespective of the time of addition of the substrate.

In one aspect of the invention, the compound is preferably contacted first with the enzyme for a first predetermined time period. Thereafter, the mixture is contacted with a 2-cyano-6-substituted benzothiazole derivative and bioluminescent enzyme, e.g., luciferase, simultaneously or contemporaneously, and the mixture is allowed to incubate for a second predetermined time period.

In another aspect of the invention, the compound is incubated with the enzyme for a first predetermined time period to form a first mixture. Thereafter, the first mixture is contacted with the 2-cyano-6-substituted benzothiazole derivative, to form a second mixture that is allowed to incubate for a second predetermined time period. The second mixture is then contacted with a bioluminescent enzyme, e.g., luciferase, to form a third mixture, which is allowed to incubate for a third predetermined time period. Thereafter, the activity resulting from the interaction of the enzyme with the compound in the presence of D-cysteine is determined by measuring luminescence during and/or after the third predetermined time period relative to a control (e.g., no compound) reaction. In this way, for example, mechanism based inhibitors of the first enzyme can be identified and distinguished from nonmechanism based inhibitors because the first incubation with the test compound but without the luciferin derivative will lead to a more profound inhibition by a mechanism based inhibitor than would be observed without the first incubation of substrates of the first reaction will show reduced inhibition.

In another embodiment of the invention, a cell-based method is provided for screening a compound to determine its effect on enzyme activity of the cell. The test compound is contacted with a cell having the enzyme, either naturally or via recombinant expression, the 2-cyano-6-substituted benzothiazole derivative, and bioluminescent enzyme, e.g., luciferase, or contacted with a cell having the enzyme and luciferase, and the 2-cyano-6-substituted benzothiazole derivative, for a predetermined period of time. Thus, in one embodiment, a cell that either transiently or stably expresses a recombinant enzyme such as a bioluminescent enzyme, e.g., luciferase, may be employed. Any conventional method for creating transient or stable transfected cells may be used. In one embodiment, a 2-cyano-6-substituted benzothiazole derivative is contacted with and diffuses into a cell and, if the appropriate molecule is present, yields a product, which is a substrate for luciferase. If a luciferase is present in the cell, luminescence can be detected. Alternatively, in a cell which lacks luciferase, the product passes out of the cell into the medium and that medium is added to a luciferase reaction mixture. Thereafter, the activity resulting from the interaction of the cell with the compound is determined by measuring luminescence of the reaction mixture relative to a control (minus test compound) reaction mixture.

In one aspect of the invention, the compound is preferably contacted first with the cell for a predetermined time period. Thereafter, the cell is contacted with the 2-cyano-6-substituted benzothiazole derivative and luciferase simultaneously or contemporaneously and the mixture allowed to incubate for a second predetermined time period. Enzyme activity is determined by measuring the amount of luminescence generated from the reaction mixture relative to a control reaction mixture (e.g., minus test compound). In another aspect of the invention, the test compound is preferably contacted first with the cell for a predetermined time period. Thereafter, the exposed cell is then contacted with the 2-cyano-6-substituted benzothiazole derivative and incubated for a second predetermined time period. The cell is then contacted with luciferase to form a third mixture which is allowed to incubate for a third predetermined time period. Thereafter, the activity of the cell resulting from the interaction of the cell with the test compound(s) is determined by measuring luminescence of the reaction mixture relative to a control reaction mixture (e.g., minus test compound). Detergent addition can rupture the cells and release cell content.

A cell-based luminescence detection assay for molecules present in the cell medium, e.g., molecules which actively or via inactive mechanisms are present in the cell medium, can include adding a reaction mixture with the 2-cyano-6-substituted benzothiazole derivative to the cell medium, or adding the cell medium to a reaction mixture with the 2-cyano-6-substituted benzothiazole derivative, and detecting luminescence.

In yet another embodiment of the cell-based assay of the invention, the cells may be lysed in an appropriate lysis buffer. For animal cells, a buffer with 0.1-1.0% non-ionic detergents such as Triton X100 or Tergitol is typically sufficient. Bacteria, plant, fungal or yeast cells are usually more difficult to lyse. Detergents, freeze/thaw cycles, hypotonic buffers, sonication, cavitation or combinations of these methods may be used. The method of lysis that produces a lysate is compatible with luciferase or other enzyme activity, or the detection of other molecules or conditions.

The presence or activity of nonluciferase enzymes may be measured in cells grown in culture medium or in cells within animals, e.g., living animals. For measurements in cells in animals, a 2-cyano-6-substituted benzothiazole derivative may be administered to the animal, e.g., injected into the animal or added to an aqueous solution, e.g., water, or food consumed by the animal. Conversion of the derivative to a product that is a luciferase substrate may be detected by luminescence mediated by luciferase expressed in cells in the animal, e.g., transgenic cells, by luciferase administered to the animal, e.g., injected into the animal, or by collecting physiological fluids, e.g., blood, plasma, urine, and the like, or tissue samples, and combining those with a luciferase reagent.

Assays which employ two reactions may be conducted simultaneously (one step) or sequentially (two step) to detect one or more moieties including proteins (peptides or polypeptides), e.g., enzymes, substrates, cofactors, inhibitors or activators for enzymatic reactions, or conditions, e.g., redox conditions. A sequential reaction may be conducted in the same vessel, e.g., a well of a multiwell plate. For a two step assay, the first reaction mixture may contain all of the reagents or less than all of the reagents for a nonluciferase enzyme-mediated reaction, where one of the reagents that is absent is the one to be detected in a sample, e.g., a cell lysate. For instance, a nonluciferase enzyme-mediated reaction is performed under conditions effective to convert a 2-cyano-6-substituted benzothiazole derivative that has a substrate for the nonluciferase to a product that in the presence of D-cysteine is a substrate of luciferase. The first reaction may be quenched at the time, or prior to addition, of a luciferase reaction mixture. For instance, a quencher of the first reaction may be present in the luciferase reaction mixture. The luciferase reaction mixture preferably substantially lacks a substrate for the luciferase, e.g., the only source of substrate for the luciferase is provided by a reaction between the nonluciferase enzyme and the derivative. When all the reagents for the first reaction are present in the first reaction mixture, the assay may be employed to identify moieties that alter the reaction, e.g., inhibitors or enhancers of the reaction. After performing the reactions, either simultaneously or sequentially, the presence or amount of one or more molecules, or one or more inhibitors or activators of the reaction(s) is/are detected or determined and/or to what extent and with what potency.

For a one step assay, a reaction mixture may contain reagents for two reactions, such as reagents for a nonluciferase enzyme-mediated reaction and a luciferase-mediated reaction or for a nonenzymatic reaction and a luciferase-mediated reaction, or a reaction mixture for a single reaction.

For assays which employ two reactions, the order of adding the molecules for the assays can vary. If initiated and conducted sequentially (whether in the same vessel or not), adjustments to reaction conditions, e.g., reagent concentration, temperatures or additional reagents, may be performed. For instance, a quenching agent or enhancing agent may be added between reactions (see, e.g., U.S. Pat. No. 5,744,320 (Sheri et al.) and U.S. Pat. No. 6,586,196 (Bronstein et al.), the disclosures of which are specifically incorporated by reference herein). In one embodiment, the two or more reactions are carried out simultaneously in a single reaction mixture. Optionally, the assays are a homogeneous assay, e.g., the components are mixed prior to adding the mixture to the sample. Results may be read without additional transfer of reagents.

The assays of the present invention thus allow the detection of one or more molecules or conditions in a sample, e.g., a sample which includes eukaryotic cells, e.g., yeast, avian, plant, insect or mammalian cells, including but not limited to human, simian, murine, canine, bovine, equine, feline, ovine, caprine or swine cells, or prokaryotic cells, or cells from two or more different organisms, or cell lysates or supernatants thereof, or a sample which includes a purified form of the molecule, e.g., purified nonluciferase enzyme which is useful to prepare a standard curve. The cells may not have been genetically modified via recombinant techniques (nonrecombinant cells), or may be recombinant cells which are transiently transfected with recombinant DNA and/or the genome of which is stably augmented with a recombinant DNA, or which genome has been modified to disrupt a gene, e.g., disrupt a promoter, intron or open reading frame, or replace one DNA fragment with another. The recombinant DNA or replacement DNA fragment may encode a molecule to be detected by the methods of the invention, a moiety which alters the level or activity of the molecule to be detected, and/or a gene product unrelated to the molecule or moiety that alters the level or activity of the molecule.

The present methods can be employed to detect a molecule for an enzyme-mediated reaction, a nonenzymatic-mediated reaction or condition. For instance, molecules or conditions to be detected by the method include but are not limited to enzymes, e.g., demethylases, oxidases (e.g., a MAO), deacetylases, deformylases, proteases (proteosome, calpain, beta-secretase, cathepsin, calpain, thrombin, granzyme B), phosphatases, kinases, peroxidases, transferases, e.g., GST or UGT, sulfotases, beta-lactamases, cytochrome P450 enzymes, esterase, e.g., acetylcholinesterase, dehydrogenase, luciferase, substrates, inhibitors, co-factors, activators of enzyme mediated reactions, reactive oxygen species, reducing conditions and transcriptional regulators or regulators of gene transcription. The enzymes employed in the methods, either enzymes to be detected or enzymes which are useful to detect a substrate or cofactor, can be selected from any combination of enzymes including recombinant and endogenous (native) enzymes. In one embodiment, the enzyme to be detected is an endogenous enzyme. In another embodiment, the enzyme is a recombinant enzyme. Other combinations apparent to one of ordinary skill in the art can be used in the present assays and methods according to the teachings herein. The enzymes include but are not limited to proteases, phosphatases, peroxidases, sulfatases, peptidases, oxidases, dealkylases, deformylases, transferases, and glycosidases. The enzyme may be a hydrolase, oxidoreductase, lyase, transferase, e.g., glutathione S transferase or UDP glucuronosyltransferase, isomerase, ligase, or synthase. Of particular interest are classes of enzymes that have physiological significance. These enzymes include protein peptidases, esterases, protein phosphatases, glycosylases, proteases, dehydrogenases, oxidases, oxygenases, reductases, methylases, transferases and the like. Enzymes of interest include those involved in making or hydrolyzing esters, both organic and inorganic, glycosylating, and hydrolyzing amides. In any class, there may be further subdivisions.

In particular, enzymes that are useful in the present invention include any protein that exhibits enzymatic activity, e.g., lipases, phospholipases, sulphatases, ureases, peptidases, proteases and esterases, including acid phosphatases, glucosidases, glucuronidases, galactosidases, carboxylesterases, and luciferases. In one embodiment, the enzyme is a hydrolytic enzyme. Examples of hydrolytic enzymes include alkaline and acid phosphatases, esterases, decarboxylases, phospholipase D, P-xylosidase, β-D-fucosidase, thioglucosidase, β-D-galactosidase, α-D-galactosidase, α-D-glucosidase, β-D-glucosidase, β-D-glucuronidase, α-D-mannosidase, β-D-mannosidase, β-D-fructofuranosidase, and β-D-glucosiduronase.

With respect to the methods described above, some embodiments provide a first mixture that includes a product produced by a reaction between the nonluciferase enzyme and the derivative, wherein the product in the presence of D-cysteine a bioluminogenic substrate for a luciferase. The invention also provides reciprocal methods wherein a first mixture that includes a product produced by a reaction between the nonluciferase enzyme and the derivative, wherein the product in the presence of D-cysteine a not bioluminogenic substrate for a luciferase. For example, in various embodiments, a nonluciferase enzyme can consume a luciferase pro-substrate (e.g., the derivative), rather than generate a luciferase substrate. By comparing the test reaction to a control, the method provides the ability to detect or determine enzyme activity, or to determine the activity of a modulator for enzyme activity.

III. Examples of Derivatives

In one embodiment, the invention provides a compound of Formula IA:

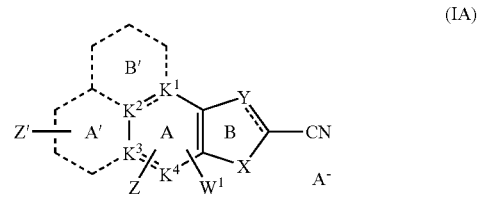

(IA)

wherein
Y is N,N-oxide, N—($C_1$-$C_6$)alkyl, or CH;
X is S, O, CH=CH, N=CH, or CH=N;
Z and Z' are independently H, OR, NHR, or NRR;
$W^1$ and Z are both keto groups on ring A, and at least one of the dotted lines denoting optional double bonds in ring A is absent;
each of $K^1$, $K^2$, $K^3$, and $K^4$ are independently CH, N,N-oxide, or N—($C_1$-$C_6$)alkyl, and the dotted lines between $K^1$ and $K^2$, and $K^3$ and $K^4$, denote optional double bonds;
A' and B' are optional aromatic rings fused to ring A, only one of which is present in the compound, so as to form a fused tricyclic system; and
when B' is present, the group Z is present, and
when A' is present, the group Z is absent; and
the dotted line in ring B is an optional double bond;
each R is independently H, ($C_1$-$C_{20}$)alkyl, ($C_2$-$C_{20}$)alkenyl, ($C_2$-$C_{20}$)alkynyl, ($C_3$-$C_{20}$)cycloalkyl, ($C_1$-$C_{12}$)alkoxy, ($C_6$-$C_{30}$)aryl, heteroaryl, heterocycle, ($C_1$-$C_{20}$)alkylsulfoxy, ($C_6$-$C_{30}$)arylsulfoxy, heteroarylsulfoxy, ($C_1$-$C_{20}$)alkylsulfonyl, ($C_6$-$C_{30}$)arylsulfonyl, heteroaryl-sulfonyl, ($C_1$-$C_{20}$) alkylsulfinyl, ($C_6$-$C_{30}$)arylsulfinyl, heteroarylsulfinyl, ($C_1$-$C_{20}$)alkoxycarbonyl, amino, NH($C_1$-$C_6$)alkyl, N(($C_1$-$C_6$)alkyl)$_2$, tri($C_1$-$C_{20}$)ammonium($C_1$-$C_{20}$)alkyl, heteroaryl($C_1$-$C_{20}$)alkyl, heteroaryl having quaternary nitrogen, heteroarylcarbonyl having quaternary nitrogen, ($C_6$-$C_{30}$)arylthio, ($C_1$-$C_{20}$)alkylphosphate, ($C_1$-$C_{20}$)alkylphosphonate, ($C_6$-$C_{30}$)arylphosphate, ($C_6$-$C_{30}$)arylphosphonate, phosphate, sulfate, saccharide, or $M^+$, wherein M is an alkali metal;
or when Z or Z' is $NR^1R^1$, $R^1R^1$ together with the N to which they are attached forms a heteroaryl or heterocycle group;
wherein any alkyl, alkenyl, alkynyl, cycloalkyl, alkoxy, amino, aryl, heteroaryl, or heterocycle group is optionally substituted with 1, 2, 3, 4, or 5 substituents selected from ($C_1$-$C_{20}$)alkyl, ($C_2$-$C_{20}$)alkenyl, ($C_2$-$C_{20}$)alkynyl, ($C_3$-$C_{20}$)cycloalkyl, ($C_1$-$C_{20}$)alkoxyl, ($C_1$-$C_{20}$)alkylcarbonyl, ($C_1$-$C_{20}$)alkylcarboxyl, halo, hydroxyl, —$COOR^x$, —$SO_2R^x$, —$SO_3R^x$, nitro, amino, ($C_1$-$C_{20}$)alkyl-S(O)—, ($C_1$-$C_{20}$)alkyl-$SO_2$—, phosphate, ($C_1$-$C_{20}$)alkylphosphate, ($C_1$-$C_{20}$)alkylphosphonate, NH($C_1$-$C_6$)alkyl, NH($C_1$-$C_6$)alkynyl, N(($C_1$-$C_6$)alkyl)$_2$, N(($C_1$-$C_6$)alkynyl)$_2$, mercapto, ($C_1$-$C_{20}$)alkylthio, ($C_6$-$C_{30}$)aryl, ($C_6$-$C_{30}$)arylthio, trifluoromethyl, =O, heteroaryl, and heterocycle, and each substituent is optionally substituted with one to three R groups;
$R^x$ is H, ($C_1$-$C_6$)alkyl, or ($C_6$-$C_{30}$)aryl;
when Z or Z' comprises a nitrogen moiety, one or both of the hydrogens of the Z or Z' nitrogen moiety may be replaced by ($C_1$-$C_{20}$)alkyl or the group L, wherein L is an amino acid radical, a peptide radical having up to 20 amino acid moieties, or any other small molecule that is a substrate for a nonluciferase;
when Z is a hydroxyl group or a nitrogen moiety, H of the hydroxyl or nitrogen moiety may be replaced by $(HO)_2P(O)$—$OCH_2$—, sulfo, —$PO_3H_2$, or by a cephalosporanic acid attached to the group Z via a carbon chain of one to about 12 carbon atoms;
when Z or Z' is a hydroxyl group or a nitrogen moiety, one H of the hydroxyl or nitrogen moiety may be replaced by the group L'-linker, wherein L' is a group removable by an enzyme to free the linker, and linker is a carbon chain that can self-cleave, optionally interrupted by one or more nitrogen atoms, oxygen atoms, carbonyl groups, optionally substituted aromatic rings, or peptide bonds, linker is attached to L' via an oxygen atom or an NH group at one terminus of the linker and the other terminus of the linker forms an ether, ester, or amide linkage with a group Z or Z';
when Z is OR, formula I is optionally a dimer connected at the two A rings via a linker comprising a ($C_1$-$C_{12}$)alkyl diradical that is optionally interrupted by one to four O atoms, N atoms, or an optionally substituted aryl, heteroaryl, or heterocycle group to form a bridge between the dimer of formula I, and the R group of each Z group connecting the dimer of formula I is replaced by the bridge;
$A^-$ is an anion, present when a quaternary nitrogen is present; or a salt thereof.

In another embodiment, the invention provides a compound of Formula I, which is a compound of Formula IAA:

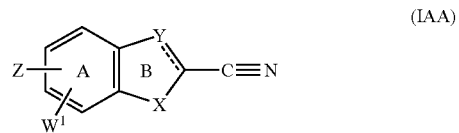

(IAA)

wherein
Y is N,N-oxide, N—($C_1$-$C_6$)alkyl, or CH;
X is S, O, CH=CH, N=CH, or CH=N;
Z is H, OR, NHR, or NRR;
$W^1$ is H, halo, hydroxyl, ($C_1$-$C_6$)alkyl, or ($C_1$-$C_6$)alkoxy;
the dotted line in ring B is an optional double bond;
each R is independently H, ($C_1$-$C_{20}$)alkyl, ($C_2$-$C_{20}$)alkenyl, ($C_2$-$C_{20}$)alkynyl, ($C_3$-$C_{20}$)cycloalkyl, ($C_1$-$C_{12}$)alkoxy, ($C_6$-$C_{30}$)aryl, heteroaryl, heterocycle, ($C_1$-$C_{20}$)alkylsulfoxy, ($C_6$-$C_{30}$)arylsulfoxy, heteroarylsulfoxy, ($C_1$-$C_{20}$)alkylsulfonyl, ($C_6$-$C_{30}$)arylsulfonyl, heteroaryl-sulfonyl, ($C_1$-$C_{20}$) alkylsulfinyl, ($C_6$-$C_{30}$)arylsulfinyl, heteroarylsulfinyl, ($C_1$-$C_{20}$)alkoxycarbonyl, amino, NH($C_1$-$C_6$)alkyl, N(($C_1$-$C_6$)alkyl)$_2$, tri($C_1$-$C_{20}$)ammonium($C_1$-$C_{20}$)alkyl, heteroaryl($C_1$-$C_{20}$)alkyl, heteroaryl having quaternary nitrogen, heteroarylcarbonyl having quaternary nitrogen, ($C_6$-$C_{30}$)arylthio, ($C_1$-$C_{20}$)alkylphosphate, ($C_1$-$C_{20}$)alkylphosphonate, ($C_6$-$C_{30}$)arylphosphate, ($C_6$-$C_{30}$)arylphosphonate, phosphate, sulfate, saccharide, or $M^+$, wherein M is an alkali metal;
or when Z is $NR^1R^1$, $R^1$, $R^1R^1$ together with the N to which they are attached forms a heteroaryl or heterocycle group;
wherein any alkyl, alkenyl, alkynyl, cycloalkyl, alkoxy, amino, aryl, heteroaryl, or heterocycle group is optionally substituted with 1, 2, 3, 4, or 5 substituents selected from ($C_1$-$C_{20}$)alkyl, ($C_2$-$C_{20}$)alkenyl, ($C_2$-$C_{20}$)alkynyl, ($C_3$-$C_{20}$)cycloalkyl, ($C_1$-$C_{20}$)alkoxyl, ($C_1$-$C_{20}$)alkylcarbonyl, ($C_1$-$C_{20}$)alkylcarboxyl, halo, hydroxyl, —$COOR^x$, —$SO_2R^x$, —$SO_3R^x$, nitro, amino, ($C_1$-$C_{20}$)alkyl-S(O)—, ($C_1$-$C_{20}$)alkyl-$SO_2$—, phosphate, ($C_1$-$C_{20}$)alkylphosphate, ($C_1$-$C_{20}$)alkylphosphonate, NH($C_1$-$C_6$)alkyl, NH($C_1$-$C_6$)alkynyl, NH(($C_1$-$C_6$)alkyl)$_2$, N(($C_1$-$C_6$)alkynyl)$_2$, mercapto, ($C_1$-$C_{20}$)alkylthio, ($C_6$-$C_{30}$)aryl, ($C_6$-$C_{30}$)arylthio, trifluoromethyl, =O, heteroaryl, and heterocycle, and each substituent is optionally substituted with one to three R groups;
$R^x$ is H, ($C_1$-$C_6$)alkyl, or ($C_6$-$C_{30}$)aryl;
$A^-$ is an anion, present when a quaternary nitrogen is present;
or a salt thereof.

In another embodiment, the invention provides a compound of formula II:

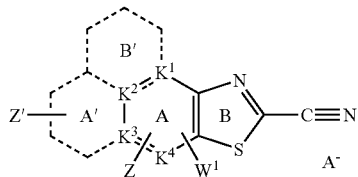

wherein

Z and Z' are independently $OR^1$, $NHR^1$, or $NR^1R^1$;

$W^1$ is H, halo, $(C_1-C_6)$alkyl, $(C_2-C_{20})$alkenyl, hydroxyl, or $(C_1-C_6)$alkoxy; or $W^1$ and Z are both keto groups on ring A, and at least one of the dotted lines denoting optional double bonds in ring A is absent;

each of $K^1$, $K^2$, $K^3$, and $K^4$ are independently CH, N, N-oxide, or $N-(C_1-C_6)$alkyl, and the dotted lines between $K^1$ and $K^2$, and $K^3$ and $K^4$, denote optional double bonds;

A' and B' are optional aromatic rings fused to ring A, only one of which is present in the compound, so as to form a fused tricyclic system; and when B' is present, the group Z is present, and when A' is present, the group Z is absent; and R is H, $(C_1-C_{20})$alkyl, $(C_2-C_{20})$alkenyl, $(C_2-C_{20})$alkynyl, $(C_3-C_{20})$cycloalkyl, $(C_1-C_{12})$alkoxy, $(C_6-C_{30})$aryl, heteroaryl, heterocycle, $(C_1-C_{20})$alkylsulfoxy, $(C_6-C_{30})$arylsulfoxy, heteroarylsulfoxy, $(C_1-C_{20})$alkoxycarbonyl, amino, $NH(C_1-C_6)$alkyl, $NH(C_1-C_6)$alkyl)$_2$, tri$(C_1-C_{20})$ammonium $(C_1-C_{20})$alkyl, heteroaryl$(C_1-C_{20})$alkyl, heteroaryl having quaternary nitrogen, heteroarylcarbonyl having quaternary nitrogen, saccharide, or $M^+$, wherein M is an alkali metal;

$R^1$ is $(C_6-C_{30})$aryl, heteroaryl, heterocycle, $(C_1-C_{20})$alkylthio, $(C_1-C_{20})$alkyl-S(O)—, $(C_1-C_{20})$alkyl-$SO_2$, —$SO_3(C_1-C_{20})$alkyl, saccharide, $(C_1-C_{20})$alkylphosphate, $(C_1-C_{20})$alkylphosphonate, $(C_6-C_{30})$arylthio, $(C_6-C_{30})$aryl-S(O)—, $(C_6-C_{30})$aryl-$SO_2$, —$SO_3(C_6-C_{30})$aryl, $(C_6-C_{30})$arylphosphate, $(C_6-C_{30})$arylphosphonate, or $R^1$ is $(C_1-C_{20})$alkyl substituted by $R^2$;

$R^2$ is $(C_2-C_{20})$alkenyl, $(C_2-C_{20})$alkynyl, $(C_3-C_{20})$cycloalkyl, $(C_1-C_{20})$alkoxyl, $(C_1-C_{20})$alkylcarbonyl, $(C_1-C_{20})$alkylcarboxyl, hydroxyl, —$COOR^x$, —$SO_3R^x$, $(C_1-C_{20})$alkylthio, $(C_6-C_{30})$arylthio, $(C_1-C_{20})$alkyl-S(O)—, $(C_1-C_{20})$alkyl-$SO_2$—, nitro, amino, $NH(C_1-C_6)$alkyl, $NH(C_1-C_6)$alkynyl, $N((C_1-C_6)$alkyl)$_2$, or $NH(C_1-C_6)$alkynyl)$_2$, mercapto, saccharide, or trifluoromethyl;

or when Z or Z' is $NR^1R^1$, $R^1R^1$ together with the N to which they are attached forms a heteroaryl or heterocycle group;

wherein any alkyl, alkenyl, alkynyl, cycloalkyl, alkoxy, amino, aryl, heteroaryl, or heterocycle group is optionally substituted with 1, 2, 3, 4, or 5 substituents selected from $(C_1-C_{20})$alkyl, $(C_2-C_{20})$alkenyl, $(C_2-C_{20})$alkynyl, $(C_3-C_{20})$cycloalkyl, $(C_1-C_{20})$alkoxyl, $(C_1-C_{20})$alkylcarbonyl, $(C_1-C_{20})$alkylcarboxyl, halo, hydroxyl, —$COOR^x$, —$SO_2R^x$, —$SO_3R^x$, $(C_1-C_{20})$alkyl-S(O)—, $(C_1-C_{20})$alkyl-$SO_2$—, phosphate, $(C_1-C_{20})$alkylphosphate, $(C_1-C_{20})$alkylphosphonate, nitro, amino, $NH(C_1-C_6)$alkyl, $NH(C_1-C_6)$alkynyl, $N((C_1-C_6)$alkyl)$_2$, $N((C_1-C_6)$alkynyl)$_2$, mercapto, $(C_1-C_{20})$alkylthio, $(C_6-C_{30})$aryl, $(C_6-C_{30})$arylthio, trifluoromethyl, =O, heteroaryl, and heterocycle, and each substituent is optionally substituted with one to three R groups;

$R^x$ is H or $(C_1-C_6)$alkyl;

when Z or Z' comprises a nitrogen moiety, a hydrogen of the Z or Z' nitrogen moiety may be replaced by the group L, wherein L is an amino acid radical, a peptide radical having up to 20 amino acid moieties, or any other small molecule that is a substrate for a nonluciferase;

when Z is a hydroxyl group or a nitrogen moiety, H of the hydroxyl or nitrogen moiety may be replaced by $(HO)_2P(O)—OCH_2—$, sulfo, —$PO_3H_2$, or by a cephalosporanic acid attached to the group Z via a carbon chain of one to about 12 carbon atoms;

when Z or Z' is a hydroxyl group or a nitrogen moiety, one H of the hydroxyl or nitrogen moiety may be replaced by the group L'-linker, wherein L' is a group removable by an enzyme to free the linker, and linker is a carbon chain that can self-cleave, optionally interrupted by one or more nitrogen atoms, oxygen atoms, carbonyl groups, optionally substituted aromatic rings, or peptide bonds, linker is attached to L' via an oxygen atom or an NH group at one terminus of the linker and the other terminus of the linker forms an ether, ester, or amide linkage with a group Z or Z';

when Z is $OR^1$, formula II is optionally a dimer connected at the two A rings via linker comprising a $(C_1-C_{12})$alkyl diradical that is optionally interrupted by one to four O atoms, N atoms, or an optionally substituted aryl, heteroaryl, or heterocycle group to form a bridge between the dimer of formula II, and the $R^1$ group of each Z group connecting the dimer of formula II is replaced by the bridge;

$A^-$ is an anion, present when a quaternary nitrogen is present; or a salt thereof.

In yet another embodiment, the invention provides a compound of formula II, which is a compound of formula IIA:

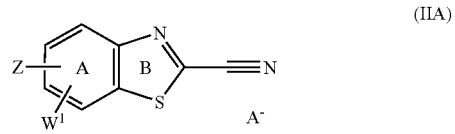

wherein

Z is $OR^1$, $NHR^1$, or $NR^1R^1$;

$W^1$ is H, halo, hydroxyl, $(C_1-C_6)$alkyl, or $(C_1-C_6)$alkoxy;

$R^1$ is $(C_6-C_{30})$aryl, heteroaryl, heterocycle, $(C_1-C_{20})$alkylthio, $(C_1-C_{20})$alkyl-S(O)—, $(C_1-C_{20})$alkyl-$SO_2$, —$SO_3(C_1-C_{20})$alkyl, saccharide, $(C_1-C_{20})$alkylphosphate, $(C_1-C_{20})$alkylphosphonate, $(C_6-C_{30})$arylthio, $(C_6-C_{30})$aryl-S(O)—, $(C_6-C_{30})$aryl-$SO_2$, —$SO_3(C_6-C_{30})$aryl, $(C_6-C_{30})$arylphosphate, $(C_6-C_{30})$arylphosphonate, or $R^1$ is $(C_1-C_{20})$alkyl substituted by $R^2$;

$R^2$ is $(C_2-C_{20})$alkenyl, $(C_2-C_{20})$alkynyl, $(C_3-C_{20})$cycloalkyl, $(C_1-C_{20})$alkoxyl, $(C_1-C_{20})$alkylcarbonyl, $(C_1-C_{20})$alkylcarboxyl, hydroxyl, —$COOR^x$, —$SO_3R^x$, $(C_1-C_{20})$alkylthio, $(C_6-C_{30})$arylthio, $(C_1-C_{20})$alkyl-S(O)—, $(C_1-C_{20})$alkyl-$SO_2$—, nitro, amino, $NH(C_1-C_6)$alkyl, $NH(C_1-C_6)$alkynyl, $N((C_1-C_6)$alkyl)$_2$, or $N((C_1-C_6)$alkynyl)$_2$, mercapto, saccharide, or trifluoromethyl;

or when Z is $NR^1R^1$, $R^1R^1$ together with the N to which they are attached forms a heteroaryl or heterocycle group;

wherein any alkyl, alkenyl, alkynyl, cycloalkyl, alkoxy, amino, aryl, heteroaryl, or heterocycle group is optionally substituted with 1, 2, 3, 4, or 5 substituents selected from $(C_1-C_{20})$alkyl, $(C_2-C_{20})$alkenyl, $(C_2-C_{20})$alkynyl, $(C_3-C_{20})$cycloalkyl, $(C_1-C_{20})$alkoxyl, $(C_1-C_{20})$alkylcarbonyl, $(C_1-C_{20})$alkylcarboxyl, halo, hydroxyl, —$COOR^x$, —$SO_2R^x$, —SO$_3$R$^x$, (C$_1$-C$_{20}$)alkyl-S(O)—, (C$_1$-C$_{20}$)alkyl-SO$_2$—, phosphate, (C$_1$-C$_{20}$)alkylphosphate, (C$_1$-C$_{20}$)alkylphosphonate, nitro, amino, NH(C$_1$-C$_6$)alkyl, NH(C$_1$-C$_6$)alkynyl, N((C$_1$-C$_6$)alkyl)$_2$, N((C$_1$-C$_6$)alkynyl)$_2$, mercapto, (C$_1$-C$_{20}$)alkylthio, (C$_6$-C$_{30}$)aryl, (C$_6$-C$_{30}$)arylthio, trifluoromethyl, =O, heteroaryl, and heterocycle, and each substituent is optionally substituted with one to three R groups;

R$^x$ is H or (C$_1$-C$_6$)alkyl;

when Z is OR$^1$, formula IIA is optionally a dimer connected at the two A rings via linker comprising a (C$_1$-C$_{12}$) alkyl diradical that is optionally interrupted by one to four O atoms, N atoms, or an optionally substituted aryl, heteroaryl, or heterocycle group to form a bridge between the dimer of formula IIA, and the R$^1$ group of each Z group connecting the dimer of formula II is replaced by the bridge;

A$^-$ is an anion, present when a quaternary nitrogen is present;

or a salt thereof.

In one embodiment, the invention provides a compound of formula III:

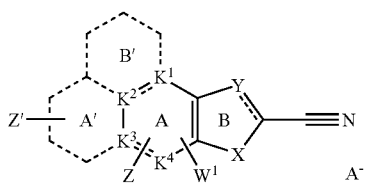

wherein
Y is N,N-oxide, N—(C$_1$-C$_6$)alkyl, or CH;
X is S, O, CH=CH, N=CH, or CH=N;
Z and Z' are independently H, OR, NHR, or NRR;
W$^1$ is H, halo, (C$_1$-C$_6$)alkyl, (C$_2$-C$_{20}$)alkenyl, hydroxyl, or (C$_1$-C$_6$)alkoxy; or
W$^1$ and Z are both keto groups on ring A, and at least one of the dotted lines denoting optional double bonds in ring A is absent;
each of K$^1$, K$^2$, K$^3$, and K$^4$ are independently CH, N,N-oxide, or N—(C$_1$-C$_6$)alkyl, and the dotted lines between K$^1$ and K$^2$, and K$^3$ and K$^4$, denote optional double bonds;
A' and B' are optional aromatic rings fused to ring A, only one of which is present in the compound, so as to form a fused tricyclic system; and
when B' is present, the group Z is present, and
when A' is present, the group Z is absent; and
the dotted line in ring B is an optional double bond;
each R is independently H, (C$_1$-C$_{20}$)alkyl, (C$_2$-C$_{20}$)alkenyl, (C$_2$-C$_{20}$)alkynyl, (C$_3$-C$_{20}$)cycloalkyl, (C$_1$-C$_{12}$)alkoxy, (C$_6$-C$_{30}$)aryl, heteroaryl, heterocycle, (C$_1$-C$_{20}$)alkylsulfoxy, (C$_6$-C$_{30}$)arylsulfoxy, heteroarylsulfoxy, (C$_1$-C$_{20}$)alkylsulfonyl, (C$_6$-C$_{30}$)arylsulfonyl, heteroaryl-sulfonyl, (C$_1$-C$_{20}$)alkylsulfinyl, (C$_6$-C$_{30}$)arylsulfinyl, heteroarylsulfinyl, (C$_1$-C$_{20}$)alkoxycarbonyl, amino, NH(C$_1$-C$_6$)alkyl, N((C$_1$-C$_6$)alkyl)$_2$, tri(C$_1$-C$_{20}$)ammonium(C$_1$-C$_{20}$)alkyl, heteroaryl(C$_1$-C$_{20}$)alkyl, heteroaryl having quaternary nitrogen, heteroarylcarbonyl having quaternary nitrogen, (C$_6$-C$_{30}$)arylthio, (C$_1$-C$_{20}$)alkylphosphate, (C$_1$-C$_{20}$)alkylphosphonate, (C$_6$-C$_{30}$)arylphosphate, (C$_6$-C$_{30}$)arylphosphonate, phosphate, sulfate, saccharide, or M$^+$, wherein M is an alkali metal;

or when Z or Z' is NR$^1$R$^1$, R$^1$R$^1$ together with the N to which they are attached forms a heteroaryl or heterocycle group;

wherein any alkyl, alkenyl, alkynyl, cycloalkyl, alkoxy, amino, aryl, heteroaryl, or heterocycle group is optionally substituted with 1, 2, 3, 4, or 5 substituents selected from (C$_1$-C$_{20}$)alkyl, (C$_2$-C$_{20}$)alkenyl, (C$_2$-C$_{20}$)alkynyl, (C$_3$-C$_{20}$)cycloalkyl, (C$_1$-C$_{20}$)alkoxyl, (C$_1$-C$_{20}$)alkylcarbonyl, (C$_1$-C$_{20}$)alkylcarboxyl, halo, hydroxyl, —COOR$^x$, —SO$_2$R$^x$, —SO$_3$R$^x$, nitro, amino, (C$_1$-C$_{20}$)alkyl-S(O)—, (C$_1$-C$_{20}$)alkyl-SO$_2$—, phosphate, (C$_1$-C$_{20}$)alkylphosphate, (C$_1$-C$_{20}$)alkylphosphonate, NH(C$_1$-C$_6$)alkyl, NH(C$_1$-C$_6$)alkynyl, N((C$_1$-C$_6$)alkyl)$_2$, N((C$_1$-C$_6$)alkynyl)$_2$, mercapto, (C$_1$-C$_{20}$)alkylthio, (C$_6$-C$_{30}$)aryl, (C$_6$-C$_{30}$)arylthio, trifluoromethyl, =O, heteroaryl, and heterocycle, and each substituent is optionally substituted with one to three R groups;

R$^x$ is H, (C$_1$-C$_6$)alkyl, or (C$_6$-C$_{30}$)aryl;

when Z or Z' comprises a nitrogen moiety, one or both of the hydrogens of the Z or Z' nitrogen moiety may be replaced by (C$_1$-C$_{20}$)alkyl or the group L, wherein L is an amino acid radical, a peptide radical having up to 20 amino acid moieties, or any other small molecule that is a substrate for a nonluciferase;

when Z is a hydroxyl group or a nitrogen moiety, H of the hydroxyl or nitrogen moiety may be replaced by (HO)$_2$P(O)—OCH$_2$—, sulfo, —PO$_3$H$_2$, or by a cephalosporanic acid attached to the group Z via a carbon chain of one to about 12 carbon atoms;

when Z or Z' is a hydroxyl group or a nitrogen moiety, one H of the hydroxyl or nitrogen moiety may be replaced by the group L'-linker, wherein L' is a group removable by an enzyme to free the linker, and linker is a carbon chain that can self-cleave, optionally interrupted by one or more nitrogen atoms, oxygen atoms, carbonyl groups, optionally substituted aromatic rings, or peptide bonds, linker is attached to L' via an oxygen atom or an NH group at one terminus of the linker and the other terminus of the linker forms an ether, ester, or amide linkage with a group Z or Z';

when Z is OR, formula III is optionally a dimer connected at the two A rings via a linker comprising a (C$_1$-C$_{12}$)alkyl diradical that is optionally interrupted by one to four O atoms, N atoms, or an optionally substituted aryl, heteroaryl, or heterocycle group to form a bridge between the dimer of formula III, and the R group of each Z group connecting the dimer of formula III is replaced by the bridge;

A$^-$ is an anion, present when a quaternary nitrogen is present;

or a salt thereof.

In one embodiment, the invention provides a compound of formula III, which is a compound of formula IIIA:

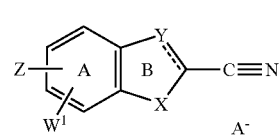

wherein
Y is N,N-oxide, N—(C$_1$-C$_6$)alkyl, or CH;
X is S, O, CH=CH, N=CH, or CH=N;
Z is H, OR, NHR, or NRR;
W$^1$ is H, halo, hydroxyl, (C$_1$-C$_6$)alkyl, (C$_2$-C$_{10}$)alkenyl, or (C$_1$-C$_6$)alkoxy;
the dotted line in ring B is an optional double bond;
each R is independently H, (C$_1$-C$_{20}$)alkyl, (C$_2$-C$_{20}$)alkenyl, (C$_2$-C$_{20}$)alkynyl, (C$_3$-C$_{20}$)cycloalkyl, (C$_1$-C$_{12}$)alkoxy, (C$_6$-C$_{30}$)aryl, heteroaryl, heterocycle, (C$_1$-C$_{20}$)alkylsulfoxy, ($C_6$-$C_{30}$)arylsulfoxy, heteroarylsulfoxy, ($C_1$-$C_{20}$)alkylsulfonyl, ($C_6$-$C_{30}$)arylsulfonyl, heteroaryl-sulfonyl, ($C_1$-$C_{20}$)alkylsulfinyl, ($C_6$-$C_{30}$)arylsulfinyl, heteroarylsulfinyl, ($C_1$-$C_{20}$)alkoxycarbonyl, amino, NH($C_1$-$C_6$)alkyl, N(($C_1$-$C_6$)alkyl)$_2$, tri($C_1$-$C_{20}$)ammonium($C_1$-$C_{20}$)alkyl, heteroaryl($C_1$-$C_{20}$)alkyl, heteroaryl having quaternary nitrogen, heteroarylcarbonyl having quaternary nitrogen, ($C_6$-$C_{30}$)arylthio, ($C_1$-$C_{20}$)alkylphosphate, ($C_1$-$C_{20}$)alkylphosphonate, ($C_6$-$C_{30}$)arylphosphate, ($C_6$-$C_{30}$)arylphosphonate, phosphate, sulfate, saccharide, or $M^+$, wherein M is an alkali metal;

or when Z is $NR^1R^1$, $R^1R^1$ together with the N to which they are attached forms a heteroaryl or heterocycle group;

wherein any alkyl, alkenyl, alkynyl, cycloalkyl, alkoxy, amino, aryl, heteroaryl, or heterocycle group is optionally substituted with 1, 2, 3, 4, or 5 substituents selected from ($C_1$-$C_{20}$)alkyl, ($C_2$-$C_{20}$)alkenyl, ($C_2$-$C_{20}$)alkynyl, ($C_3$-$C_{20}$)cycloalkyl, ($C_1$-$C_{20}$)alkoxy, ($C_1$-$C_{20}$)alkylcarbonyl, ($C_1$-$C_{20}$)alkylcarboxyl, halo, hydroxyl, —$COOR^x$, —$SO_2R^x$, —$SO_3R^x$, nitro, amino, ($C_1$-$C_{20}$)alkyl-S(O)—, ($C_1$-$C_{20}$)alkyl-$SO_2$—, phosphate, ($C_1$-$C_{20}$)alkylphosphate, ($C_1$-$C_{20}$)alkylphosphonate, NH($C_1$-$C_6$)alkyl, NH($C_1$-$C_6$)alkynyl, N(($C_1$-$C_6$)alkyl)$_2$, N(($C_1$-$C_6$)alkynyl)$_2$, mercapto, ($C_1$-$C_{20}$)alkylthio, ($C_6$-$C_{30}$)aryl, ($C_6$-$C_{30}$)arylthio, trifluoromethyl, =O, heteroaryl, and heterocycle, and each substituent is optionally substituted with one to three R groups;

$R^x$ is H, ($C_1$-$C_6$)alkyl, or ($C_6$-$C_{30}$)aryl;

when Z is OR, formula III is optionally a dimer connected at the two A rings via a linker comprising a ($C_1$-$C_{12}$)alkyl diradical that is optionally interrupted by one to four O atoms, N atoms, an optionally substituted aryl, heteroaryl, or heterocycle group, or a combination thereof, to form a bridge between the dimer of formula III, and the R group of each Z group connecting the dimer of formula III is replaced by the bridge;

$A^-$ is an anion, present when a quaternary nitrogen is present;

or salt thereof.

In one embodiment, the invention provides a compound of formula V:

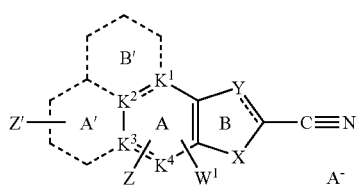

(V)

wherein

Y is N,N-oxide, N-loweralkyl, or CH;

X is S, CH=CH, or N=C,

Z and Z' are H, OR, NHR, or NRR;

W is H, halo, $C_{1-6}$alkyl, $C_{2-20}$alkenyl, hydroxyl, or $C_{1-6}$alkoxy; or W and Z on ring A are both keto groups;

each of $K^1$, $K^2$, $K^3$, and $K^4$ are independently CH, N,N-oxide, or N-loweralkyl;

R is H, $C_{1-20}$alkyl, substituted $C_{1-20}$alkyl, $C_{2-20}$alkenyl, substituted $C_{2-20}$alkenyl, halogenated $C_{2-20}$alkenyl, substituted halogenated $C_{2-20}$alkenyl, $C_{3-20}$alkynyl, substituted $C_{3-20}$alkynyl, $C_{2-20}$alkenyl$C_{1-20}$alkyl, substituted $C_{2-20}$alkenyl$C_{1-20}$alkyl, $C_{3-20}$alkynyl$C_{2-20}$alkenyl, substituted $C_{3-20}$alkynyl$C_{2-20}$alkenyl, $C_{3-20}$cycloalkyl, substituted $C_{3-20}$cycloalkyl, $C_{6-30}$aryl, heteroaryl, $C_{6-30}$aryl$C_{1-20}$alkyl, substituted $C_{6-30}$aryl, substituted heteroaryl, substituted $C_{6-30}$aryl$C_{1-20}$alkyl, alkylsulfoxy$C_{1-20}$alkyl, $C_{1-20}$alkoxycarbonyl, $C_{6-30}$aryl$C_{1-20}$alkoxycarbonyl, $C_{6-30}$arylthio$C_{1-20}$alkyl, hydroxy$C_{1-20}$alkyl, tri$C_{1-20}$ammonium$C_{1-20}$alkyl, heteroaryl$C_{1-20}$alkyl, substituted heteroaryl$C_{1-20}$alkyl, heteroaryl having quaternary nitrogen, heteroarylcarbonyl having quaternary nitrogen, and N-methyl-tetrahydropyridinyl; and $M^+$ when Z" is oxygen, wherein M is an alkali metal; wherein the alkyl, cycloalkyl, alkenyl, and/or alkynyl groups may be optionally substituted by one more $C_{1-20}$alkyl, halo, hydroxyl, acetyl, amino, lower alkylamino, lower alkynylamino, imidazolinylmethylamino, di-lower alkylamino, di-lower alkynylamino, piperidino, pyrrolidino, azetidino, aziridino, di-imidazolinylmethylamino, mercapto, $C_{1-20}$alkylthio, $C_{6-30}$arylthio, or trifluoromethyl groups, substituted $C_{6-30}$aryl$C_{1-20}$alkyl carbonyl; and each group R is defined independently if more than one is present;

and wherein when Z is amino, one or both of the hydrogens may be replaced by $C_{1-20}$alkyl, or the group L, wherein L is an amino acid radical, a peptide radical having up to 20 amino acid moieties, or may be any other small molecule that is a substrate for a nonluciferase;

and wherein when Z is hydroxyl or amino, H may be replaced by $(HO)_2P(O)$—$OCH_2$—, sulfo, or —$PO_3H_2$, or by cephalosporanic acid attached to the group Z via a carbon chain of one or more carbon atoms; and when Z is hydroxyl or amino, H may be replaced by the group L'-linker, wherein L' is a group removable by an enzyme to free the linker, and the linker is a carbon chain that may optimally self-cleave, optionally interrupted by one or more nitrogen atoms, oxygen atoms, carbonyl groups, (substituted)aromatic rings, or peptide bonds, and linker is attached to L' via an oxygen atom or an NH group at one terminus of the linker and the other terminus of the linker forms an ether, ester, or amide linkage with the group Z; and when Z is hydroxyl, formula V includes a dimer connected at the two A rings via an —$OCH_2O$— bridge; and wherein A' and B' are optional aromatic rings fused to ring A, only one of which may be present at a time, so as to form a fused tricyclic system; and when B' is present, the group Z is present, and when A' is present, the group Z is absent; and wherein one carbon of ring A may be replaced by an N-oxide moiety;

the dotted line in ring B is an optional double bond;

if X is N=C, ring C is attached at the carbon atom of the N=C moiety; and $A^-$ is an anion, present when a quaternary nitrogen is present; or a salt thereof.

Further derivatives herein have the general formula VII:

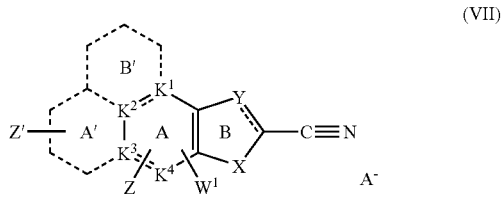

(VII)

wherein
Y is N-oxide, N-loweralkyl, or CH;
X is S or CH=CH; or
Y is N and X is N=C or CH=CH;
Z and Z' are H, OR, NHR, or NRR; or
Z is a cyclic dietherified dihydroxyborane group attached to ring A via the boron atom;
W is H, halo, $C_{1-6}$alkyl, $C_{2-20}$alkenyl, hydroxyl, or $C_{1-6}$alkoxy;
each of $K^1$, $K^2$, $K^3$, and $K^4$ are independently CH, N,N-oxide, or N-loweralkyl;
R is H, $C_{1-20}$alkyl, substituted $C_{1-20}$alkyl, $C_{2-20}$alkenyl, substituted $C_{2-20}$alkenyl, halogenated $C_{2-20}$alkenyl, substituted halogenated $C_{2-20}$alkenyl, $C_{2-20}$alkenyl$C_{1-20}$alkyl, substituted $C_{2-20}$alkenyl$C_{1-20}$alkyl, $C_{3-20}$alkynyl, substituted $C_{3-20}$alkynyl, $C_{3-20}$alkynyl$C_{2-20}$alkenyl, substituted $C_{3-20}$alkynyl$C_{2-20}$alkenyl, $C_{3-20}$cycloalkyl, substituted $C_{3-20}$cycloalkyl, $C_{6-30}$aryl, heteroaryl, $C_{6-30}$aryl$C_{1-20}$alkyl, substituted $C_{6-30}$aryl, substituted heteroaryl, substituted $C_{6-30}$aryl$C_{1-20}$alkyl, $C_{1-20}$alkoxycarbonyl, $C_{6-30}$aryl$C_{1-20}$alkoxycarbonyl, $C_{6-30}$arylthio$C_{1-20}$alkyl, hydroxy$C_{1-20}$alkyl, tri$C_{1-20}$ammonium$C_{1-20}$alkyl, heteroaryl$C_{1-20}$alkyl, substituted heteroaryl$C_{1-20}$alkyl, heteroaryl having quaternary nitrogen, heteroarylcarbonyl having quaternary nitrogen, N-methyl-tetrahydropyridinyl, pentafluorophenylsulphonyl, and $M^+$ when $Z''$ is oxygen, wherein M is an alkali metal; wherein the alkyl, cycloalkyl, alkenyl, and/or alkynyl groups may be optionally substituted by one more $C_{1-20}$alkyl, halo, hydroxyl, acetyl, amino, lower alkylamino, lower alkynylamino, imidazolinylmethylamino, di-lower alkylamino, di-lower alkynylamino, piperidino, pyrrolidino, azetidino, aziridino, di-imidazolinylmethylamino, mercapto, $C_{1-20}$alkylthio, $C_{6-30}$arylthio, or trifluoromethyl groups; and each group R is defined independently if more than one is present;

and wherein when Z is amino, one or both of the hydrogens may be replaced by $C_{1-20}$alkyl, or the group L, wherein L is an amino acid radical, a peptide radical having up to 20 amino acid moieties, or may be any other small molecule that is a substrate for a nonluciferase;

and wherein when Z is hydroxyl or amino, H may be replaced by $(HO)_2P(O)$—$OCH_2$—, sulfo, or —$PO_3H_2$, or by a cephalosporanic acid attached to the group Z via a carbon chain of one or more carbon atoms; and when Z is hydroxyl or amino, H may be replaced by the group L'-linker, wherein L' is a group removable by an enzyme to free the linker, and linker is carbon chain that can self-cleave, optionally interrupted by one or more nitrogen atoms, oxygen atoms, carbonyl groups, (substituted)aromatic rings, or peptide bonds, and linker is attached to L' via an oxygen atom or an NH group at one terminus of the linker and the other terminus of the linker forms an ether, ester, or amide linkage with the group Z; and when Z is hydroxyl, formula VII includes a dimer connected at the two A rings via an —$OCH_2O$— bridge; and wherein A' and B' are optional aromatic rings fused to ring A, only one of which may be present at a time, so as to form a fused tricyclic system; and when B' is present, the group Z is present, and
when A' is present, the group Z is absent; and
wherein one carbon of ring A may be replaced by an N-oxide moiety;

the dotted line in ring B is an optional double bond;
if X is N=C, ring C can optionally be attached at the carbon atom of the N=C moiety; and $A^-$ is an anion, present when a quaternary nitrogen is present; or a salt thereof.

Other derivatives include a compound of formula VIII:

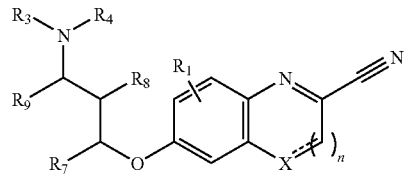

(VIII)

wherein
n=0 or 1 and when
n=0, then X=S, and ----- is a single bond; or when
n=1, then X=CH, and ----- is a double bond;
$R_1$=H, F, or OH;
$R_3$ and $R_4$ are independently H, methyl, ethyl, propyl, allyl, imidazolinylmethyl, or
$R_3$ and $R_4$ together with the nitrogen atom to which they are attached form a piperidino, pyrrolidino, azetidino, or aziridino ring;
$R_7$ is H or methyl;
$R_8$ is H, methyl, hydroxyl, or acetyl; and
$R_9$ is H or methyl. Compounds of formula VIII may be useful as MAO substrates.

Yet other derivatives include a compound of formula IX:

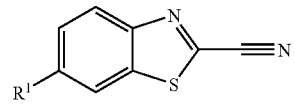

(IX)

wherein $R^1$ is H, OR, NH—C(O)—O-benzyl, or NH—O-isobutyl; and R is lower alkyl, benzyl, 2,4,6-trimethylbenzyl, phenylpiperazinobenzyl, o-trifluoromethylbenzyl, or 3-picolinyl. Such derivatives may be useful as P450 substrates.

Also provided is a compound of formula X:

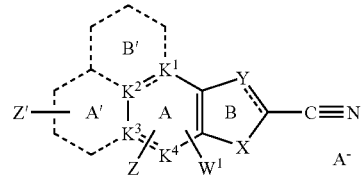

(X)

wherein
Y is N,N-oxide, N-loweralkyl, or CH;
X is S, CH=CH, or N=C,
Z and Z' are independently H, OR, NHR, or NRR;
$W^1$ is H, halo, $C_{1-6}$alkyl, $C_{2-20}$alkenyl, hydroxyl, or $C_{1-6}$alkoxy; or
$W^1$ and Z are both keto groups on ring A, and the dotted lines in ring A are absent;
each of $K^1$, $K^2$, $K^3$, and $K^4$ are independently CH, N,N-oxide, or N-loweralkyl, and the dotted lines between $K^1$ and $K^2$, and $K^3$ and $K^4$, denote optional double bonds;

R is H, amino, $C_{1-20}$alkyl, $C_{2-20}$alkenyl, halogenated $C_{2-20}$alkenyl, $C_{3-20}$alkynyl, $C_{2-20}$alkenyl$C_{1-20}$alkyl, $C_{3-20}$alkynyl$C_{2-20}$alkenyl, $C_{3-20}$cycloalkyl, $C_{6-30}$aryl, heteroaryl, $C_{6-30}$aryl$C_{1-20}$alkyl, $C_{1-12}$alkoxy, $C_{1-20}$alkylsulfoxy, $C_{6-30}$arylsulfoxy, $C_{6-30}$arylsulfoxy$C_{1-20}$alkyl, $C_{1-20}$alkylsulfoxy$C_{1-20}$ alkyl, $C_{1-20}$alkoxycarbonyl, $C_{6-30}$aryl$C_{1-20}$alkoxycarbonyl, $C_{6-30}$arylthio$C_{1-20}$alkyl, hydroxy$C_{1-20}$alkyl, tri$C_{1-20}$ammonium$C_{1-20}$alkyl, heteroarylsulfoxy, heteroaryl$C_{1-20}$alkyl, heteroaryl having quaternary nitrogen, heteroarylcarbonyl having quaternary nitrogen, N-methyl-tetrahydropyridinyl;

wherein any alkyl, alkenyl, alkynyl, cycloalkyl, alkoxy, aryl, or heteroaryl groups of R can be optionally substituted by one or more, e.g., 1, 2, 3, 4, or 5, $C_{1-20}$alkyl, halo, hydroxyl, acetyl, —COOR$^1$, —SO$_3$R$^1$, amino, nitro, lower alkylamino, lower alkynylamino, imidazolinylmethylamino, di-lower alkylamino, di-lower alkynylamino, piperidino, pyrrolidino, azetidino, aziridino, di-imidazolinylmethylamino, mercapto, $C_{1-20}$alkylthio, $C_{6-30}$arylthio, trifluoromethyl, $C_{1-20}$alkylcarboxyl, $C_{6-30}$aryl, substituted $C_{6-30}$aryl, $C_{6-30}$aryl$C_{1-20}$alkoxyl, heterocycle $C_{1-20}$alkyl, substituted $C_{6-30}$aryl$C_{1-20}$alkoxyl, $C_{6-30}$aryl$C_{1-20}$alkyl carbonyl, substituted $C_{6-30}$aryl$C_{1-20}$alkyl carbonyl or additional unsubstituted R groups; and wherein each group R is defined independently if more than one is present;

wherein heterocycle $C_{1-20}$alkyl is optionally substituted with one or more, e.g., 1, 2, 3, 4, or 5, R groups;

R$^1$ is hydrogen or $C_{1-6}$alkyl;

and wherein when Z is amino, one or both of the hydrogens of the amino group may be replaced by $C_{1-20}$alkyl, or the group L, wherein L is an amino acid radical, a peptide radical having up to 20 amino acid moieties, or any other small molecule that is a substrate for a nonluciferase;

and wherein when Z is hydroxyl or amino, H of the hydroxyl or amino may be replaced by (HO)$_2$P(O)—OCH$_2$—, sulfo, —PO$_3$H$_2$, or by a cephalosporanic acid attached to the group Z via a carbon chain of one or more carbon atoms; and when Z or Z' is hydroxyl or amino, one H of the hydroxyl or amino may be replaced by the group L'-linker, wherein L' is a group removable by an enzyme to free the linker, and linker is carbon chain that can self-cleave, optionally interrupted by one or more nitrogen atoms, oxygen atoms, carbonyl groups, (substituted)aromatic rings, or peptide bonds, and linker is attached to L' via an oxygen atom or an NH group at one terminus of the linker and the other terminus of the linker forms an ether, ester, or amide linkage with the group Z, Z', or Z"-R; and when Z is OR, formula X can optionally be a dimer connected at the two A rings via a CH$_2$ or CH$_2$—C$_6$H$_4$—CH$_2$ bridge, and the R group of each Z group connecting the dimer of formula X is replaced by the bridge; and wherein A' and B' are optional aromatic rings fused to ring A, only one of which may be present at a time, so as to form a fused tricyclic system; and when B' is present, the group Z is present, and
when A' is present, the group Z is absent; and wherein one carbon of ring A may be replaced by an N-oxide moiety;

the dotted line in ring B is an optional double bond;

if X is N═C, ring C can optionally be attached at the carbon atom of the N═C moiety; and A$^-$ is an anion, present when a quaternary nitrogen is present; or a salt thereof.

Further provided is a compound of formula XI:

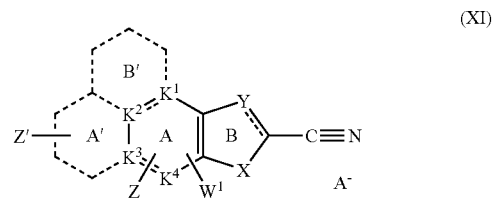

(XI)

wherein

Y is N-oxide, N-loweralkyl, or CH;

X is S or CH═CH; or

Y is N and X is N═C or CH═CH;

Z and Z' are H, OR, NHR, or NRR; or

Z is a cyclic dietherified dihydroxyborane group attached to ring A via the boron atom;

W$^1$ is H, halo, $C_{1-6}$alkyl, $C_{2-20}$alkenyl, hydroxyl, or $C_{1-6}$alkoxy;

each of K$^1$, K$^2$, K$^3$, and K$^4$ are independently CH, N,N-oxide, or N-loweralkyl, and the dotted lines between K$^1$ and K$^2$, and K$^3$ and K$^4$, denote optional double bonds;

R is H, $C_{1-20}$alkyl, $C_{2-20}$alkenyl, halogenated $C_{2-20}$alkenyl, $C_{3-20}$alkynyl, $C_{2-20}$alkenyl$C_{1-20}$alkyl, $C_{3-20}$alkynyl$C_{2-20}$alkenyl, $C_{3-20}$cycloalkyl, $C_{6-30}$aryl, heteroaryl, $C_{6-30}$aryl$C_{1-20}$ alkyl, $C_{1-20}$alkylsulfoxy, $C_{6-30}$arylsulfoxy, $C_{6-30}$arylsulfoxy$C_{1-20}$alkyl, $C_{1-20}$alkylsulfoxy$C_{1-20}$alkyl, $C_{1-20}$alkoxycarbonyl, $C_{6-30}$aryl$C_{1-20}$alkoxycarbonyl, $C_{6-30}$arylthio$C_{1-20}$alkyl, hydroxy$C_{1-20}$alkyl, hydroxy$C_{1-20}$alkyl, tri$C_{1-20}$ammonium$C_{1-20}$alkyl, heteroarylsulfoxy, heteroaryl$C_{1-20}$alkyl, heteroaryl having quaternary nitrogen, heteroarylcarbonyl having quaternary nitrogen, N-methyl-tetrahydropyridinyl;

wherein the alkyl, alkenyl, alkynyl, cycloalkyl, aryl, and heteroaryl groups of R can be optionally substituted by one or more, e.g., 1, 2, 3, 4, or 5, $C_{1-20}$alkyl, halo, hydroxyl, acetyl, —COOR$^1$, —SO$_3$R$^1$, amino, nitro, lower alkylamino, lower alkynylamino, imidazolinylmethylamino, di-lower alkylamino, di-lower alkynylamino, piperidino, pyrrolidino, azetidino, aziridino, di-imidazolinylmethylamino, mercapto, $C_{1-20}$alkylthio, $C_{6-30}$arylthio, trifluoromethyl, substituted $C_{6-30}$aryl, $C_{1-20}$alkylcarboxyl, substituted $C_{6-30}$aryl, substituted $C_{6-30}$aryl$C_{1-20}$alkoxyl, substituted $C_{6-30}$aryl$C_{1-20}$alkyl carbonyl or additional unsubstituted R group; and each group R is defined independently if more than one is present;

R$^1$ is hydrogen or $C_{1-6}$alkyl;

and wherein when Z is amino, one or both of the hydrogens of the amino group may be replaced by $C_{1-20}$alkyl, or the group L, wherein L is an amino acid radical, a peptide radical having up to 20 amino acid moieties, or may be any other small molecule that is a substrate for a nonluciferase;

and wherein when Z or Z' is hydroxyl or amino, H of the hydroxyl or amino may be replaced by (HO)$_2$P(O)—OCH$_2$—, sulfo, —PO$_3$H$_2$, or by a cephalosporanic acid attached to the group Z via a carbon chain of one or more carbon atoms; and when Z is hydroxyl or amino, one H of the hydroxyl or amino may be replaced by the group L'-linker, wherein L' is a group removable by an enzyme to free the linker, and linker is carbon chain that can self-cleave, optionally interrupted by one or more nitrogen atoms, oxygen atoms, carbonyl groups, (substituted)aromatic rings, or peptide bonds, and linker is attached to L' via an oxygen atom or an NH group at one terminus of the linker and the other terminus of the linker forms an ether, ester, or amide linkage with the group Z or Z-R; and when Z is hydroxyl, formula XI includes a dimer connected at the two A rings via an —OCH$_2$O— bridge; and
wherein A' and B' are optional aromatic rings fused to ring A, only one of which may be present at a time, so as to form a fused tricyclic system; and when B' is present, the group Z is present, and
when A' is present, the group Z is absent; and
wherein the dotted line in ring B is an optional double bond;

if X is N=C, ring C can optionally be attached at the carbon atom of the N=C moiety; and A$^-$ is an anion, present when a quaternary nitrogen is present; or a salt thereof.

Also provided is a compound of formula XII:

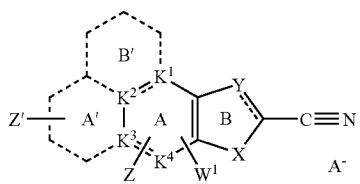

(XII)

wherein

Y is N,N-oxide, N-loweralkyl, or CH;

X is S, CH=CH, or N=C,

Z and Z' are independently H, OR, NHR, or NRR;

$W^1$ is H, halo, $C_{1-6}$alkyl, $C_{2-20}$alkenyl, hydroxyl, or $C_{1-6}$alkoxy; or $W^1$ and Z are both keto groups on ring A, and the dotted lines in ring A are absent;

each of $K^1$, $K^2$, $K^3$, and $K^4$ are independently CH, N,N-oxide, or N-loweralkyl, and the dotted lines between $K^1$ and $K^2$, and $K^3$ and $K^4$, denote optional double bonds;

R is H, $C_{1-20}$alkyl, $C_{2-20}$alkenyl, halogenated $C_{2-20}$alkenyl, $C_{3-20}$alkynyl, $C_{2-20}$alkenyl$C_{1-20}$alkyl, $C_{3-20}$alkynyl$C_{2-20}$alkenyl, $C_{3-20}$cycloalkyl, $C_{6-30}$aryl, heteroaryl, heterocyclic, substituted heterocyclic, $C_{6-30}$aryl$C_{1-20}$alkyl, $C_{1-20}$alkylsulfoxy, $C_{6-30}$arylsulfoxy, $C_{6-30}$arylsulfoxy$C_{1-20}$alkyl, $C_{1-20}$alkylsulfoxy$C_{1-20}$alkyl, $C_{1-20}$alkoxycarbonyl, $C_{6-30}$aryl$C_{1-20}$alkoxycarbonyl, $C_{6-30}$arylthio$C_{1-20}$alkyl, hydroxy$C_{1-20}$alkyl, tri$C_{1-20}$ammonium$C_{1-20}$alkyl, heteroarylsulfoxy, heteroaryl$C_{1-20}$alkyl, heteroaryl having quaternary nitrogen, heteroarylcarbonyl having quaternary nitrogen, N-methyl-tetrahydropyridinyl;

wherein the alkyl, alkenyl, alkynyl, cycloalkyl, aryl, and heteroaryl groups of R can be optionally substituted by one or more, e.g., 1, 2, 3, 4, or 5, $C_{1-20}$alkyl, halo, hydroxyl, acetyl, —COOR$^1$, —SO$_3$R$^1$, amino, nitro, lower alkylamino, lower alkynylamino, imidazolinylmethylamino, di-lower alkylamino, di-lower alkynylamino, piperidino, pyrrolidino, azetidino, aziridino, di-imidazolinylmethylamino, mercapto, $C_{1-20}$alkylthio, $C_{6-30}$arylthio, trifluoromethyl, $C_{1-20}$alkylcarboxyl, $C_{6-30}$aryl, substituted $C_{6-30}$aryl, $C_{6-30}$aryl$C_{1-20}$alkoxyl, substituted $C_{6-30}$aryl$C_{1-20}$alkoxyl, $C_{6-30}$aryl$C_{1-20}$alkyl carbonyl, substituted $C_{6-30}$aryl$C_{1-20}$alkyl carbonyl or additional unsubstituted R groups; and wherein each group R is defined independently if more than one is present;

wherein substituted aryl groups are substituted with one or alkyl, alkenyl, alkynyl, cycloalkyl, aryl, heterocyclic, substituted heterocyclic, and heteroaryl groups of R can be optionally substituted by one or more $C_{1-20}$alkyl, $C_6$-$C_{10}$aryl, halo, hydroxyl, acetyl, —COOR$^1$, amino, nitro, lower alkylamino, lower alkynylamino, imidazolinylmethylamino, di-lower alkylamino, di-lower alkynylamino, piperidino, pyrrolidino, azetidino, aziridino, di-imidazolinyl-methylamino, mercapto, $C_{1-20}$alkylthio, $C_{6-30}$arylthio, or trifluoromethyl groups;

R$^1$ is hydrogen or $C_{1-6}$alkyl;
and wherein when Z is amino, one or both of the hydrogens of the amino group may be replaced by $C_{1-20}$alkyl, or the group L, wherein L is an amino acid radical, a peptide radical having up to 20 amino acid moieties, or any other small molecule that is a substrate for a nonluciferase;

and wherein when Z is hydroxyl or amino, H may be replaced by (HO)$_2$P(O)—OCH$_2$—, sulfo, or —PO$_3$H$_2$, or by a cephalosporanic acid attached to the group Z via a carbon chain of one or more carbon atoms; with the proviso that when ring B is a thiazole ring, the sulfo or the —PO$_3$H$_2$ group is attached to the hydroxyl oxygen via a loweralkylene chain; and when Z or Z' is hydroxyl or amino, one H may be replaced by the group L'-linker, wherein L' is a group removable by an enzyme to free the linker, and linker is carbon chain that can self-cleave, optionally interrupted by one or more nitrogen atoms, oxygen atoms, carbonyl groups, (substituted)aromatic rings, or peptide bonds, and linker is attached to L' via an oxygen atom or an NH group at one terminus of the linker and the other terminus of the linker forms an ether, ester, or amide linkage with the group Z or Z'-R; and when Z is hydroxyl, formula XII includes a dimer connected at the two A rings via an —OCH$_2$O— bridge; and
wherein A' and B' are optional aromatic rings fused to ring A, only one of which may be present at a time, so as to form a fused tricyclic system; and when B' is present, the group Z is present, and
when A' is present, the group Z is absent; and
wherein the dotted line in ring B is an optional double bond;

if X is N=C, ring C can optionally be attached at the carbon atom of the N=C moiety; and A$^-$ is an anion, present when a quaternary nitrogen is present; or a salt thereof.

Also provided is a compound of formula XV:

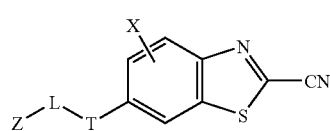

(XV)

wherein

Z is hydrogen or a protecting group;

L is a linker as described herein below, for example, an amino acid or a chain of 2-10 amino acids;

T is O or NH; and

X is hydrogen or fluorine, with the proviso that if X=H then at least one of the amino acids is R, N, D, C, Q, E, H, K, S, T, W, or Y.

In various embodiments, Z can be a protecting group for a heteroatom, for example, a nitrogen or oxygen protecting group. Examples of protecting groups are discussed above. In certain specific embodiments, the protecting groups can be Cbz, Boc, acetyl, or succinyl groups.

In certain embodiments, the compound of formula XV can be the compound
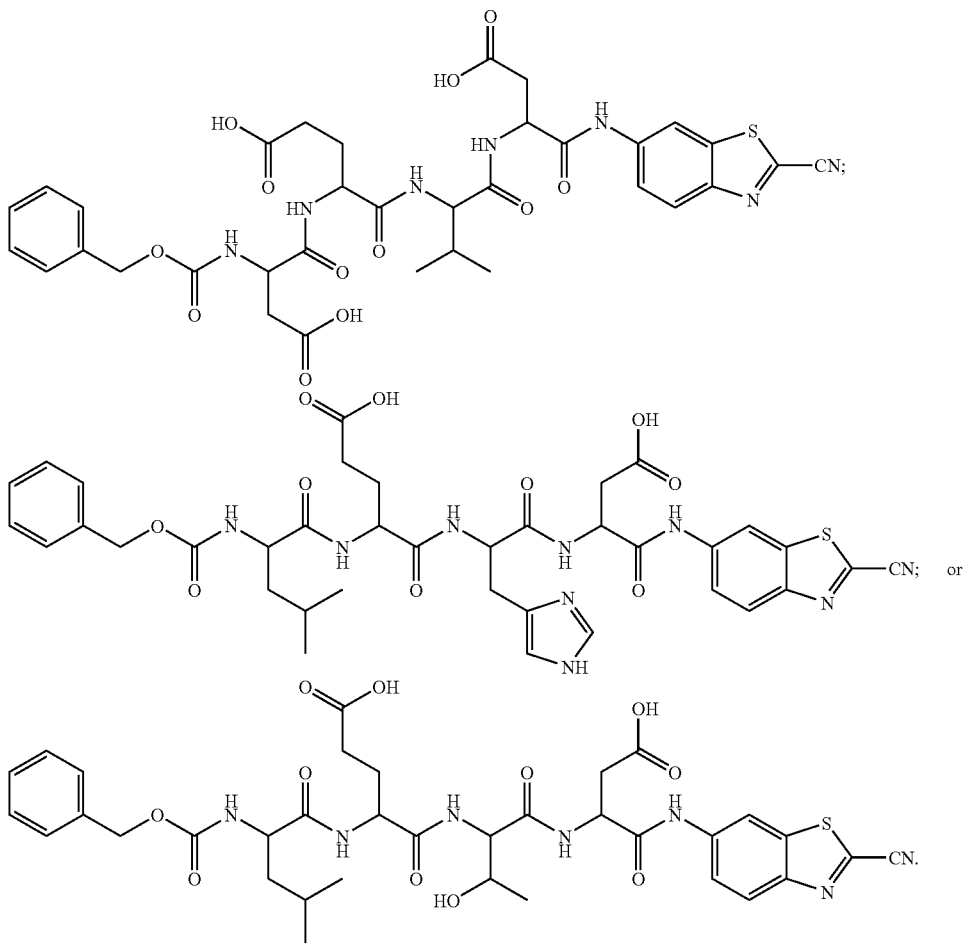
Other examples of compounds of the formulas above include the following structures:
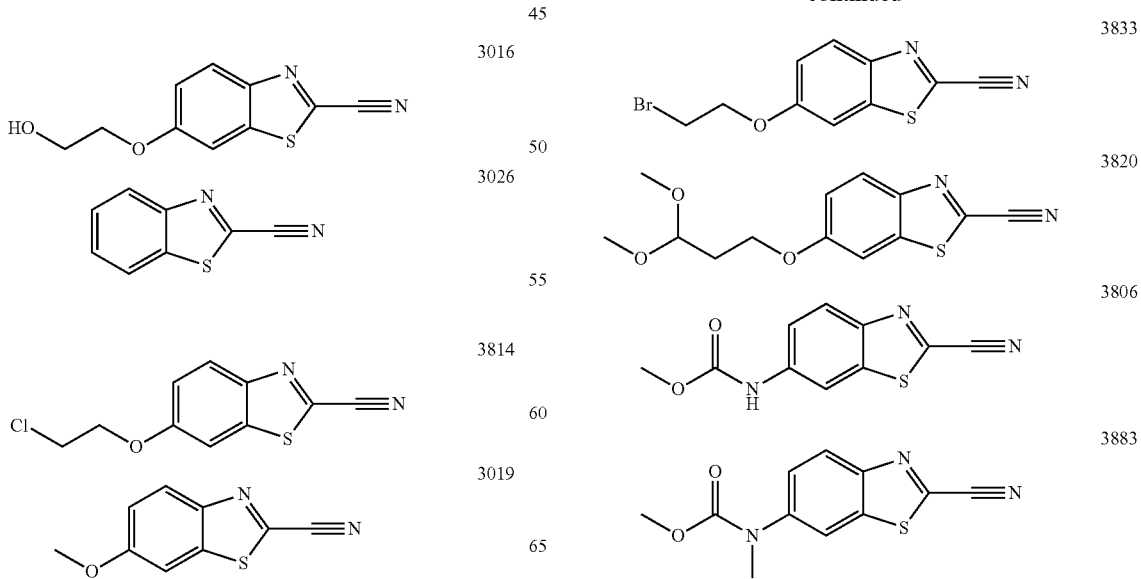

-continued

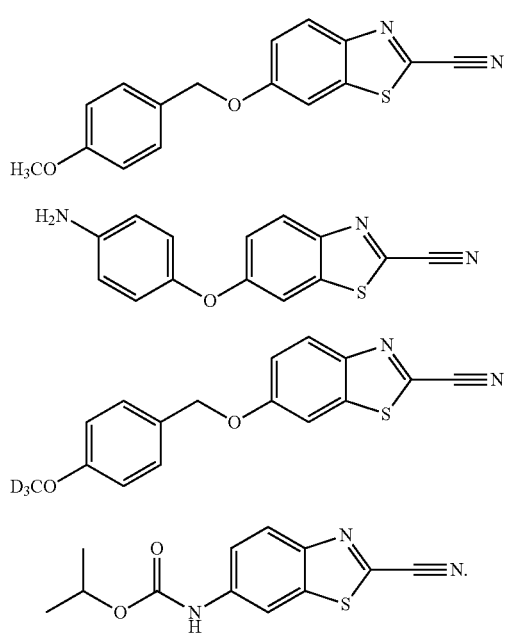

Alkyl or aryl groups of these compounds can be additionally or alternatively substituted with one or more (e.g., 1, 2, 3, 4, 5, or 6) substituents, as described above, and/or, for example, as described in the definition of the term 'substituted'.

IV. Linkers

A linker strategy may be employed for the A ring modified 2-amino-6-hydroxy-benzothiazole, to introduce a substrate for an enzyme of interest such as a deacetylase, deformylase, demethylase or other enzyme that can remove the L group of formula I (a substrate for that enzyme) to free the linker, yielding a product that in the presence of D-cysteine substrate of luciferase, where the remaining linker may optionally be removed by a nonenzymatic reaction.

Linkers can be alkyl or alkoxy chains, such as $(C_1-C_6)$alkyl or $(C_1-C_6)$alkoxy groups. The chain can have one or more electron withdrawing group substituents R, such as an aldehyde, acetyl, sulfoxide, sulfone, nitro, cyano group, or a combination thereof. Other linkers include trimethyl lock, quinine methide and diketopiperazine linkers, and their derivatives. A trimethyl lock linker can be illustrated as follows:

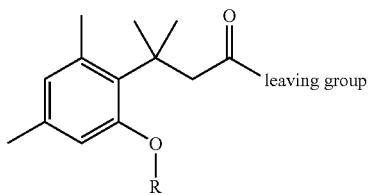

wherein R is as defined for any one of the Roman numeral formulas described herein, for example, formulas I-III, V, VII-IX, XI-XII, and XV, which is a group removable by an enzyme, e.g., an enzyme that is being assayed; the trimethyl lock linker replaces a hydrogen atom of one of the groups Z or Z'-R; and 'leaving group' is the remainder of the structure of formula I-III, V, VII-IX, XI-XII, and XV. See Wang et al., *J. Org. Chem.*, 62:1363 (1997) and Chandran et al., *J. Am. Chem. Soc.*, 127:1652 (2005) for the use of trimethyl lock linkers.

A quinine methide linker can be illustrated as follows:

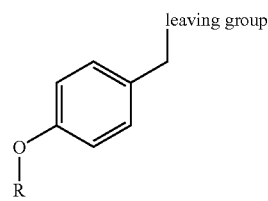

wherein R is as defined for any one of formulas I-III, V, VII-IX, XI-XII, and XV which is a group removable by an enzyme, e.g., an enzyme that is being assayed; the quinine methide linker replaces a hydrogen atom of one of the groups Z or Z'-R; and 'leaving group' is the remainder of the structure of formula I-III, V, VII-IX, XI-XII, and XV. See Greenwald et al., *J. Med. Chem.*, 42:3657 (1999) and Greenwald et al., *Bioconjugate Chem.*, 14:395 (2003) for the use of quinine methide linkers.

A diketopiperazine linker can be illustrated as follows:

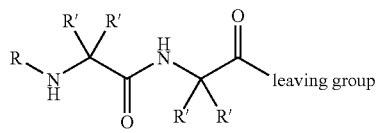

wherein R is as defined for any one of formulas I-III, V, VII-IX, XI-XII, and XV which is a group removable by an enzyme, e.g., an enzyme that is being assayed; each R' of the diketopiperazine linker is independently H or an alkyl chain optionally interrupted by O, S, or NH, preferably a methyl group; the diketopiperazine linker replaces a hydrogen atom of one of the groups Z or Z'-R; and 'leaving group' is the remainder of the structure of formula I-III, V, VII-IX, XI-XII, and XV. See Wei et al., *Bioorg. Med. Chem. Lett.*, 10: 1073 (2000) for the use of diketopiperazine linkers.

Other linker containing derivatives include:

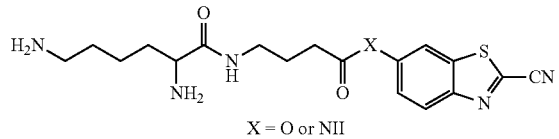

X = O or NH

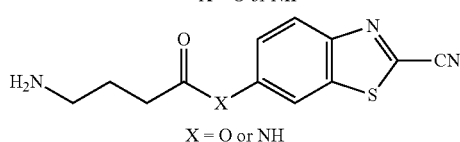

X = O or NH

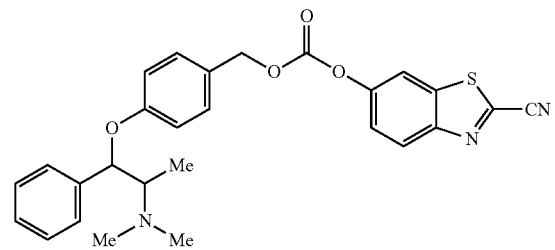

-continued

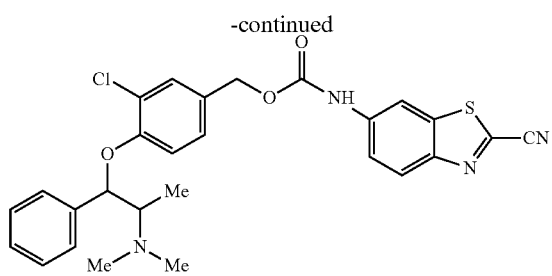

General Synthetic Methods

Preparation of the Compounds of Formulas I-XV can be Prepared from the Corresponding 2-halobenzothiazole, or may be prepared according to known techniques in the art of organic synthesis. Many 2,6-disubstituted benzothiazoles are commercially available, and/or can be prepared as described in the art. Information regarding general synthetic methods that may be used to prepare the compounds described herein may be found in Greg T. Hermanson, *Bioconjugate Techniques*, Academic Press, San Diego, Calif. (1996); March's *Advanced Organic Chemistry Reactions, Mechanisms, and Structure*, 5th Ed. by Michael B. Smith and Jerry March, John Wiley & Sons, Publishers; and Wuts et al. (1999), *Protective Groups in Organic Synthesis*, 3rd Ed., John Wiley & Sons, Publishers.

The methods of preparing compounds of the invention can produce isomers in certain instances. Although the methods of the invention do not always require separation of these isomers, such separation may be accomplished, if desired, by methods known in the art. For example, preparative high performance liquid chromatography methods may be used for isomer purification, for example, by using a column with a chiral packing.

The following Examples are intended to illustrate the above invention and should not be construed as to narrow its scope. One skilled in the art will readily recognize that the Examples suggest many other ways in which the present invention could be practiced. It should be understood that many variations and modifications may be made while remaining within the scope of the invention.

EXAMPLES

General Introduction to Examples 1-7

The invention includes a method of determining activity of the uridine 5'-diphospho-glucuronosyltransferase (UDP-glucuronosyltransferase, or UGT) family enzymes in vitro. Briefly, UGT enzymes from overexpressed insect microsomes (Supersomes™, BD Gentest™) or animal tissue microsomes (Xenotech, BD Gentest™) were incubated with a cyanobenzothiazole substrate of the invention and the cofactor UDP-glucuronic acid (UDPGA) at 37° C. in buffer at physiological pH containing MgCl$_2$ and alamethicin (typically, 50 mM TES, pH 7.5, 8 mM MgCl$_2$, 4 mM UDPGA (Sigma) and 25 μg/mL alamethicin (Sigma)). Following the UGT enzyme reaction, an equal volume of P450-Glo Luciferin Detection Reagent (Promega) containing 15-30 mM D-cysteine-HCl.H$_2$O (Sigma) was added and the plate was mixed and incubated at room temperature, typically for 20-30 minutes. P450-Glo Luciferin Detection Reagent can be prepared by dissolving a vial of Promega Luciferin Detection Reagent (Promega Part #V859B) with a vial of Promega P450-Glo Buffer (Promega Part #V865B).

During this incubation, the cysteine reacts with the cyanobenzathiozole substrate to yield a D-luciferin derivative. The presence of the luciferin derivative formed from the unmodified substrate results in light output in the presence of the P450-Glo Luciferin Detection Reagent, while any substrate that was glucuronidated by UGT does not initiate light output. Therefore, activity of the UGT enzyme can be measured by analyzing the difference (lower or no output) in relative light units (RLU) of a sample in which glucuronidation occurs compared to a sample that was run under the same conditions with no added UDPGA cofactor.

Example 1

Detection of UDP Glucuronosyltransferase (UGT) Activity with Compounds 3138, 3478, and 3165

In this example, a series of 12 recombinant UGTs expressed in insect microsomes (Supersomes™, BD Gentest™), as well as the control microsomes not expressing the UGT enzyme, were incubated with compound 3138, compound 3478, or compound 3165 as substrates, with or without the UDPGA co-factor.

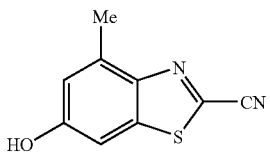
3138

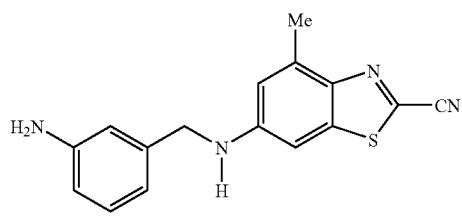
3165

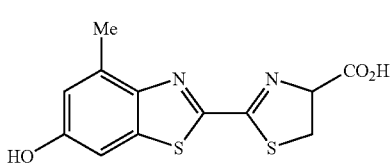
3478

Figure 3:
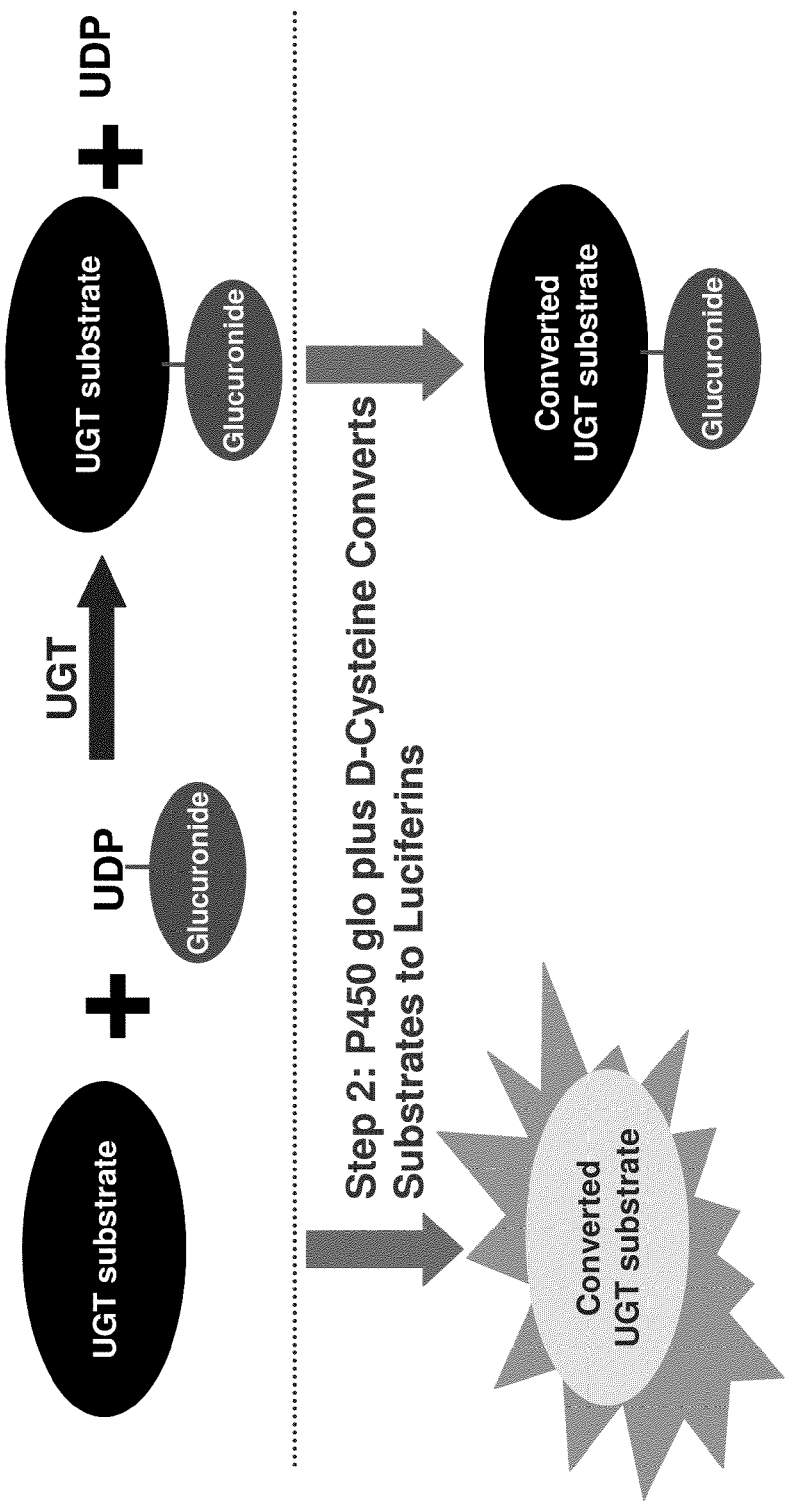
FIG. 3 is a schematic illustration of detecting UDP Glucuronosyltransferase (UGT) activity, according to an embodiment of the invention.

After addition of a luciferin detection reagent (LDR) containing D-cysteine, both the substrate and the product were converted to D-luciferins (compound 3478 is already a luciferin derivative before addition of the LDR). Only the unglucuronidated substrate produced light, as shown in FIG. 3, and any substrate glucuronidated by the enzyme does not produce light, resulting in a drop in relative light units (RLU) for that sample.

Reactions were assembled in a white 96-well plate. Each well contained 20 μL of reaction mixture comprised of 100 mM TES, pH 7.5, 16 mM MgCl$_2$, 50 μg/mL alamethicin (Sigma), 60 μM compound 3138 or compound 3478, and 0.4 mg/mL of control or recombinant UGT membranes. The reactions were started by addition of 20 μL of water or 8 mM triammonium UDPGA (Sigma) to each well. The plate was mixed, sealed, and incubated in a 37° C. water bath for 2 hours. After the incubation, 40 μL P450-glo LDR (Promega) with 20 mM D-cysteine-HCl.H$_2$O (Sigma) was added to each well, the plate was mixed and allowed to incubate at room temperature for 20 minutes. After the incubation was completed, the plate was read on a Veritas™ luminometer (Turner BioSystems, Inc.; Sunnyvale, Calif.).

For each isozyme, the plus UDPGA replicates were subtracted from the average minus UDPGA RLU. The average Δ RLU value obtained and the standard deviation of the replicates are then divided by the average minus UDPGA RLU to obtain the % utilization for each isozyme. The % utilization obtained from the control microsomes was then subtracted from each isozyme to give the background corrected utilization data for those isozymes.

Figure 4:
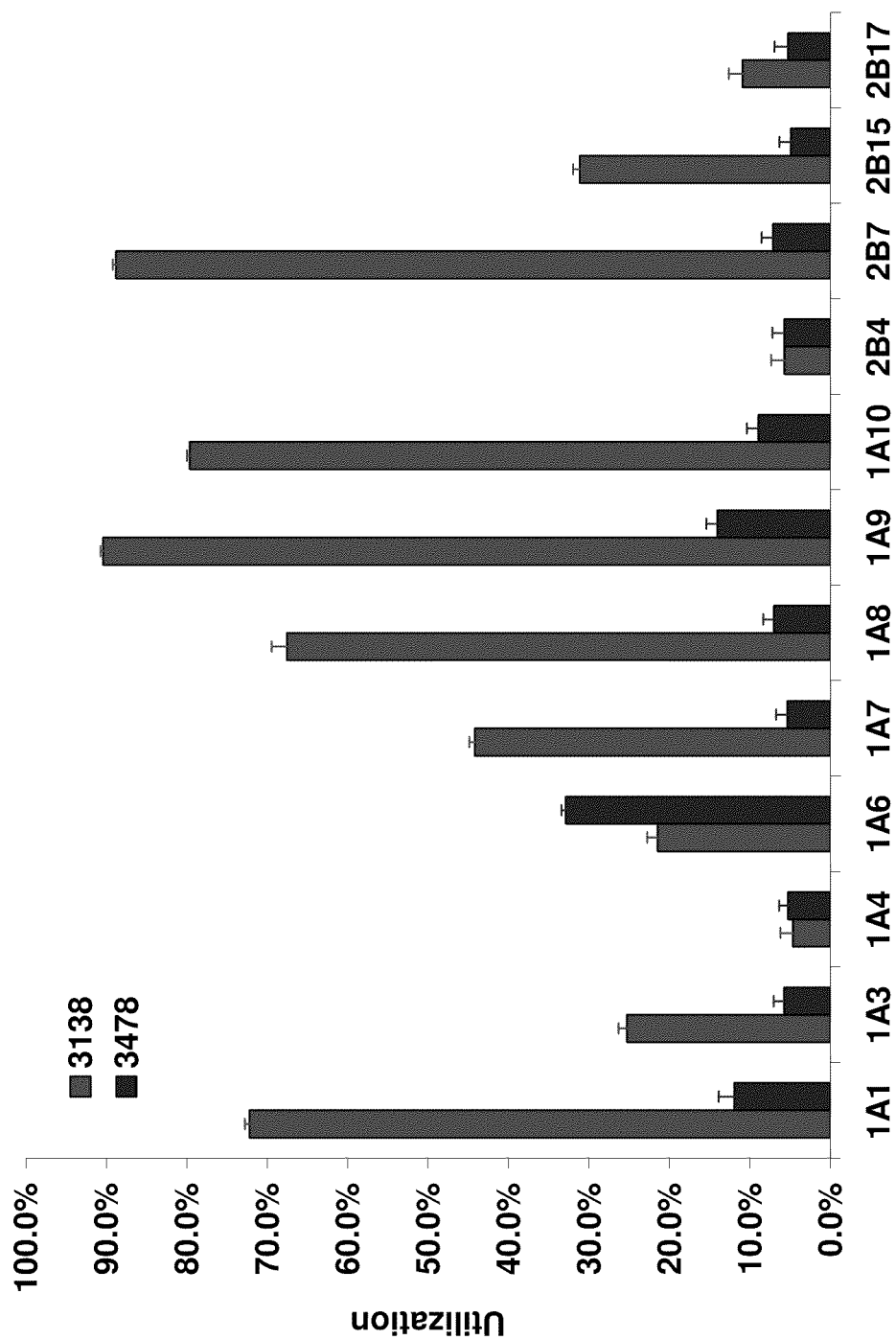
FIG. 4 illustrates the activity data for 12 isozymes, with respect to the utilization of compounds 3138 and 3478, according to an embodiment.
Figure 5:
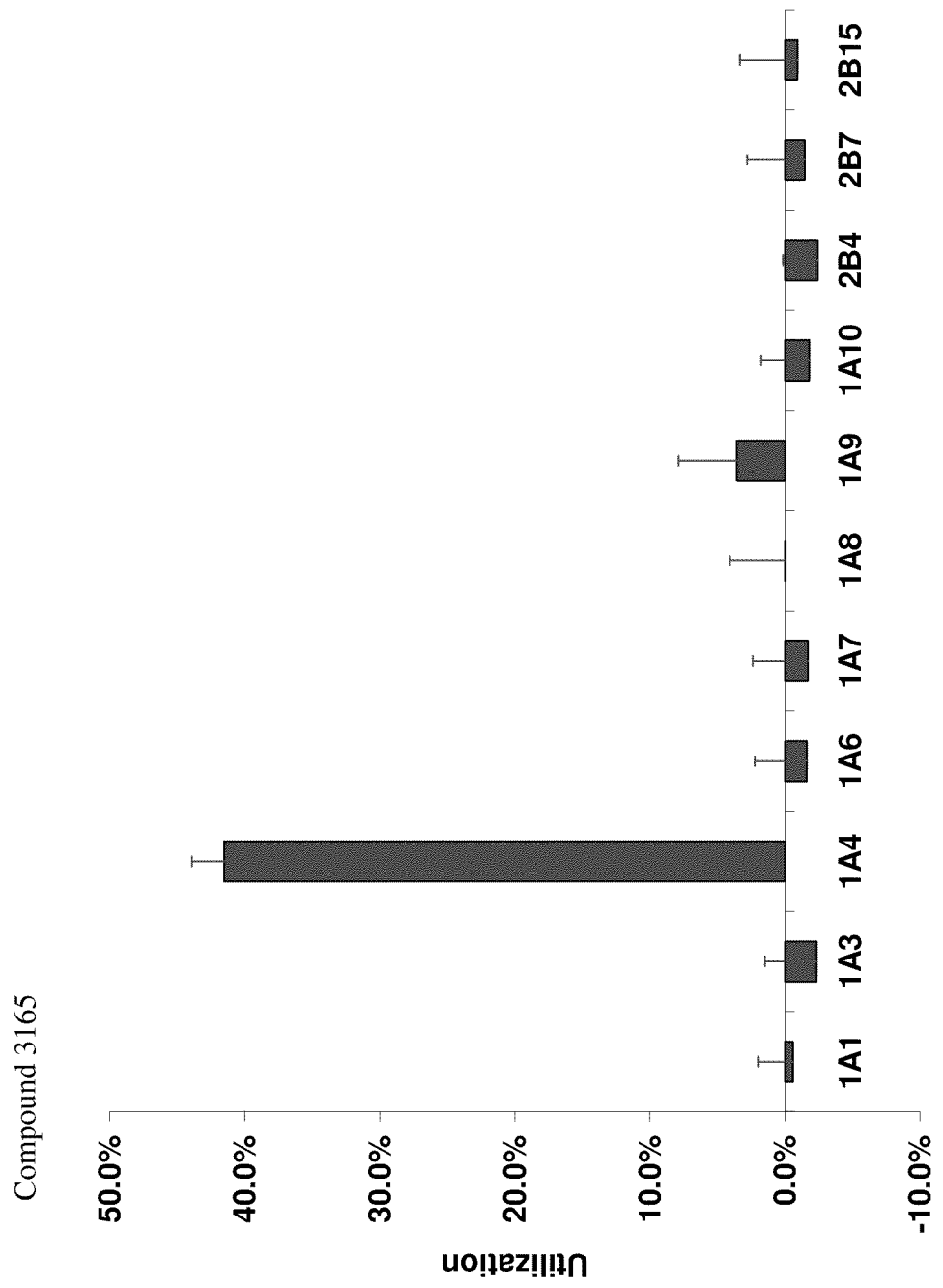
FIG. 5 illustrates the activity data for 12 isozymes, with respect to the utilization of compound 3165, according to an embodiment.

Activity data for these 12 isozymes are shown in FIGS. 4 and 5. The major UGT isozymes 1A1, 1A8, 1A9, 1A10, and 2B7 all utilized over 50% of compound 3138 during the 2 hour incubation. These same isozymes utilized 15% or less of the compound 3478, the luciferin analog of compound 3138, demonstrating the need to use a pre-luciferin to measure these enzymes. Although compound 3138 utilization was less for UGT 1A3, 1A6, 1A7, 2B15, and 2B17, there were still detectable levels of utilization above background. The utilization of compound 3138 by these compounds could be further optimized by modulating reaction time, concentration of microsomal enzyme, and/or concentration of compound 3138. Of this second set of isozymes, only UGT 1A6 was able to utilize compound 3478 to any appreciable extent. UGT 1A4 and 2B4 did not utilize either compound 3138 or 3478 to an appreciable extent as substrates. Compound 3165 was only utilized by UGT 1A4, and to a lesser extent, UGT 1A9 (FIG. 5).

Example 2

Utilization of Compounds 3138 and 3165 by Mammalian Microsomes

The ability of endogenously expressed UGT isozymes to utilize compounds 3138 and 3165 as substrates was determined in a similar manner to the assays with recombinant microsomes (Example 1). With compound 3138, reactions were run for 15 minutes at 37° C. in 50 mM TES, pH 7.5, 8 mM $MgCl_2$, 25 µg/mL alamethicin, 0.1 mg/mL mammalian microsomes or 0.2 mg/mL recombinant Supersomes, and 50 µM compound 3138, plus or minus 4 mM UDPGA (test reaction and control, respectively). With compound 3165, reactions were run for 2 hours at 37° C. in 50 mM TES, pH 7.5, 8 mM $MgCl_2$, 25 µg/mL alamethicin, 0.2 mg/mL mammalian microsomes or recombinant Supersomes, and 50 µM compound 3165, plus or minus 4 mM UDPGA (test reaction and control, respectively). Tissue microsomes were obtained from Xenotech LLC or BD Gentest. Addition of LDR plus cysteine and data analysis was performed in the same manner as for the recombinant Supersome panel screen (Example 1 above).

Figure 6:
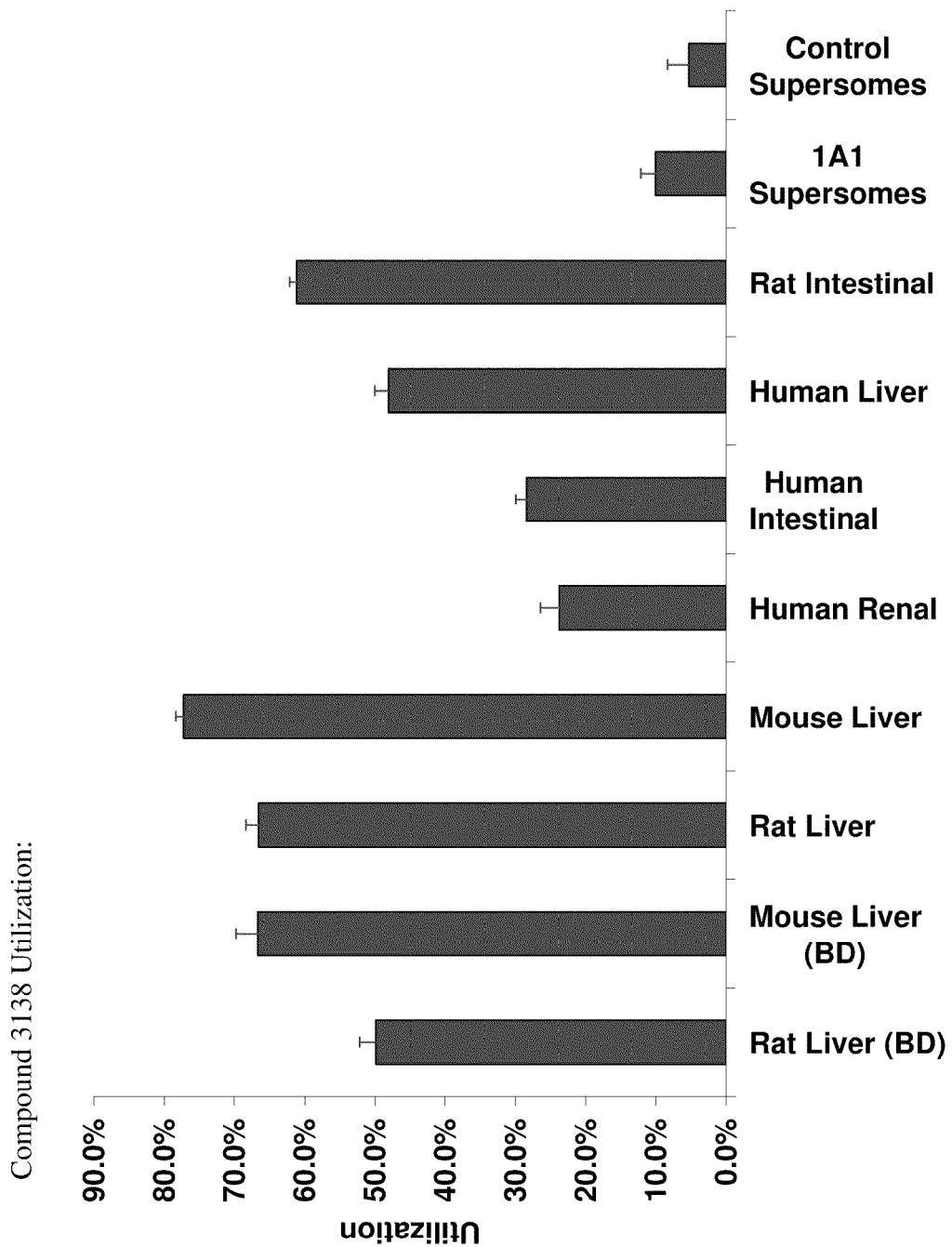
FIG. 6 illustrates utilization of compounds 3138 by mammalian microsomes.

Utilization of compound 3138 was rapid and the reaction had to be cut short at 15 minutes in order to see the differences between the different tissues and animals. All tissues tested utilized much more compound 3138 than the control 1A1 Supersomes (FIG. 6). This result is not unexpected as the concentration of UGT 1A1 in Supersomes, although derived from cells overexpressing the protein, is not likely higher than the additive concentration of all isozymes capable of using compound 3138 in the tissue samples. In addition, recent reports indicate that UGT isozymes may have more than additive activity when expressed together in a single membrane.

Figure 7:
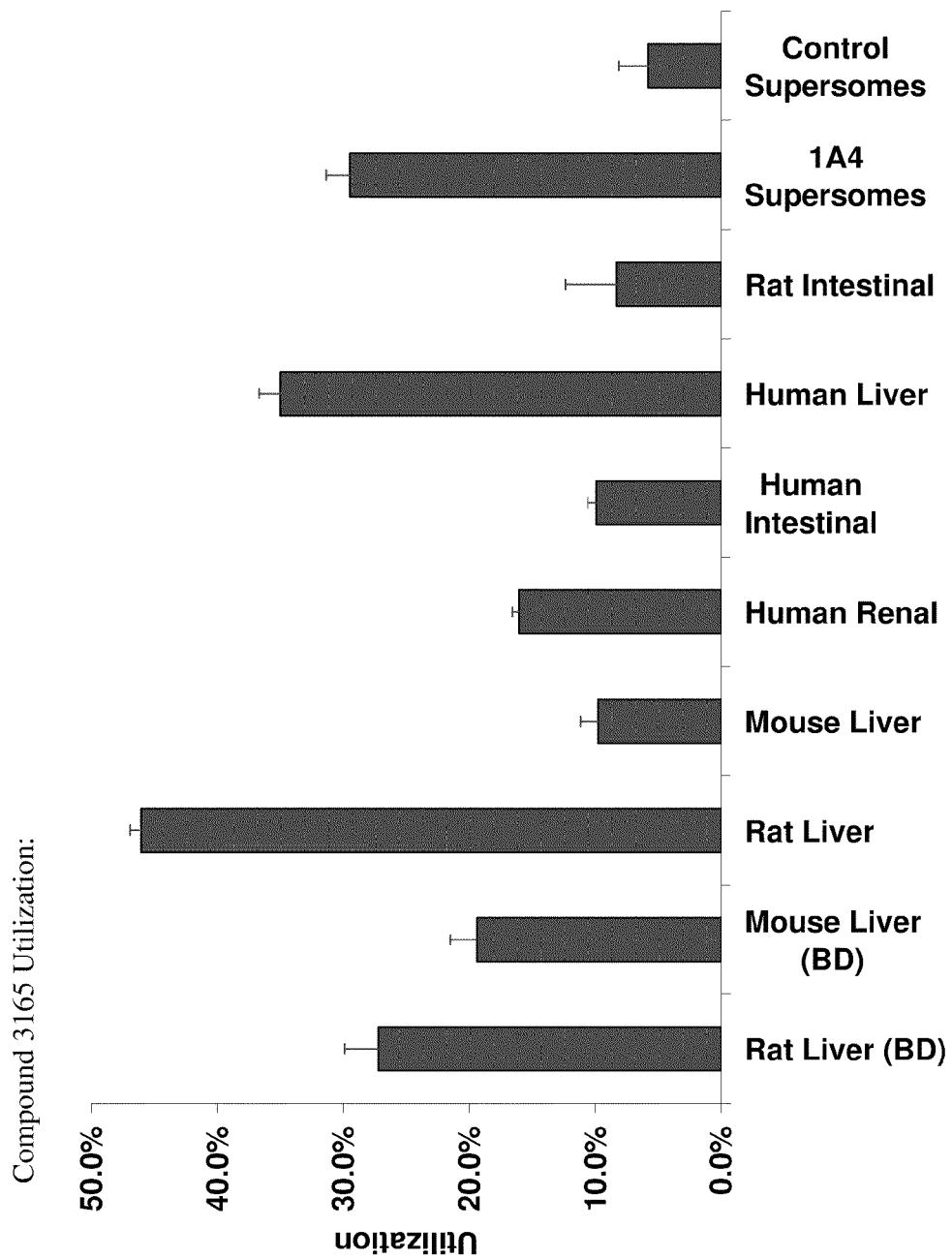
FIG. 7 illustrates utilization of compounds 3165 by mammalian microsomes.

Utilization of compound 3165 was much slower, consistent with its use by mainly one isozyme (UGT 1A4, or similar activities from rats or mice) (FIG. 7). Accordingly, reactions were run for 2 hours. Activity was much higher for human liver microsomes than either human renal or human intestinal microsomes, consistent with reports that expression of UGT 1A4 is higher in liver than in extra-hepatic tissues. Activity was also seen for both rat and mouse liver microsomes.

Example 3

Measuring Inhibition of Recombinant UGT Isozymes by Ritonavir with Compounds 3138 and 3165

It was reported in the literature that the HIV protease inhibitor ritonavir inhibits UGT 1A 1 and 1A4, but has little effect on UGT 2B7. To test this observation in the current system, compound 3138 was used to probe UGT 1A1 and 2B7 Supersomes and compound 3165 was used to probe UGT 1A4 Supersomes. Reactions with compound 3138 were carried out in 50 mM TES, pH 7.5, 8 mM $MgCl_2$, 25 µg/mL alamethicin, 0.2 mg/mL Supersomes, 50 µM compound 3138, and 0-162 µM ritonavir (AK Scientific), plus or minus 5 mM UDPGA. After 2 hours at 37° C., 10 µL of 50 mM D-cysteine-$HCl.H_2O$ diluted in 200 mM HEPES, pH 8.0 was added to each 40 µL UGT reaction. After 10 minute incubations, 50 µL P450-glo (Promega) was added to each well and luminescence was measured. Reactions with compound 3165 were run in a similar manner using 25 µM 3165, except reactions were only incubated at 37° C. for 70 minutes and with concentrations of ritonavir up to 40 µM.

Figure 8:
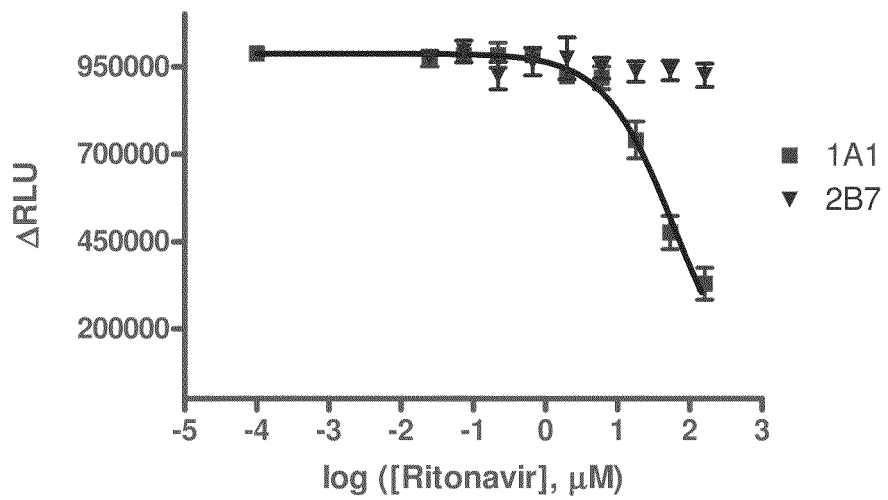
FIG. 8 illustrates inhibition of various isozymes by ritonavir using compound 3138 by a method described herein.
Figure 9:
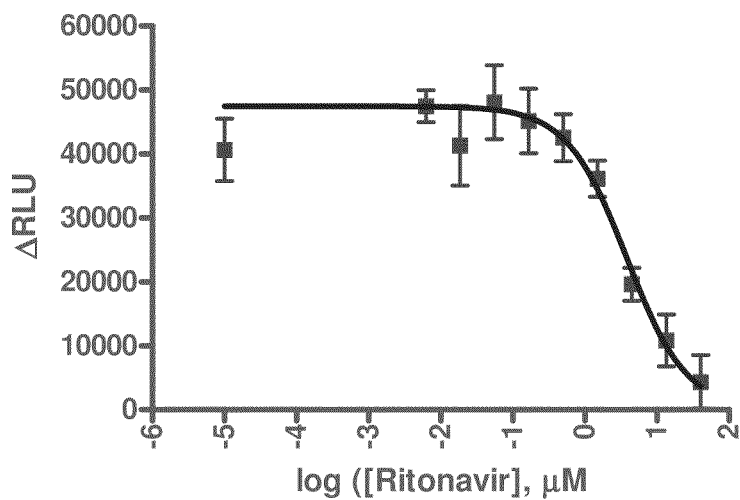
FIG. 9 illustrates inhibition of various isozymes by ritonavir using compound 3165 by a method described herein.

Results with compounds 3138 and 3165 are shown in FIGS. 8 and 9, respectively. Ritonavir inhibits UGT 1A1 and UGT 1A4, but not UGT 2B7, which is in agreement with the literature. Measurements indicated $EC_{50}$ values of 60 µM for UGT 1A1 and 4 µM for UGT 1A4. This result shows the ability of the assay system to identify inhibitors of specific UGT isozymes using recombinant Supersomes.

Example 4

Inhibition of Recombinant UGT Isozymes and UGT Activities in Human Liver Microsomes with Diclofenac Diclofenac is a non-steroidal anti-inflammatory drug (NSAID) that is a known substrate for many of the UGT enzymes and is also reported to inhibit UGT 1A1, 1A3, 1A6, 1A7, 1A8, 1A9, 1A10, 2B7, 2B15, and 2B17. Its broad inhibitory activity against most UGT isozymes made it an ideal candidate to probe inhibition of UGT activities in both recombinant UGT preparations and human liver microsomes (HLM).

To asses the ability of diclofenac to inhibit recombinant UGTs, reactions were set up using UGT 1A1 and 2B7 supersomes. These reactions contained 50 mM TES, pH 7.5, 8 mM $MgCl_2$, 25 µg/mL alamethicin, 0.1 mg/mL Supersomes™, and 20 µM compound 3138, plus or minus 4 mM UDPGA. The titration was performed over 0-10 mM diclofenac. After 90 minutes at 37° C., 40 µL of LDR plus 20 mM D-cysteine was added to each 40 µL reaction and mixed. After 20 minutes at room temperature, RLU were read on a luminometer.

To assess the ability of diclofenac to inhibit UGT activity in HLM, reactions were set up as follows. All reactions contained 50 mM TES, pH 7.5, 8 mM $MgCl_2$, 25 µg/mL alamethicin, 0.1 mg/mL HLM, and 50 µM compound 3138, plus or minus 4 mM UDPGA. The titration was performed over 0-3.6 mM diclofenac. After 15 minutes at 37° C., 40 µL of LDR plus 20 mM D-cysteine was added to each 40 µL reaction and mixed. After 20 minutes at room temperature, RLU were read on a luminometer.

Figure 10:
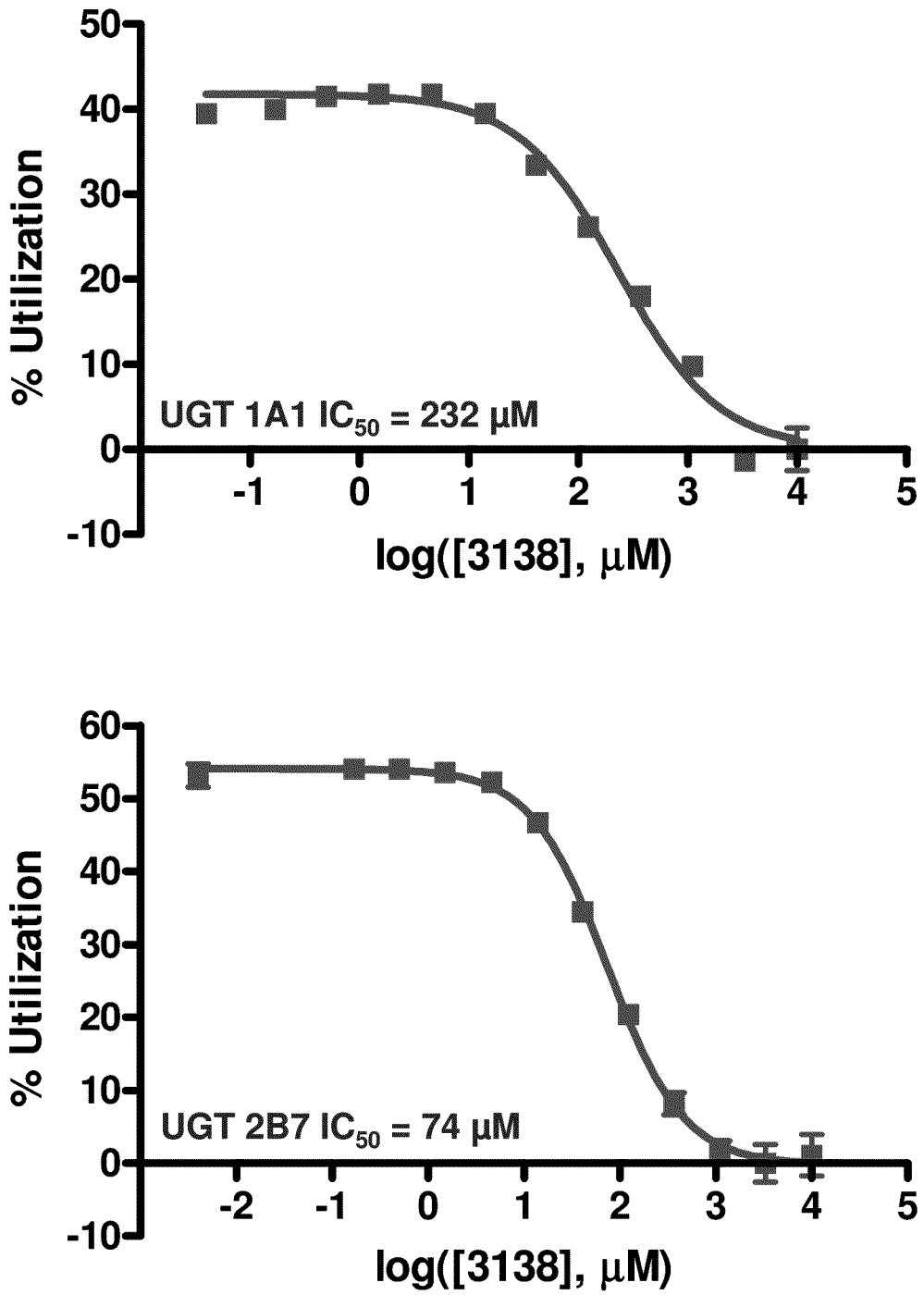
FIG. 10 illustrates a titration curves for UGT 1A1 (top) and UGT 2B7 (bottom) with the respective $IC_{50}$ values, according to an embodiment.
Figure 11:
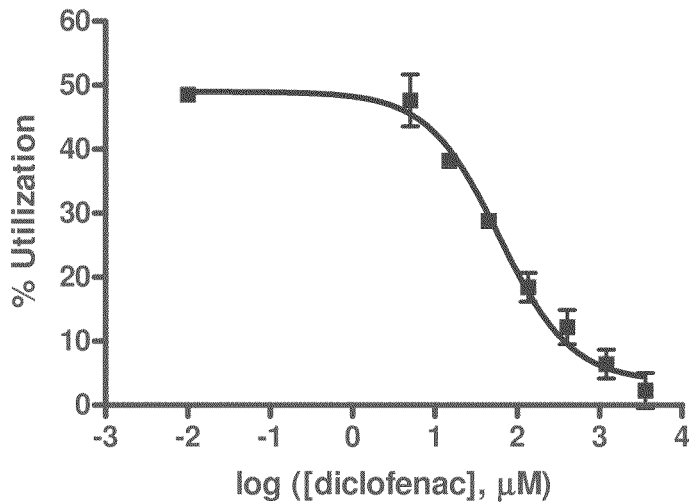
FIG. 11 illustrates inhibition of HLM utilization of compound 3138 by diclofenac with an $EC_{50}$ of 60 µM, according to an embodiment.

The titration curves are shown in FIGS. 10 (for recombinant supersomes) and 11 (for HLM). Diclofenac inhibited UGT 1A1 activity with an $IC_{50}$ of 232 µM and UGT 2B7 activity with an $IC_{50}$ of 74 µM. This is consistent with literature reports that UGT 2B7 is inhibited more potently than UGT 1A1 by diclofenac when using 4-methyl-umbelliferone as the substrate (see Uchaipichat et al. *Drug Metab. Disp.* (2004). 32:4, 413-423). Diclofenac inhibited HLM utilization of compound 3138 with an $EC_{50}$ of 60 µM. This example shows the utility of the assay for screening for inhibition using both recombinant UGT supersome preparations and the more native human liver microsome environment.

Example 5

Inhibition of Ugt Activities in Human Liver Microsomes

Many compounds are known to modulate the activity specific UGT isozymes. Several of these were tested in the assay system described herein to measure their ability to inhibit UGT activity in human liver microsomes (HLM) as measured using compound 3138. The inhibitor compounds, as well as a listing of isozymes currently reported in the literature to be modulated by the compound, are show in the table below.

| Compound | Isozymes Modulated |
| --- | --- |
| Sulfinpyrazone | 1A1, 1A7, 1A8, 1A9, 1A10, others to a lesser extent |
| Quinidine | 2B7 and 2B15, others to a lesser extent |
| 1-Naphthol | 1A1, 1A4, 1A6, 1A9 |
| Scopoletin | 1A3, 1A8, 1A9, 1A10, 2B17 |
| Androsterone | 1A1, 1A3, 1A4, 1A9, 1A10, 2B4, 2B7, 2B15 |
| Umbelliferne | Substrate of most isozymes |
| 7-hydroxy-4-trifluoro-methyl coumarin | Substrate for 1A1, 1A3, 1A6, 1A9, 2B7 |
| Ritonavir | 1A1, 1A3, 1A4 |
| Lopinavir | 1A1, 1A3, 1A4 |
| Diclofenac | Inhibits most isozymes |
| Valproate | 2B7 and 2B15, some others to a lesser extent |

To assess the ability of these compounds to inhibit UGT activity in HLM, reactions were set up as follows. All reactions contained 50 mM TES, pH 7.5, 8 mM $MgCl_2$, 25 µg/mL alamethicin, 0.05 mg/mL HLM, and 50 µM compound 3138, plus or minus 4 mM UDPGA. Ritonavir and lopinavir were used at a final concentration of 0.25 mM. Sulfinpyrazone, quinidine, and androsterone were used at 0.5 mM. 1-Naphthol, scopoletin, umbelliferne, and 7-hydroxy-4-trifluoromethyl coumarin were used at 1 mM. Diclofenac was used at 5 mM. Valproate was used at 10 mM. All reactions were compared to their corresponding vehicle control sample containing either water, DMSO, or ethanol. After 15 mM at 37° C., 40 µl, of LDR plus 20 mM D-cysteine was added to each 40 µl, reaction and mixed. After 20 minutes at room temperature, RLU were read on a luminometer.

Figure 13:
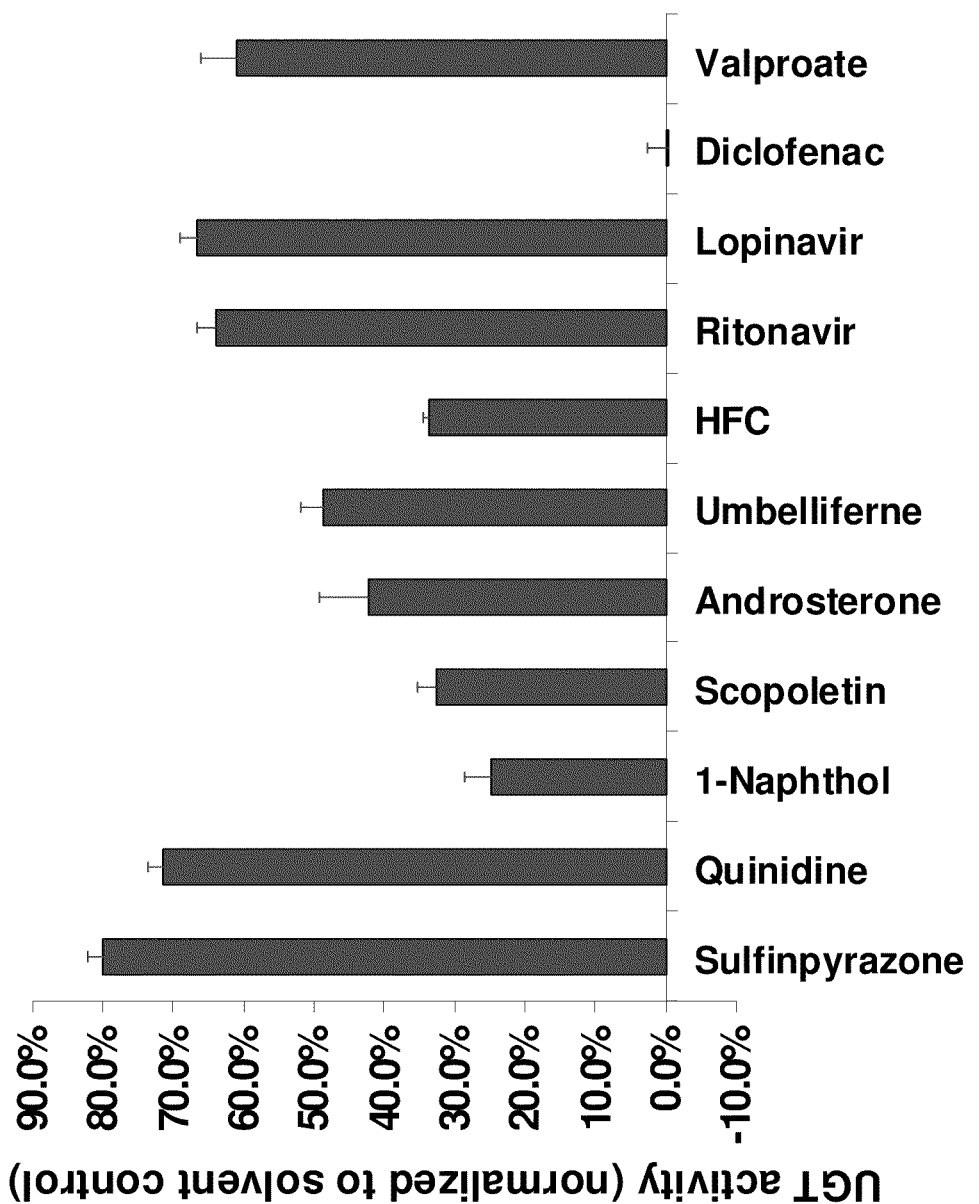
FIG. 13 illustrates inhibition of UGT activity in HLM by various compounds, according to an embodiment.
Figure 14:
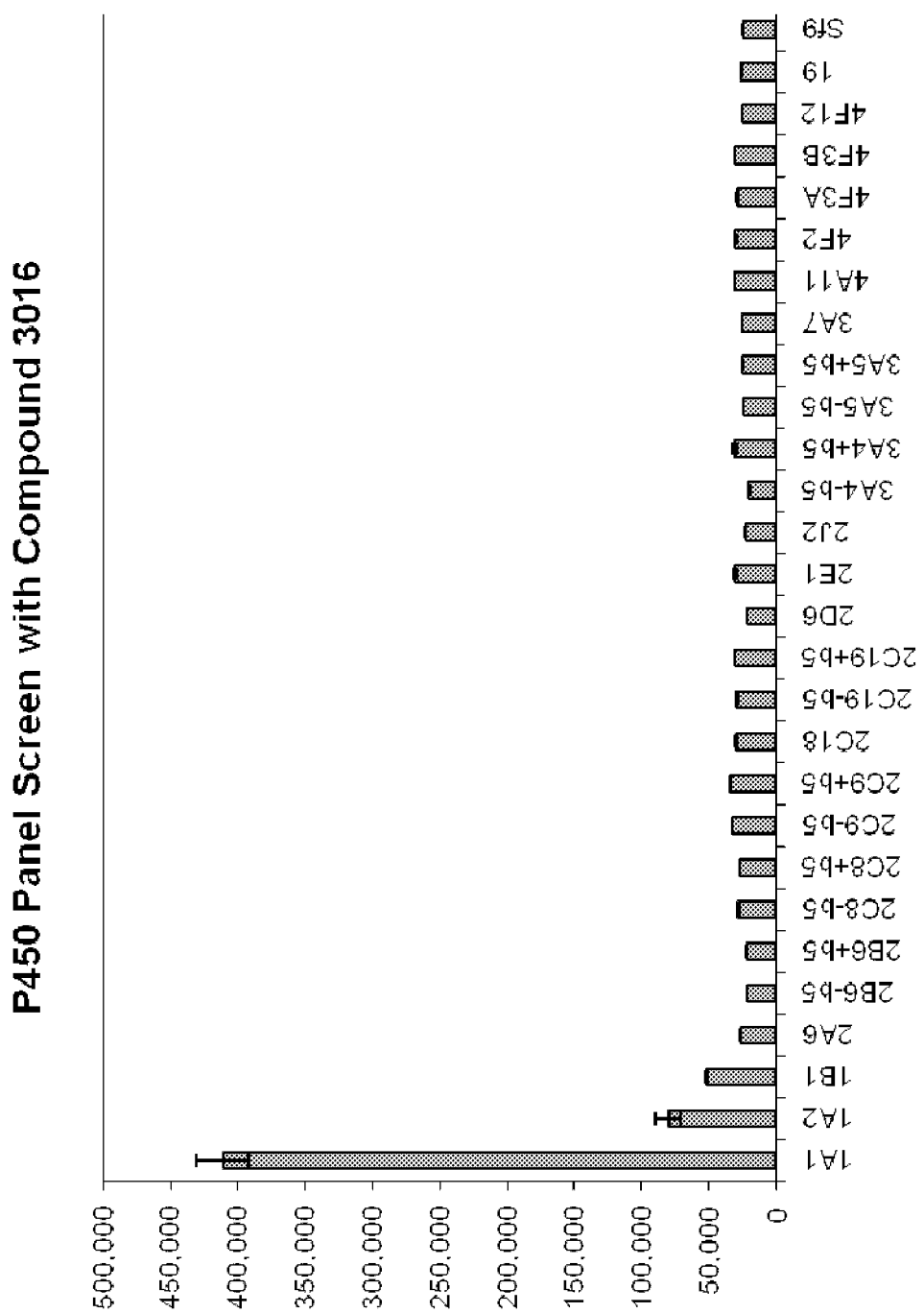
FIGS. 14-25 illustrate the selective detection of CYP450 enzyme activity as light output (recorded by a Veritas™ luminometer), as described by Example 9, for benzothiazole derivative compounds 3016, 3019, 3026, 3806, 3814, 3820, 3821, 3833, 3835, 3866, and 3868, according to an embodiment. The X-axis indicates relative light units (RLU).
Figure 15:
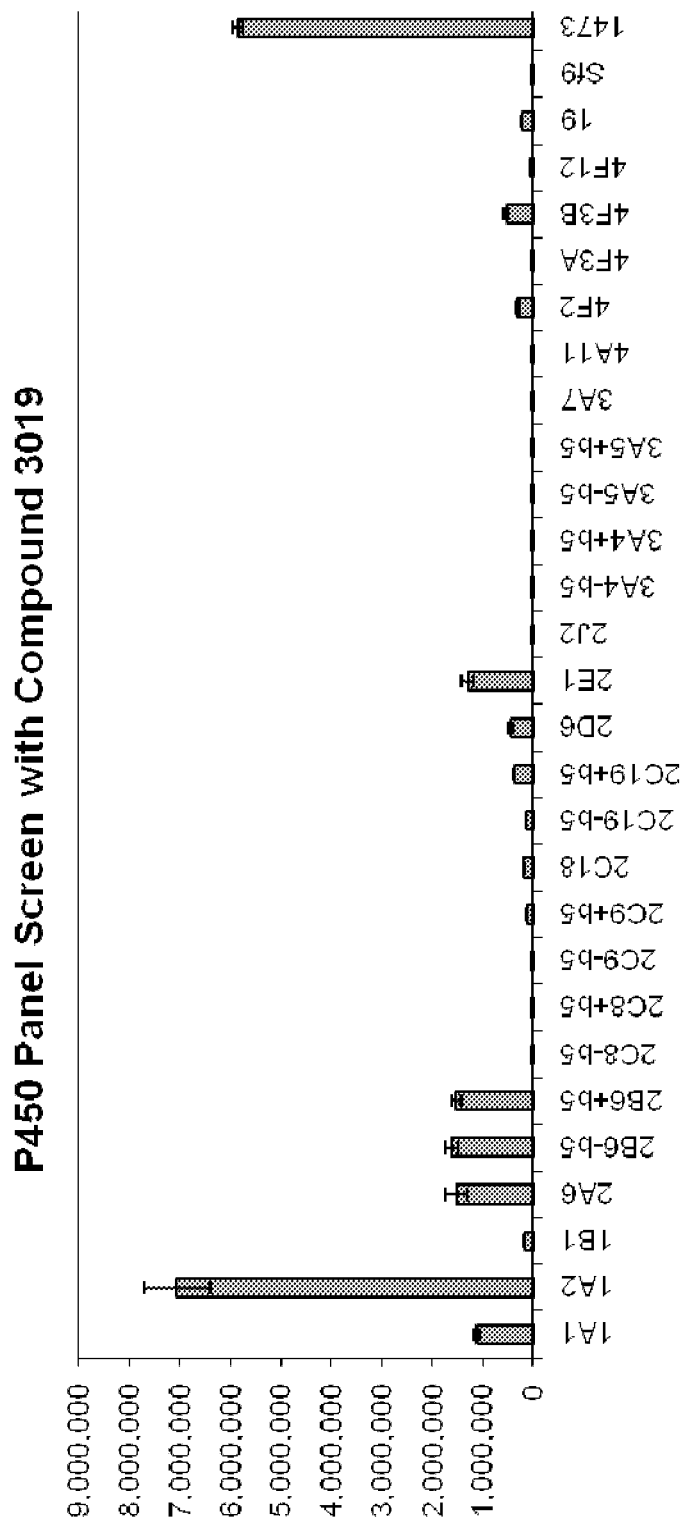
Figure 16:
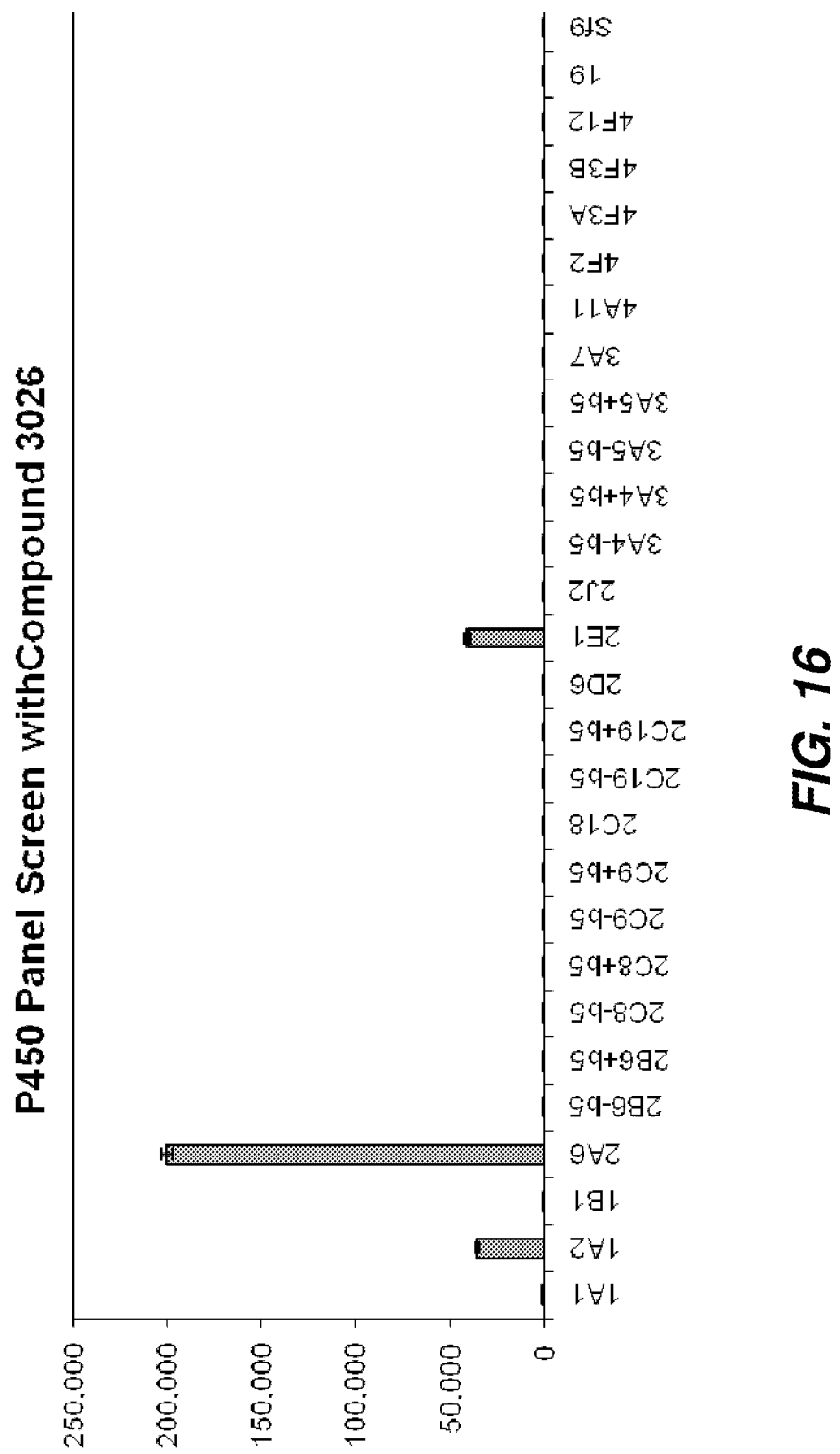
Figure 17:
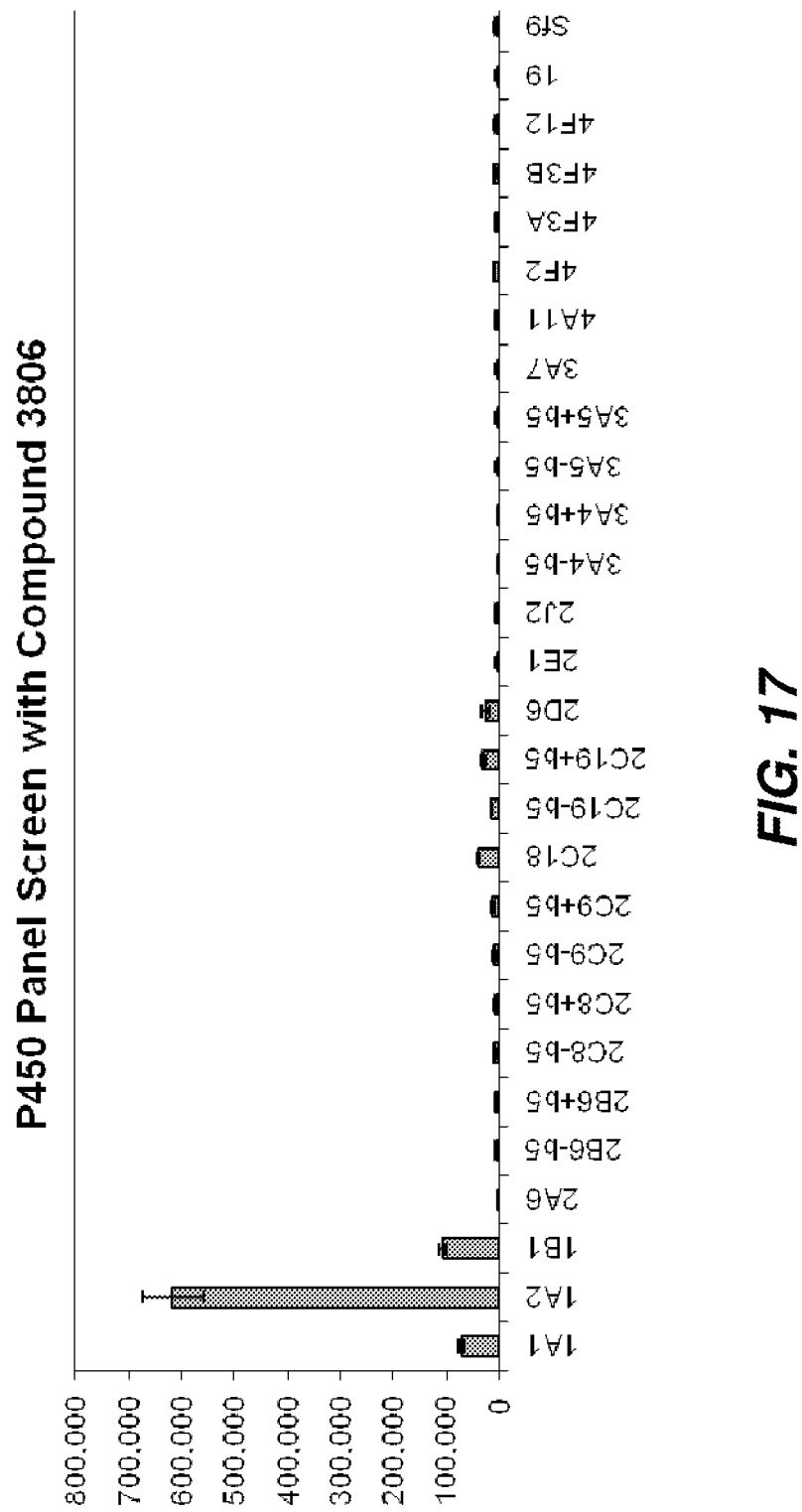
Figure 18:
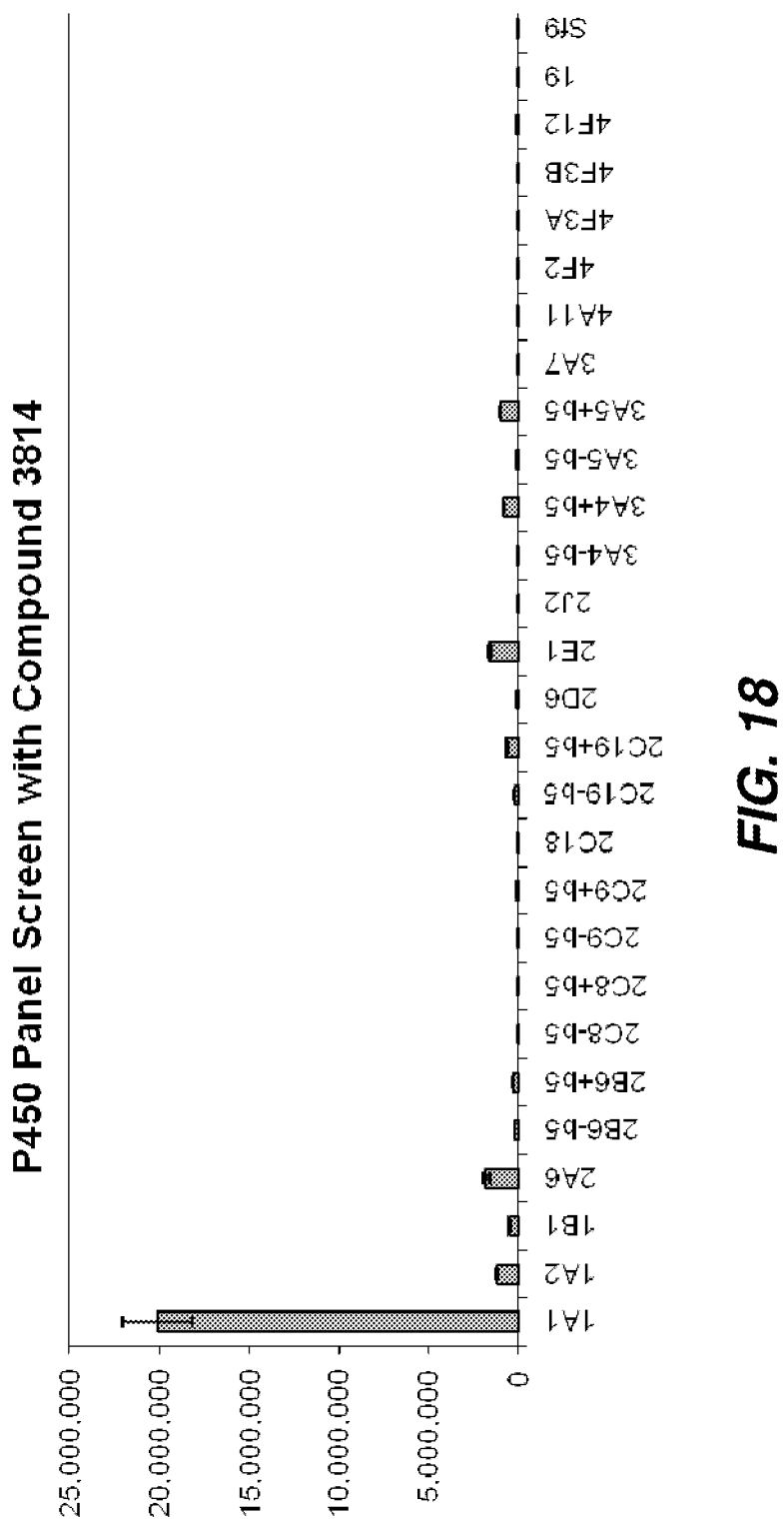
Figure 19:
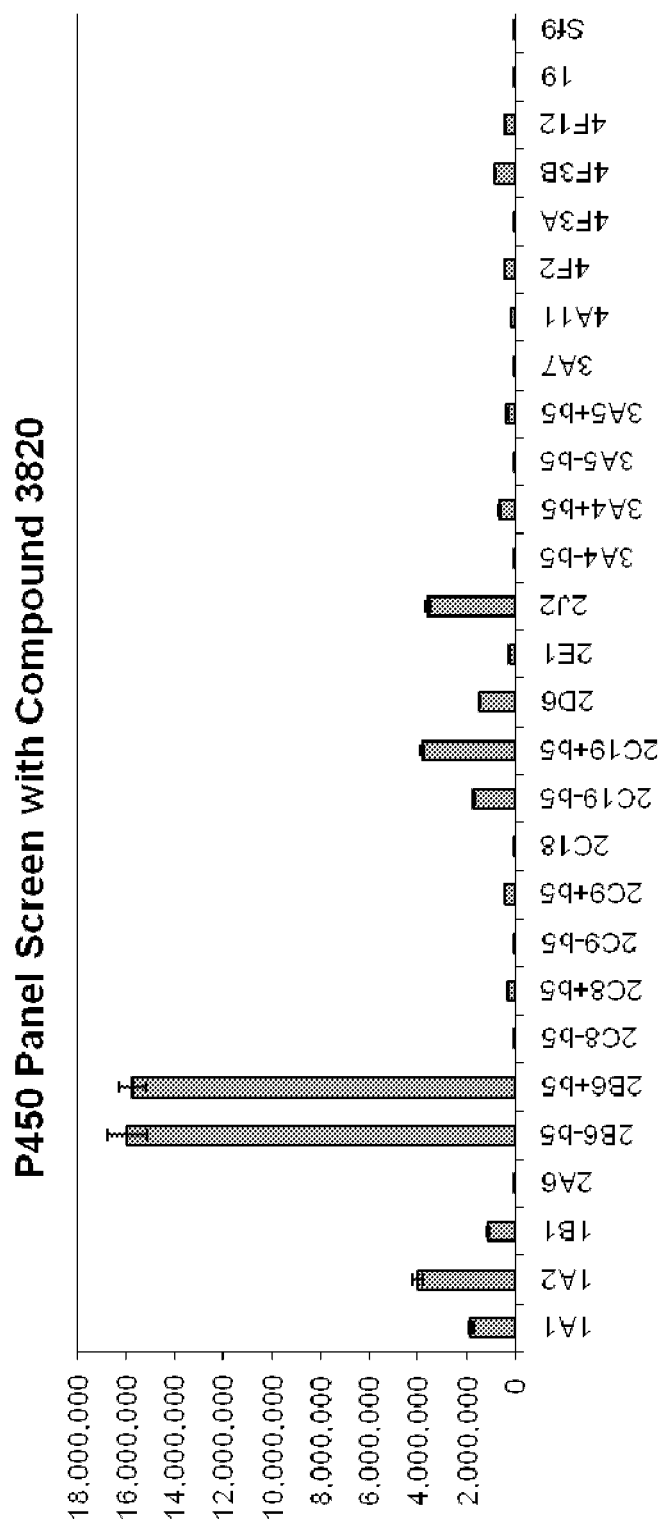
Figure 20:
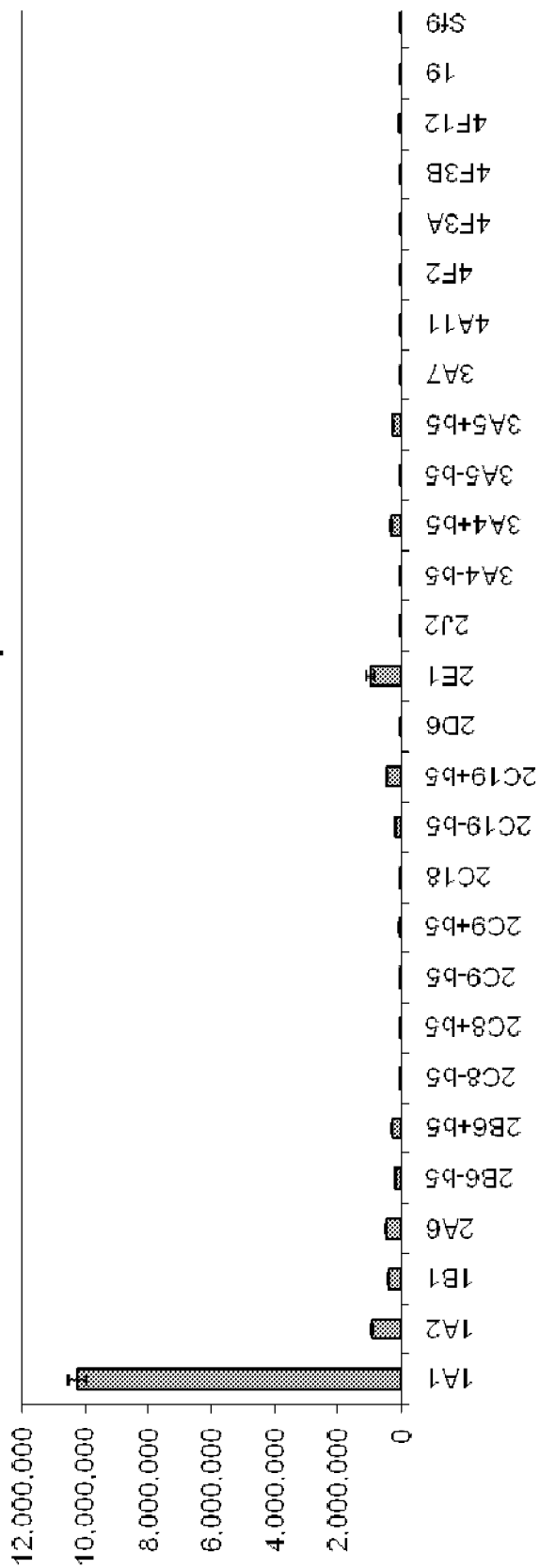
Figure 21:
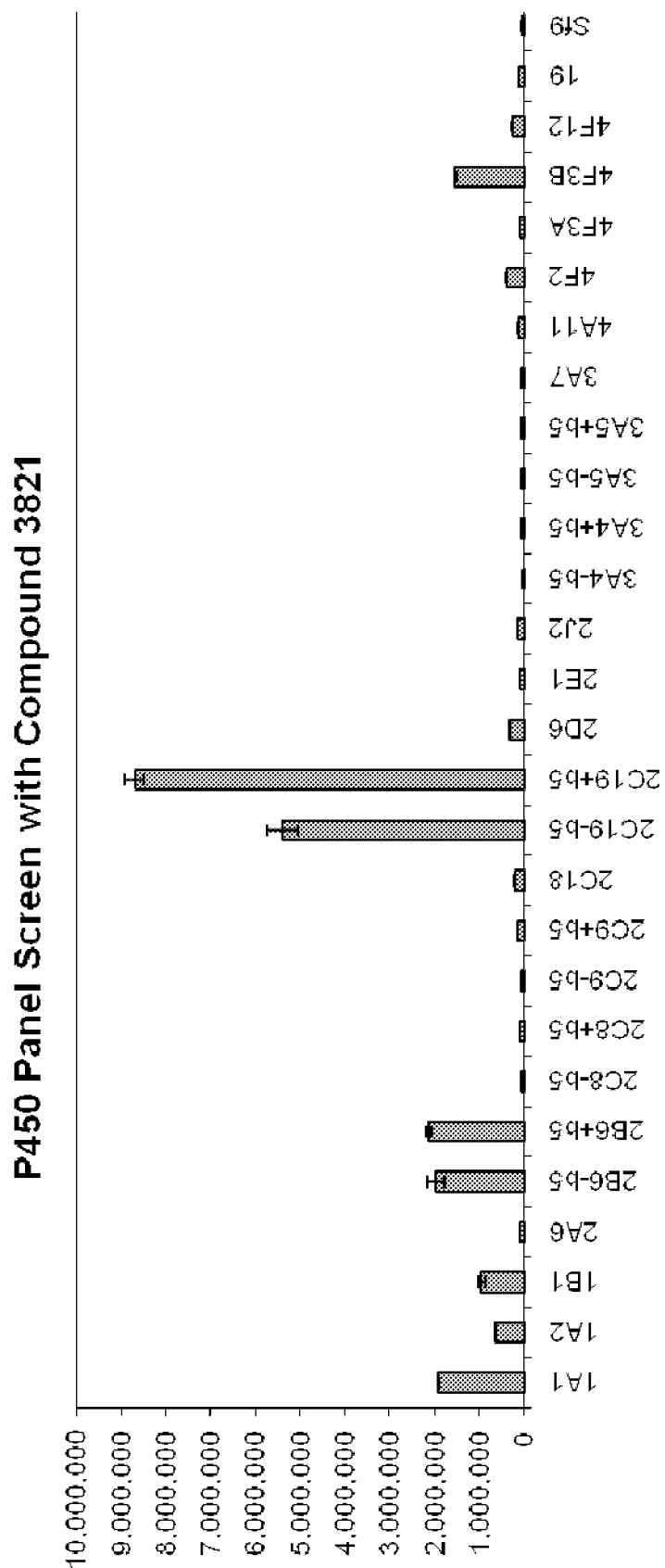
Figure 22:
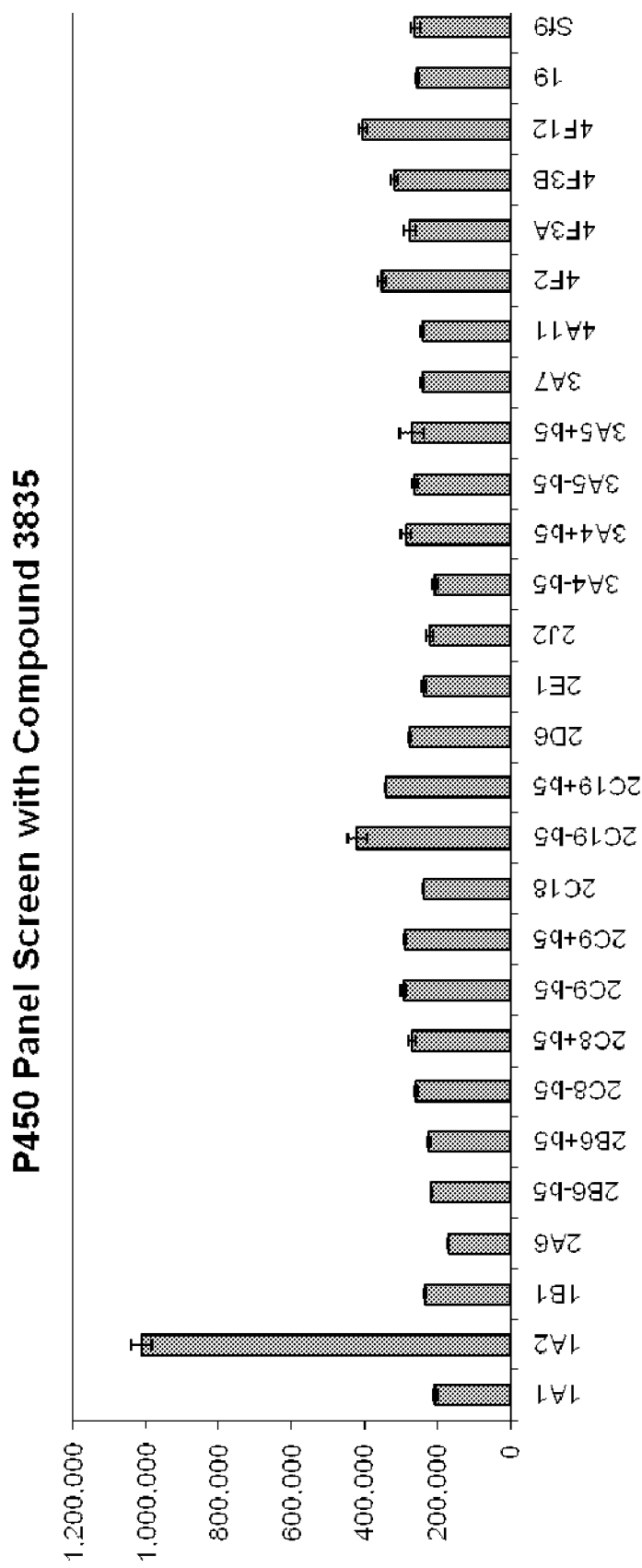
Figure 23:
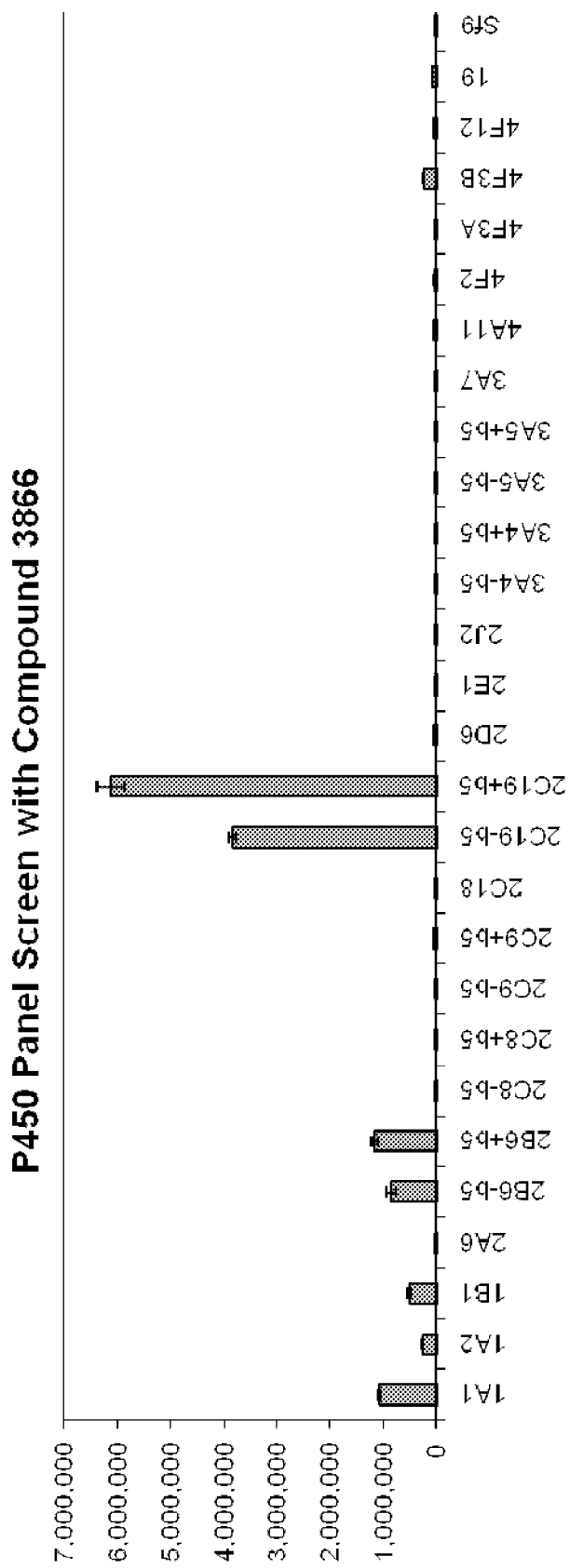
Figure 24:
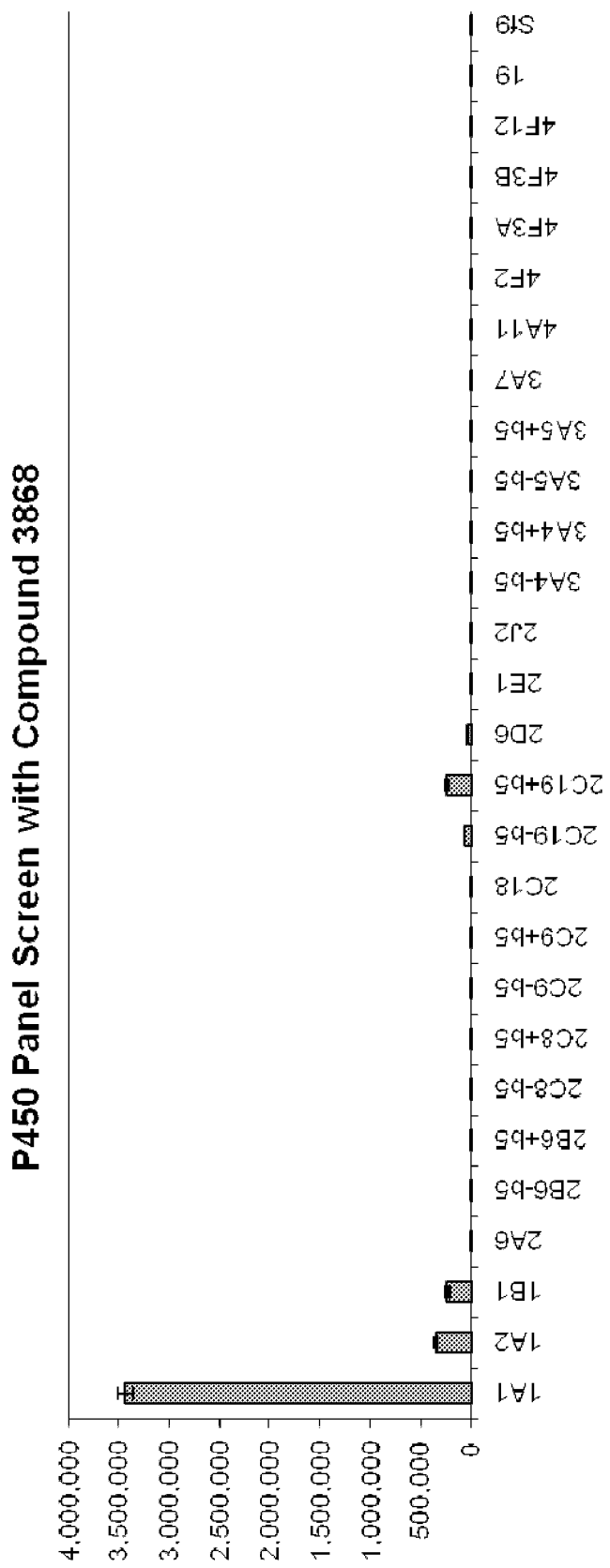
Figure 25:
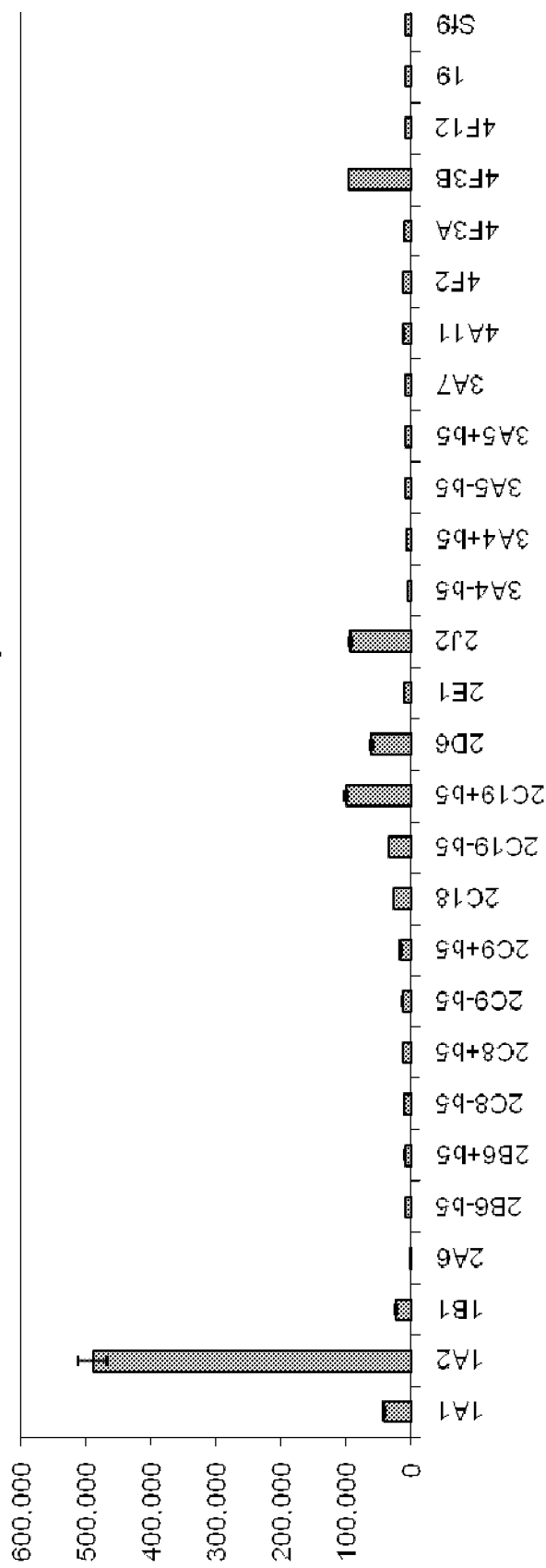

The compounds inhibited UGT activity in HLM to various degrees (FIG. 13). This example shows the utility of the assay for screening for a variety of UGT inhibitors in the more native human liver micro some environment.

Example 6

Determination of Assay Variability Using UGT 1A1 and 2B7

Assay variability was determined using the activity data and standard deviations of 12 separate minus UDPGA and plus UDPGA samples. All reactions contained 50 mM TES, pH 7.5, 8 mM $MgCl_2$, 25 µg/mL alamethicin, 0.2 mg/mL UGT 1A1 or 2B7 Supersomes™, and 30 µM compound 3138, plus or minus 5 mM UDPGA. After 120 mM at 37° C., 40 µl, of LDR plus 20 mM D-cysteine was added to each 40 µl, reaction and mixed. After 20 minutes at room temperature, RLU were read on a luminometer.

Figure 12:
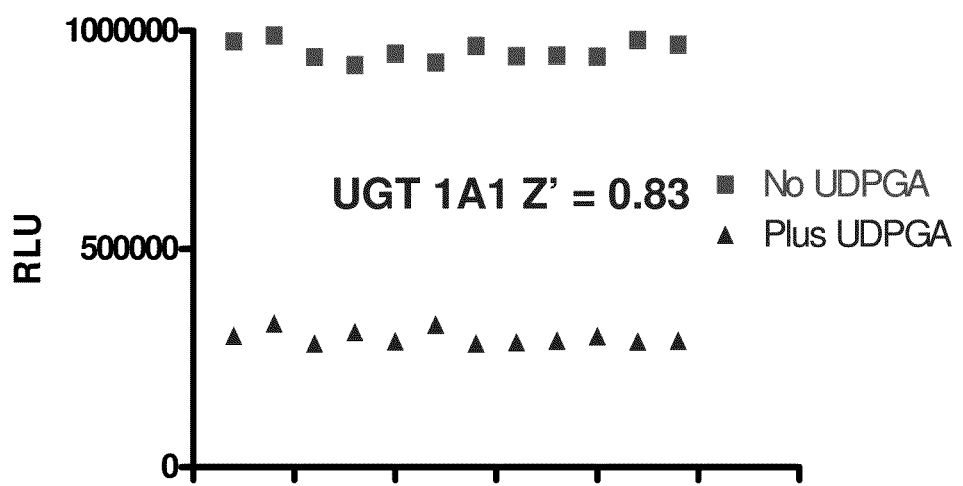
FIG. 12 illustrates data for UGT 1A1 for determining assay variability, according to an embodiment.

Data for UGT 1A1 is shown in FIG. 12. Z' values were calculated using the equation outlined below.

$$Z' = 1 - \frac{(3 * stdev_{noUDPGA} + 3 * stdev_{plusUDPGA})}{(RLU_{noUDPGA} - RLU_{plusUDPGA})}$$

Robust assay systems typically display Z' values of 0.5 or higher. The calculated Z' value for UGT 1A1 was 0.83. The calculated Z' value for UGT 2B7 under the same conditions was 0.67.

Example 7

Utilization of Benzothiazoles by GST Isozymes

A small amount of compound 934-37 was dissolved in DMSO to produce a solution approximately 1 mg/mL. This solution was diluted 1:100 (v/v) into 50 mM HEPES buffer pH 7.5 to produce a substrate solution. Twenty µL of this solution was placed in 10 wells of a 96 well white luminometer plate (Promega part Z3291), then the solution was diluted 1:3.1 and 20 µL of the dilution was placed into another 10 wells in the luminometer plate.

D-Cysteine, 4 mg (Sigma Chemical Corp.; C8005-1 g, 017K1034) was dissolved into 1 mL of 50 mM HEPES buffer pH 7.5, then 4 µL added to 4 of the wells containing the substrate solution and 4 of the wells with diluted substrate solution to convert compound 934-37 to the corresponding luciferin derivative. The structures of these compounds are shown below.

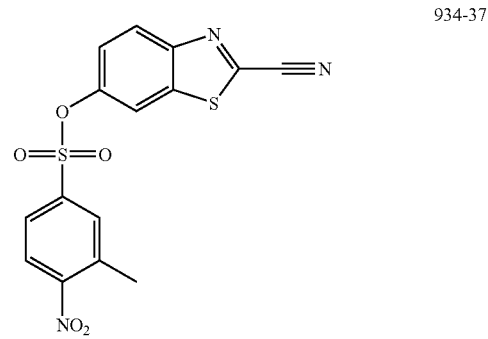

Converted 934-37

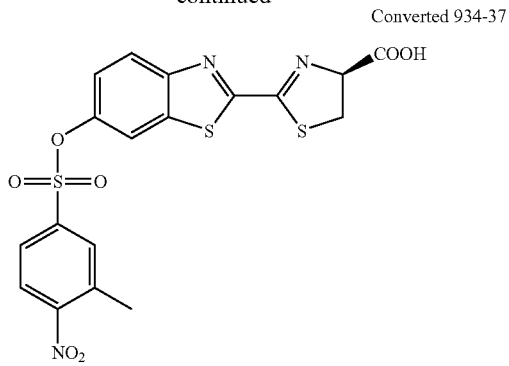

A sample of GST A1-1 (1.2 mg/mL) and 100 µL of 100 mM glutathione in water was diluted into 5 mL of 50 mM HEPES pH 7.5, then 25 µL added to: two of the wells with unconverted, concentrated compound 934-37; 2 wells with concentrated and converted compound 934-37; and two of the wells with unconverted, diluted compound 934-37 and 2 of the wells with converted, diluted compound 934-37.

A sample of GST M1-1 (1.2 mg/mL) and 100 µL of 100 mM glutathione was diluted into 5 mL of 50 mM HEPES pH 7.5, then 25 µL added to: two of the wells with unconverted, concentrated compound 934-37; 2 wells with concentrated and converted compound 934-37; and two of the wells with unconverted, diluted compound 934-37 and 2 of the wells with converted, diluted compound 934-37.

Glutathione (100 µL of 100 mM glutathione) had been diluted to 5 mL with 50 mM HEPES buffer pH 7.5, then 25 µL added to the remaining wells of converted and unconverted compound 934-37 in concentrated and diluted solution.

After 55 minutes at room temperature, 4 µL of the D-cysteine solution above was added to all wells that had not received cysteine before, then 50 µL of P450 Glo Luciferin Detection Reagent (made by dissolving a vial of Promega Luciferin Detection Reagent (Promega Part #V859B) with a vial of Promega P450-Glo Buffer (Promega Part #V865B). The plate was then placed into a Glo Max luminometer (Promega Corp.) and the light read after 15 minutes of incubation. The values obtained were averaged and the average value of the light produced from the wells given no enzyme were then subtracted from the average of the light produced with enzyme. The results are presented in the table below.

| Reaction | GST A1-1 | GST M1-1 |
| --- | --- | --- |
| Concentrated, untransformed substrate | 164,400 RLU | 41,212 RLU |
| Diluted, untransformed substrate | 195,021 RLU | 30,428 RLU |
| Concentrated, transformed substrate | 6,410 RLU | 315,759 RLU |
| Diluted, transformed substrate | 6,462 RLU | 213,920 RLU |

These data clearly show that GST A1-1 utilizes the substrate to a much faster extent in its untransformed state and essentially loses the ability to convert the material once it is converted to a luciferin derivative by addition of D Cys. However GST M1-1 shows much less ability to utilize the material in its unconverted state but utilizes the converted form of the substrate very well. This difference in utilization of the converted and unconverted forms can be used to determine if a sample contains one or both of these isozymes.

Example 8

Synthesis of
N-Peptidyl-6-Amino-2-Cyanobenzothiazoles

Protected N-peptidyl-6-amino-2-cyanobenzothiazoles can be prepared as described in U.S. Pat. No. 7,384,758 (O'Brien et al.). Deprotected derivatives can be prepared as follows.

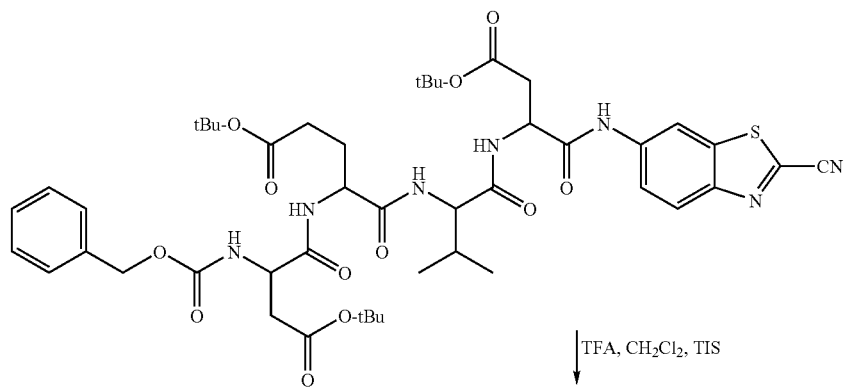

TFA, CH$_2$Cl$_2$, TIS

-continued

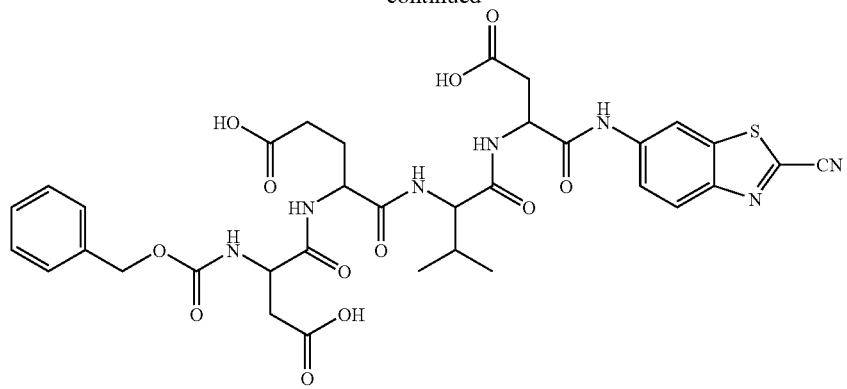

To an anhydrous solution of trifluoroacetic acid/dichloromethane/triisopropyl silane (50/50/2) is added the t-butyl protected N-peptidyl-6-amino-2-cyanobenzothiazole (U.S. Pat. No. 7,384,758). After 2 h, evaporate the solution to a syrup. Precipitate with diethyl ether. Wash solid twice with ethyl ether. Dry under vacuum. Purify on reverse-phase HPLC eluting with 20 mM NH4OAc.

Combine appropriate fractions and lyophilize to provide the de-tBu-protected compound. Removal of the Cbz group can be achieved under hydrogenation conditions (e.g., hydrogen gas in the presence of Pd/C)

Example 9

Cytochrome P450 Enzyme Panel Screen: Utilization of Benzothiazoles by Cytochrome P450 Enzymes Stock solutions of the benzothiazole compounds 3016, 3019, 3026, 3806, 3814, 3820, 3821, 3833, 3835, 3866, and 3868 were made at 50 mM in DMSO. One picomole of each P450 enzyme (Supersomes™, BD Bioscience) was incubated with 50 mM of each of the compounds in a 50 µl, reaction in KPO$_4$ buffer pH 7.4 (25 mM KPO$_4$ for CYP2C9, 50 mM KPO$_4$ for CYP2B6, -2C8, -2C19, -4F2, -4F3A and -4F3B, 100 mM KPO$_4$ for CYP1A1, -1A2, -1B1, -2D6, -2E1, -3A5, -3A7, -2J2, -4F12, -19 and minus P450 control, 200 mM KPO$_4$ for CYP3A4) or 100 mM Tris-HCl, pH 7.5 (for CYP2A6, -2C18 and -4A11). Reactions were initiated by adding an NADPH regenerating system (final concentrations of the regenerating system components in the assay were: 1.3 mM NADP$^+$, 3.3 mM glucose-6-phosphate, 3.3 mM MgCl$_2$, 0.4 U/mL glucose-6-phosphate dehydrogenase and 0.05 mM sodium citrate). Reactions were incubated for 30 minutes at 37° C. After incubation, 50 µl, of P450-Glo™ luciferin detection reagent (available from Promega Corp.) supplemented with 6.6 mM D-cysteine was added to each reaction, allowed to incubate at room temperature for 20 minutes, and luminescence was detected on a Veritas luminometer. FIGS. 14-25 demonstrate that the benzothiazole compounds can also be used to detect CYP450 enzyme activity as light output in this assay scheme. Each compound was active with one or more P450 enzymes and the profile of P450 activity varied across the panel of enzymes depending on the compound structure. The light output specific to a given P450 enzyme can be due to oxidation of the benzothiazole compound by the P450 enzyme to yield 6-hydroxybenzo[d]thiazole-2-carbonitrile (a benzothiazole derivative). The 6-hydroxybenzo-[d]thiazole-2-carbonitrile can then react with D-cysteine to form a D-luciferin derivative that in turns reacts with luciferase in the luciferin detection reagent to generate light in proportion to the amount of D-luciferin present.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A method to detect or determine the presence or activity of a nonluciferase enzyme in a sample comprising:
    a) contacting a sample with a first reaction mixture for a nonluciferase enzyme-mediated reaction and a derivative of 2-cyano-6-substituted benzothiazole which is a substrate for the nonluciferase enzyme and in the presence of D-cysteine yields a substrate for a beetle luciferase to form a first mixture;
    b) contacting at least a portion of the first mixture with a reaction mixture for a beetle luciferase-mediated reaction which includes D-cysteine; and
    c) detecting luminescence thereby detecting the presence of the nonluciferase enzyme in the sample.

2. The method of claim 1 wherein the luminescence is quantified.

3. The method of claim 1, wherein the luminescence is compared to a control that excludes a cofactor for the nonluciferase enzyme.

4. The method of claim 1 wherein the sample comprises a cell or cells expressing a nonluciferase enzyme or cell medium from a cell or cells expressing a nonluciferase enzyme.

5. The method of claim 1 wherein the nonluciferase enzyme comprises UDP-glucuronosyl transferase (UGT), glutathione S transferase (GST), cytochrome P450 (CYP450), flavin monoamine oxidase (FMO), histone deacetylase (HDAC), or a protease.

6. The method of claim 1 wherein the nonluciferase enzyme is UGT.

7. The method of claim 1 wherein the nonluciferase enzyme is CYP450.

8. The method of claim 1 wherein the first reaction mixture further comprises a test modulator of a nonluciferase enzyme-mediated reaction.

9. The method of claim 8 wherein the test modulator is an inhibitor of the nonluciferase enzyme, a substrate for the nonluciferase enzyme that competes with the derivative, or an activator of the nonluciferase enzyme.

10. The method of claim 1 wherein the derivative of 2-cyano-6-substituted benzothiazole is a compound of formula I:

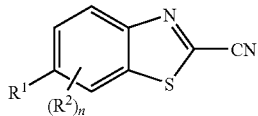

wherein
R$^1$ is OH, OR$^x$, OSO$_2$R$^x$, or NHR$^x$;
R$^2$ is (C$_1$-C$_3$)alkyl, trifluoromethyl, amino, nitro, or halo;
n is 0, 1, 2, or 3; and
R$^x$ is alkyl, aryl or (C$_1$-C$_3$)alkylaryl wherein the alkyl or aryl is optionally substituted with one to five halo, hydroxy, nitro, alkyl or amino groups.

11. The method of claim 10 wherein the compound of formula I is

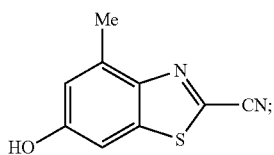

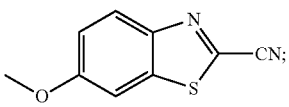

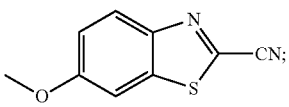

-continued

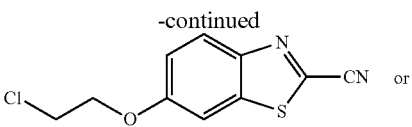

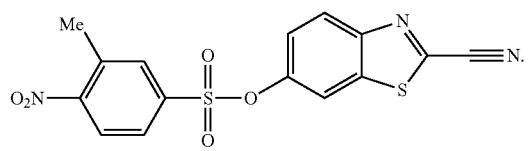

12. The method of claim 1 wherein the derivative of 2-cyano-6-substituted benzothiazole is a compound of formula XV:

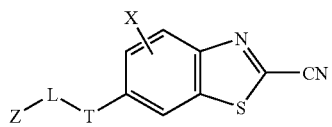

wherein
Z is hydrogen or a protecting group;
L is an amino acid or a chain of 2-10 amino acids;
T is O or NH; and
X is hydrogen or fluorine, with the proviso that if X is H then at least one of the amino acids is R, N, D, C, Q, E, H, K, S, T, W, or Y.

13. The method of claim 12 wherein Z is a protecting group and the protecting group is a nitrogen protecting group or an oxygen protecting group.

14. The method of claim 12 wherein Z is Cbz, Boc, acetyl, or succinyl.

15. The method of claim 12 wherein the compound of formula XV is:

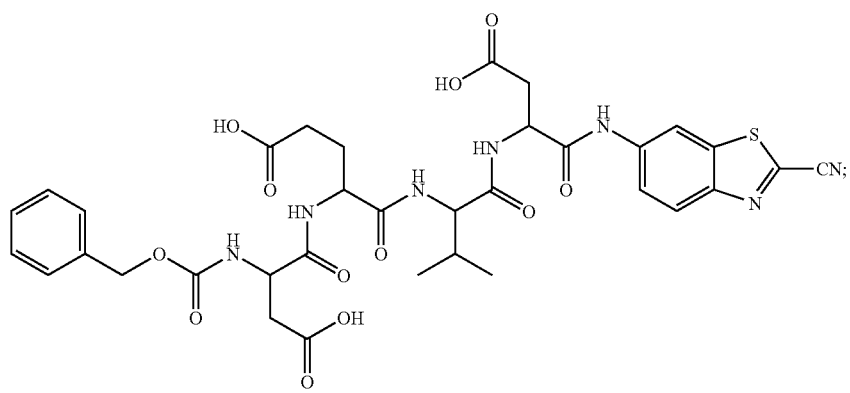

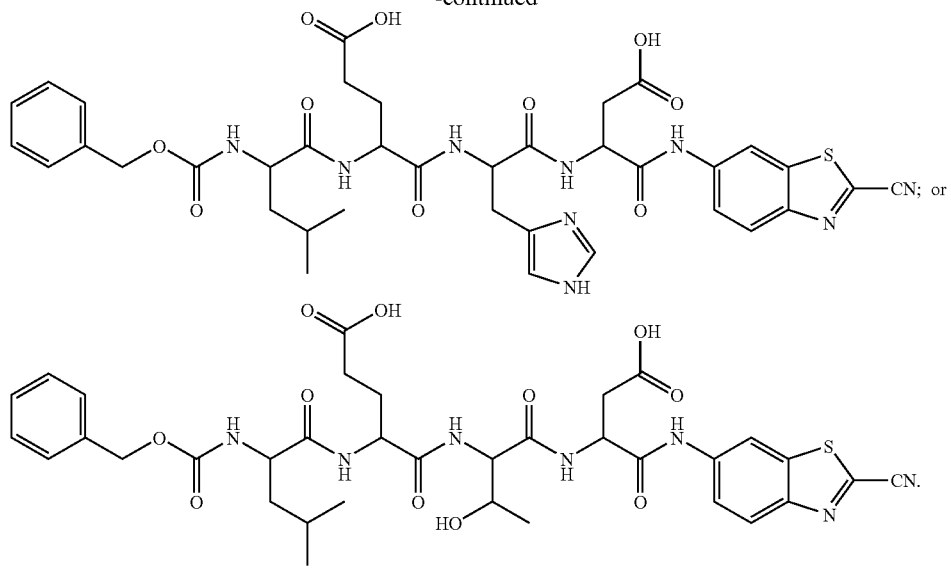

16. A method to detect or determine activity of a nonluciferase enzyme modulator in a sample comprising
   a) contacting a sample that includes microsomes containing a nonluciferase enzyme with a first reaction mixture for the nonluciferase enzyme-mediated reaction, a test modulator of the activity of the nonluciferase enzyme, and a derivative of 2-cyano-6-substituted benzothiazole which is a substrate for the nonluciferase enzyme and in the presence of D-cysteine yields a substrate for a beetle luciferase to form a first mixture;
   b) contacting at least a portion of the first mixture with a reaction mixture for a beetle luciferase-mediated reaction which includes D-cysteine; and
   c) detecting luminescence thereby detecting or determining the modulation activity of the test modulator.

17. The method of claim 16 wherein the luminescence is quantified.

18. The method of claim 16 wherein the luminescence is increased as compared to a control.

19. The method of claim 16 wherein the luminescence is decreased as compared to a control.

20. The method of claim 16 wherein the luminescence is compared to a control that excludes a cofactor for the nonluciferase enzyme.

21. The method of claim 16 wherein the nonluciferase enzyme comprises UDP-glucuronosyl transferase (UGT), glutathione S transferase (GST), cytochrome P450 (CYP450), flavin monoamine oxidase (FMO), histone deacetylase (HDAC), or a protease.

22. The method of claim 16 wherein the nonluciferase enzyme is UGT.

23. The method of claim 16 wherein the nonluciferase enzyme is CYP450.

24. The method of claim 16 wherein the test modulator is an inhibitor of the nonluciferase enzyme, a competitive substrate for the nonluciferase enzyme, or an activator of the nonluciferase enzyme.

25. The method of claim 16 wherein the microsomes containing UGT express a specific UGT enzyme.

26. The method of claim 16 wherein the microsomes containing CYP450 express a specific CYP450 isozyme.

27. The method of claim 16 wherein the derivative of 2-cyano-6-substituted benzothiazole is a compound of formula I:

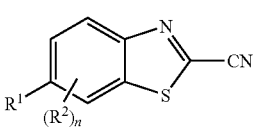

wherein
   $R^1$ is OH, $OR^x$, $OSO_2R^x$, or $NHR^x$;
   $R^2$ is $(C_1$-$C_3)$alkyl, trifluoromethyl, amino, nitro, or halo;
   n is 0, 1, 2, or 3; and
   $R^x$ is alkyl, aryl or $(C_1$-$C_3)$alkylaryl wherein the alkyl or aryl is optionally substituted with one to five halo, hydroxy, nitro, alkyl or amino groups.

28. The method of claim 27 wherein the compound of formula I is

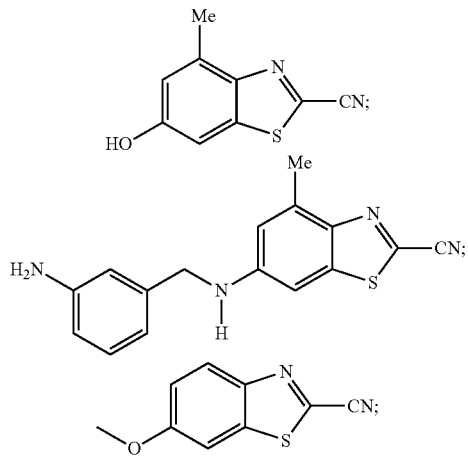

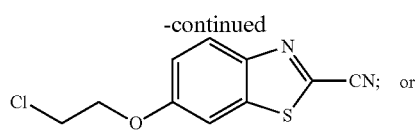

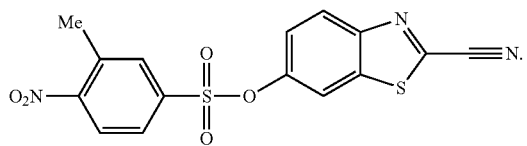

29. The method of claim 16 wherein the derivative of 2-cyano-6-substituted benzothiazole is a compound of formula XV:

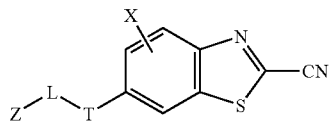

wherein

Z is hydrogen or a protecting group;

L is an amino acid or a chain of 2-10 amino acids;

T is O or NH; and

X is hydrogen or fluorine, with the proviso that if X is H then at least one of the amino acids is R, N, D, C, Q, E, H, K, S, T, W, or Y.

30. The method of claim 29 wherein Z is a protecting group and the protecting group is a nitrogen protecting group or an oxygen protecting group.

31. The method of claim 29 wherein Z is Cbz, Boc, acetyl, or succinyl.

32. The method of claim 29 wherein the compound of formula XV is:

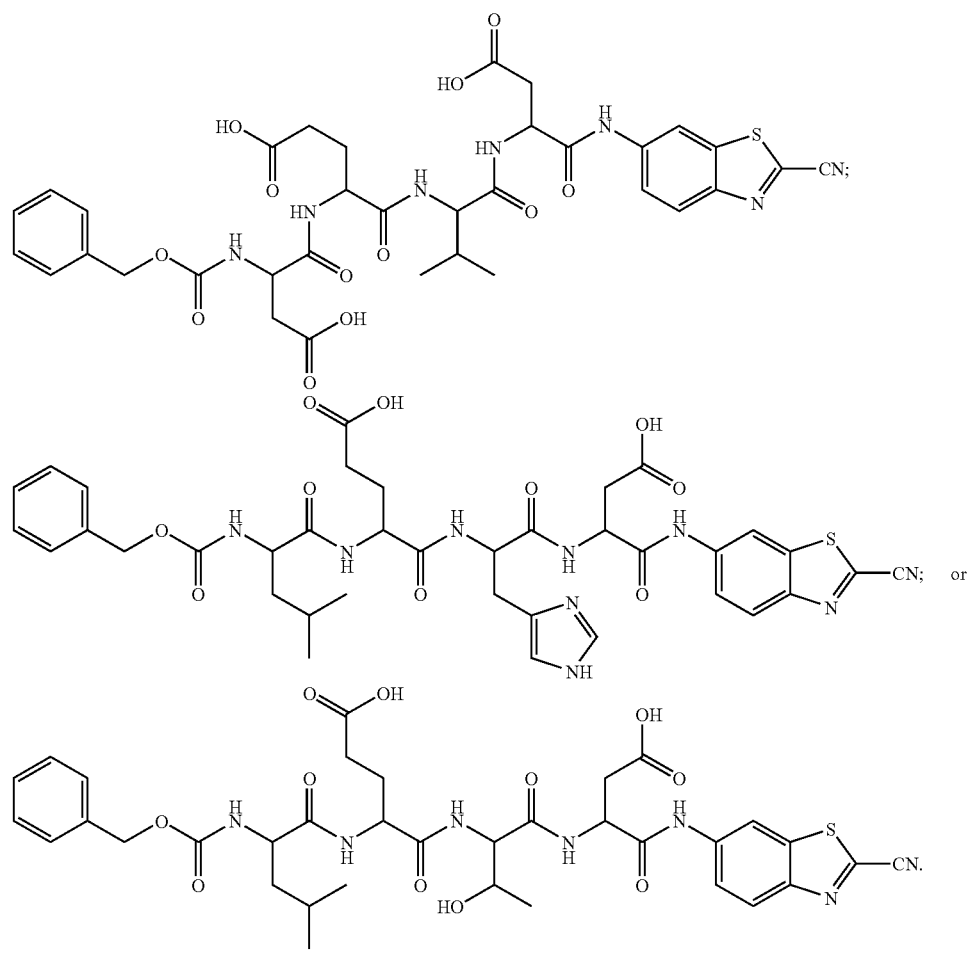

33. A compound selected from the group consisting of:
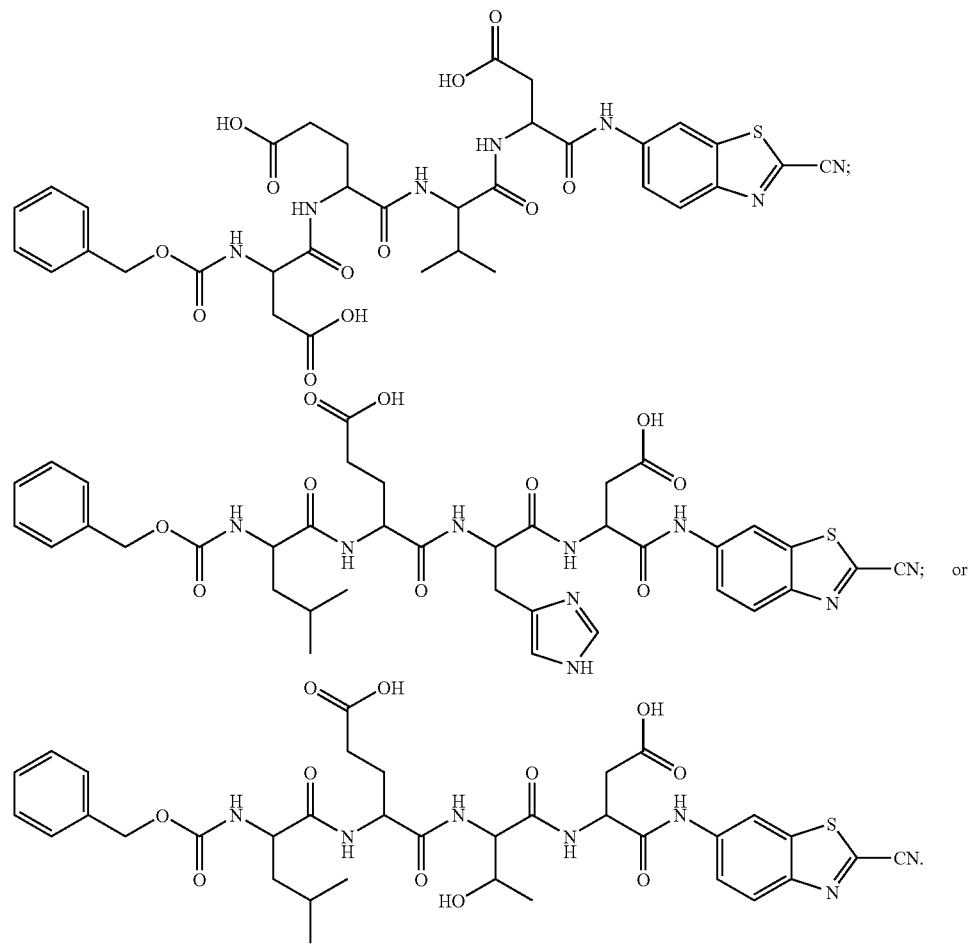
* * * * *